United States Patent
Moghadam et al.

(10) Patent No.: US 12,080,391 B2
(45) Date of Patent: Sep. 3, 2024

(54) AUTOMATED ELECTRONIC PATIENT CARE RECORD DATA CAPTURE

(71) Applicant: ZOLL Medical Corporation, Chelmsford, MA (US)

(72) Inventors: Alexander N. Moghadam, Boulder, CO (US); Gary A. Freeman, Waltham, MA (US); Keenan S. Early, Denver, CO (US); Angela L. Baca DeGarie, Golden, CO (US); Peter G. Goutmann, Gibsonia, PA (US); Allyn E. Scott, Boulder, CO (US); John R. Whannel, Littleton, CO (US)

(73) Assignee: ZOLL Medical Corporation, Chelmsford, MA (US)

( * ) Notice: Subject to any disclaimer, the term of this patent is extended or adjusted under 35 U.S.C. 154(b) by 249 days.

(21) Appl. No.: 17/396,206

(22) Filed: Aug. 6, 2021

(65) Prior Publication Data

US 2022/0044772 A1 Feb. 10, 2022

Related U.S. Application Data

(60) Provisional application No. 63/062,463, filed on Aug. 7, 2020.

(51) Int. Cl.
*G06F 17/00* (2019.01)
*A61B 5/00* (2006.01)
(Continued)

(52) U.S. Cl.
CPC .......... *G16H 10/60* (2018.01); *A61B 5/7405* (2013.01); *A61B 5/742* (2013.01); *A61B 5/7455* (2013.01);
(Continued)

(58) Field of Classification Search
CPC ...... G16H 10/60; G16H 40/67; A61B 5/7405; A61B 5/742; A61B 5/7455; A61B 5/746;
(Continued)

(56) References Cited

U.S. PATENT DOCUMENTS

| 6,117,073 A | 9/2000 | Jones et al. |
| 6,684,276 B2 | 1/2004 | Walker et al. |

(Continued)

FOREIGN PATENT DOCUMENTS

| WO | 2011116340 A2 | 9/2011 |
| WO | 2020172446 A1 | 8/2020 |

OTHER PUBLICATIONS

Sarah Preum, Sile Shu, Mustafa Hotaki, Ronald Williams, John Stankovic, and Homa Alemzadeh. 2019. CognitiveEMS: a cognitive assistant system for emergency medical services. SIGBED Rev. 16, 2 (Jul. 2019), 51-60. <https://doi.org/10.1145/3357495.3357502> July (Year: 2019).*

(Continued)

*Primary Examiner* — Greta L Robinson
(74) *Attorney, Agent, or Firm* — Finch & Maloney PLLC

(57) ABSTRACT

A patient data charting system for automated data capture by an electronic patient care record (ePCR) generated during a patient encounter with emergency medical services (EMS) includes a local computing device including a processor, and a memory storing an ePCR including ePCR data fields, and a user interface device communicatively coupled to the local computing device and including a microphone and speaker, wherein the microphone may be configured to capture spoken patient encounter information, wherein the processor may be configured to receive the spoken patient encounter information as text information from a speech-to-text conversion application, determine at least one ePCR data field value based on the text information, populate at least one (Continued)

ePCR data field with the at least one ePCR data field value, generate caregiver prompts based on the at least one ePCR data field value, and provide the audible caregiver prompts to the caregiver via the speaker.

25 Claims, 32 Drawing Sheets

(51) Int. Cl.
  *G16H 10/60* (2018.01)
  *G16H 40/67* (2018.01)
(52) U.S. Cl.
  CPC .............. *A61B 5/746* (2013.01); *A61B 5/747* (2013.01); *A61B 5/749* (2013.01); *G16H 40/67* (2018.01)
(58) Field of Classification Search
  CPC ....... A61B 5/747; A61B 5/749; A61B 5/0002; A61B 5/0075; A61B 5/021; A61B 5/024; A61B 5/053; A61B 5/0816; A61B 5/083; A61B 5/318; A61B 5/1455; A61N 1/37247; A61N 1/37258; A61N 1/3904; A61N 1/3993
  See application file for complete search history.

(56) References Cited

U.S. PATENT DOCUMENTS

| | | | |
|---|---|---|---|
| 7,039,628 B2 | 5/2006 | Logan, Jr. | |
| 7,133,937 B2* | 11/2006 | Leavitt | G16H 10/60 710/1 |
| 7,949,544 B2* | 5/2011 | Miglietta | G16H 10/60 705/2 |
| 8,165,876 B2 | 4/2012 | Emam et al. | |
| 10,086,231 B2 | 10/2018 | Hall | |
| 10,453,157 B2 | 10/2019 | Kamen et al. | |
| 11,146,680 B2* | 10/2021 | Leavitt | G16H 40/20 |
| 11,342,075 B2* | 5/2022 | Podobas | G16H 15/00 |
| 2003/0115060 A1 | 6/2003 | Junqua et al. | |
| 2004/0088317 A1 | 5/2004 | Fabrick et al. | |
| 2008/0133572 A1 | 6/2008 | Verhey-Henke et al. | |
| 2011/0184759 A1* | 7/2011 | Selker | G16H 10/60 705/3 |
| 2011/0295078 A1* | 12/2011 | Reid | G06Q 10/10 600/300 |
| 2012/0191476 A1 | 7/2012 | Reid et al. | |
| 2012/0304054 A1 | 11/2012 | Orf et al. | |
| 2014/0222805 A1* | 8/2014 | Huang | G16H 10/60 707/732 |
| 2015/0120794 A1 | 4/2015 | Phelan et al. | |
| 2015/0248917 A1 | 9/2015 | Change et al. | |
| 2016/0070864 A1 | 3/2016 | Dotan et al. | |
| 2017/0169166 A1* | 6/2017 | Colley | G16H 15/00 |
| 2017/0323055 A1* | 11/2017 | Gaffield | G06F 16/9535 |
| 2018/0068074 A1 | 3/2018 | Shen | |
| 2018/0122506 A1 | 5/2018 | Grantcharov et al. | |
| 2018/0375804 A1 | 12/2018 | Stillwell, Jr. et al. | |
| 2019/0282324 A1 | 9/2019 | Freeman et al. | |
| 2020/0051675 A1 | 2/2020 | Nelson et al. | |
| 2020/0075140 A1* | 3/2020 | Embree | G16H 40/60 |
| 2020/0258511 A1 | 8/2020 | Barkol et al. | |

OTHER PUBLICATIONS

Kumah-Crystal et al, (Jul. 18, 2018). Electronic health record interactions through voice: A review. Applied Clinical Informatics. https://www.thieme-connect.de/products/ejournals/abstract/10.1055/s-0038-1666844.

* cited by examiner

AUTOMATED ELECTRONIC PATIENT CARE RECORD DATA CAPTURE

CROSS REFERENCE TO RELATED APPLICATIONS

This application claims priority under 35 U.S.C. § 119(e) to U.S. Provisional Application Ser. No. 63/062,463, titled "AUTOMATED ELECTRONIC PATIENT CARE RECORD DATA CAPTURE," filed Aug. 7, 2020, which is hereby incorporated herein by reference in its entirety.

BACKGROUND

Emergency medical services (EMS) agencies create and use an electronic patient care record (ePCR) for each patient encounter. The ePCR contains a complete record of medical observations and treatments for the patient during the patient encounter. The ePCR also includes times for the observations and treatments, patient medical history information, and transport information (e.g., from a scene of an emergency to a medical care facility). Often in an emergency encounter, the EMS caregiver is interacting with a critically ill patient for the first time with no prior medical knowledge about the patient. The emergency encounter is often in a non-medical environment like a home, office, or gym. In many cases, the encounter occurs in the chaotic environment of a fire scene, a car accident, or a mass casualty scene. Based in part on the complexities of medical diagnosis and care in these situations along with state and federal reporting guidelines and billing guidelines, the ePCR is typically a complex and lengthy document with approximately 50-300 required field entries. Accurate completion of this document is critical for efficacious medical treatment during the patient encounter and during follow-on care at the medical facility. Additionally, accurate and expedient billing also require the accurate completion of the ePCR.

SUMMARY

An example of a patient data charting system for automated data capture by an electronic patient care record (ePCR) generated during a patient encounter with emergency medical services (EMS) according to the disclosure may include a local computing device including a processor, and a memory storing an ePCR including a plurality of ePCR data fields, and at least one user interface device communicatively coupled to the local computing device and including a microphone and a speaker, wherein the microphone may be configured to capture spoken patient encounter information, wherein the processor may be configured to receive the spoken patient encounter information as text information from a speech-to-text conversion application, determine at least one ePCR data field value based on the text information, populate at least one ePCR data field with the at least one ePCR data field value, generate one or more caregiver prompts based on the at least one ePCR data field value, and provide the one or more caregiver prompts to the speaker, and wherein the speaker may be configured to provide the one or more caregiver prompts as audible prompts for a caregiver.

Implementations of such a system may include one or more of the following features. The speech-to-text conversion application may reside on the local computing device. The processor may be configured to wirelessly receive the captured spoken patient encounter information from the at least one user interface device, and provide the captured spoken patient encounter information to the speech-to-text conversion application. The system may include a remote computing device communicatively coupled to the local computing device, wherein the speech-to-text conversion application resides on the remote computing device. The processor may be configured to wirelessly receive the captured spoken patient encounter information from the at least one user interface device, provide the captured spoken patient encounter information to the remote computing device via a communication network, and receive the text information from the remote computing device via the communication network. The at least one user interface device may include a wearable user interface device that includes one or more of an earpiece, a watch, and glasses. The local computing device may include a location device configured to determine location information associated with the patient encounter, and wherein the processor may be configured to determine the at least one ePCR data field value based on the location information. The location device may be a global positioning system (GPS) device, a wireless communications device, or a combination thereof. The at least one ePCR data field value may include times determined from the location information. The processor may be configured to generate a geofence and the times determined from the location information may be based on the geofence. The times may include one or more of an en-route-to-patient-scene time, an at-patient-arrival-time, an at-patient-side duration time, an in-transport time, an estimated time of arrival at a hospital, and a hospital arrival time. The text information may include one or more predetermined keywords and the processor may be configured to identify the at least one ePCR data field based on the one or more predetermined keywords. The one or more predetermined keywords may correspond to an ePCR data field identifier. The one or more predetermined keywords may correspond to ePCR data field values. The processor may be configured to populate at least one additional ePCR data field with an inferred data field value based on the at least one of the ePCR data field values. The spoken patient encounter information may include caregiver speech and patient speech, and the processor may be configured to recognize that the spoken patient encounter information may include the patient speech, and differentiate between the patient speech and the caregiver speech. The microphone may be a first microphone configured to capture the spoken patient encounter information from the caregiver and the system may include a second microphone configured to capture the patient speech. The processor may be configured to differentiate between the patient speech and the caregiver speech based on whether the spoken patient encounter information may be from the first microphone or the second microphone. The processor may be configured to differentiate between the patient speech and the caregiver speech based on voice recognition of the caregiver speech. The processor may be configured to identify a portion of the plurality of ePCR data fields based on the caregiver speech and to determine data field values from the portion of the plurality of ePCR data fields based on the patient speech. Based on the recognition that the spoken patient encounter information may include the patient speech, the processor may be configured to determine a null value for at least one ePCR data field that may be incompatible with a verbally responsive patient. The at least one ePCR data field may be in a cardiac arrest data section of the ePCR. The ePCR may be NEMSIS compliant and the at least one data field in the cardiac arrest data section of the ePCR may be an eArrest data field. The at least one ePCR data field may be in an airway data section of the ePCR. The ePCR may be NEMSIS compliant and the at least one data field in the airway data section of the ePCR may be an eAirway data field. The processor may be configured to determine date and time values corresponding to an ePCR data field for a start of the patient encounter based on the recognition that the spoken patient encounter information may include the patient speech. The processor may be configured to identify at least one unpopulated ePCR data field associated with at least one populated ePCR data field, and generate a caregiver prompt including at least one request for at least one data field value for the at least one unpopulated ePCR data field. The processor may be configured to identify the at least one unpopulated ePCR data field based on a medical protocol stored in the memory. The processor may be configured to cause the speaker to repeat the caregiver prompt including the at least one request for the at least one data field value. The repeat may occur until the processor receives a caregiver response via the microphone. The repeat may occur for a pre-determined number of cycles. The at least one user interface device may be configured to provide the one or more caregiver prompts as haptic prompts. The one or more caregiver prompts may include reminders of patient care activities based on the at least one ePCR data field value and a medical protocol. The one or more caregiver prompts may include alarms based on the at least one ePCR data field value. The alarms may include timed alarms for one or more patient care activities medically necessitated by the at least one ePCR data field value according to a medical protocol stored in the memory. The timed alarms for the one or more patient care activities may include timed alarms for one or more of drug administration and a 12-lead ECG measurement. The alarms may include patient care warnings based on the at least one ePCR data field value. The patient care warnings may include one or more of a drug contraindication and a medical therapy contraindication. The at least one ePCR data field value may include at least one physiological parameter and the processor may be configured to compare the at least one physiological parameter to a target value or range, determine that the at least one physiological parameter may be unequal to the target value or outside of the range, and generate a patient care warning that indicates that the at least one physiological parameter may be unequal to the target value or outside of the range. The at least one physiological parameter may include a patient vital sign. The local computing device may be configured to communicatively couple to an EMS dispatch system and the processor may be configured to receive EMS dispatch information, and determine one or more ePCR data field values based on the EMS dispatch information. The local computing device may be configured to communicatively couple to a medical records database and the processor may be configured to receive medical records database information, and determine one or more ePCR data field values based on the medical records database information. The local computing device may be configured to communicatively couple to one or more medical devices and the processor may be configured to receive patient data from the one or more medical devices, and determine one or more ePCR data field values based on the patient data from the one or more medical devices.

An example of a patient data charting system for automated data capture by an electronic patient care record (ePCR) generated during a patient encounter with an emergency medical services (EMS) caregiver team according to the disclosure includes a local computing device including a processor, and a memory storing an ePCR including a plurality of ePCR data fields, and a first user interface device and a second user interface device, each user interface device associated with a respective caregiver and communicatively coupled to the local computing device and configured to capture patient encounter information, and transmit the patient encounter information to the local computing device, wherein the processor may be configured to receive first patient encounter information from the first user interface device, receive second patient encounter information from the second user interface device, determine at least one ePCR data field value based on at least one of the first and second patient encounter information, populate at least one ePCR data field with the at least one ePCR data field value, generate one or more caregiver prompts based on the at least one ePCR data field value, and provide the one or more caregiver prompts to at least one of the first and second user interface devices.

Implementations of such a system may include one or more of the following features. The processor may be configured to identify the first user interface device as a source of the first patient encounter information and the second user interface device as a source of the second patient encounter information based on source identification information. The source identification information may include a first device identifier processor identifier from the first user interface device and a second device identifier from the second user interface device. The processor may be configured to receive the source identification information during pairing operations with the first and second user interface devices. The processor may be configured to receive the source identification information as metadata with the first and second patient encounter information. The processor may be configured to provide a caregiver prompt for the second user interface device based on the first patient encounter information received from the first user interface device. The processor may be configured to provide the caregiver prompt for the second user interface device based on the first patient encounter information received from the first user interface device in response to a query received at the processor from the second user interface device. The caregiver prompt for the second user interface device may include an alarm based on the first patient encounter information received from the first user interface device. The alarm may include a timed alarm for one or more patient care activities associated with the first patient encounter information received from the second user interface device. The alarm may include a patient care warning based on the first patient encounter information received from the second user interface device. The patient care warning may include one or more of a drug contraindication and a medical therapy contraindication. The at least one ePCR data field value may include at least one physiological parameter and wherein the processor may be configured to compare the at least one physiological parameter to a target value or range, determine that the at least one physiological parameter may be unequal to the target value or outside of the range, and generate the alarm including an indication that the at least one physiological parameter may be unequal to the target value or outside of the range. The at least one physiological parameter may include a patient vital sign. The processor may be configured to associate the first user interface device with a first section of the ePCR, populate first ePCR data fields in the first section of the ePCR based on the first patient encounter information, associate the second user interface device with a second section of the ePCR, and populate second ePCR data fields in the second section of the ePCR based on the second patient encounter information. The processor may be configured to identify a first data field value from the first patient encounter information and a second data field value from the second patient encounter information that both correspond to a same ePCR data field, and populate the same ePCR data field with one or more of the first data field value and the second data field value according to pre-determined selection rules. The same ePCR data field may be a single use field and the processor may be configured to populate the same ePCR data field with only the first data field value according to the pre-determined selection rules. The same ePCR data field may be a single use field and the processor may be configured to populate the same ePCR data field with the first data field value in response to the reception of the first patient encounter information, generate a caregiver prompt for one or more of the first and second user interface devices in response to the reception of the second patient encounter information, receive a caregiver response to the caregiver prompt, and replace the first data field value with the second data field value based on the caregiver response. The same ePCR data field may be a multi-use field and the processor may be configured to populate the same ePCR data field with the first data field value and the second data field value. The processor may be configured to generate a team alert based on the at least one ePCR data field value, and provide the team alert to the first and second user interface devices. The team alert may include one or more of patient medication information, patient allergy information, a vital sign measurement, a change in the vital sign measurement, and a physiological parameter for the patient. The processor may be configured to identify a change in at least one ePCR data field value that corresponds to a patient status, and the team alert may include a patient status change alarm. The processor may be configured to generate a medication alert based on one or more ePCR data fields corresponding to at least one of a medication history data field and an administered medication data field, and the team alert may include the medication alert. The system may include at least one location device configured to determine location information associated with the patient encounter, wherein the processor may be configured to determine at least one ePCR data field value that may include a time based on the location information. The at least one ePCR data field value may include at least one of an en-route-to-patient-scene time, an at-patient-arrival-time, an at-patient-side duration time, an in-transport time, an estimated time of arrival at a hospital, and a hospital arrival time. The processor may be configured to generate a timing alert based on the time based on the location information, and the team alert may include the timing alert. The at least one location device may be a global positioning system, a wireless communications positioning system, or a combination thereof.

An example of patient data charting system for automated data capture by an electronic patient care record (ePCR) generated during a patient encounter with an emergency medical services (EMS) caregiver team according to the disclosure includes a memory storing an ePCR application and a stored ePCR including a plurality of ePCR data fields, at least one processor configured to execute the ePCR application, and augmented reality (AR) glasses including at least one input device communicatively coupled to the at least one processor and including a microphone configured to capture patient encounter information as audio input, one or more output devices communicatively coupled to the at least one processor and including a speaker and at least one display, wherein the at least one processor configured to execute the ePCR application may be configured to receive patient encounter information captured by the microphone, determine a plurality of ePCR data field values based on the patient encounter information, populate the plurality of ePCR data fields in the stored ePCR with the plurality of ePCR data field values, and generate one or more caregiver prompts based on the plurality of ePCR data field values, and control the one or more output devices to provide the one or more caregiver prompts.

Implementations of such a system may include one or more of the following features. The at least one processor and the memory may be disposed on the AR glasses. The system may include a computer tablet communicatively coupled to the AR glasses, the computer tablet including the memory and the at least one processor. The at least one processor may be configured to control the AR glasses to provide a drop-down menu corresponding to at least one ePCR data field at the at least one display. The at least one processor may be configured to receive a selection from the drop-down menu via the microphone. The drop-down menu may include a virtual touchpad configured to capture a user selection from the drop-down menu via a hand gesture, and provide the user selection to the at least one processor. The at least one processor may be configured to control the AR glasses to provide the drop-down menu in response to an audible request captured by the microphone. The at least one processor may be configured to control the at least one display to provide the one or more caregiver prompts. The one or more caregiver prompts may include alarms based on the plurality of ePCR data field values and the at least one processor may be configured to control the at least one display to display the alarms as graphical, textual, and/or numerical information. The alarms may include timed alarms for one or more patient care activities medically necessitated by the plurality of ePCR data field values according to a medical protocol. The timed alarms for the one or more patient care activities may include timed alarms for one or more of a patient treatment and a patient evaluation. The alarms may include patient care warnings based on at least one of the plurality of ePCR data field values. The patient care warnings may include one or more of a drug contraindication and a medical treatment contraindication. The alarms may include a patient physiological parameter warning based on at least one patient physiological parameter in the stored ePCR. The patient encounter information captured by the microphone may include the at least one patient physiological parameter. The system may include a medical device communicatively coupled to the at least one processor and wherein the at least one processor may be configured to receive medical device information including the at least one patient physiological parameter from the medical device. The at least one processor may be configured to compare at least one physiological parameter in the stored ePCR to a target value or range, determine that the at least one physiological parameter may be unequal to the target value or outside of the range, and generate the patient physiological parameter warning including an indication that the at least one physiological parameter may be unequal to the target value or outside of the range. The at least one processor may be configured to compare a second value of a physiological parameter to a first value of the physiological parameter in the stored ePCR, detect a difference between the second value and the first value, generate the patient physiological parameter warning including an indication of the detected difference between the second value and the first value. The at least one processor may be configured to assign an urgency rating to the alarms based on a medical protocol stored in the memory, and control the at least one display to indicate the urgency rating with one or more of a color alarm display and a flashing alarm display. The system may include a location device configured to determine location information associated with the patient encounter, wherein the at least one processor may be configured to determine at least one time corresponding to at least one ePCR data field value based on the location information, and control the at least one display to display the at least one time. The at least one time may include at least one of an en-route-to-patient-scene time, an at-patient-arrival-time, an at-patient-side duration time, an in-transport time, an estimated time of arrival at a hospital, and a hospital arrival time. The at least one time may be displayed as a countdown timer or a clock time. The location device may be a global positioning system, a wireless communications positioning system, or a combination thereof. The at least one processor may be configured to identify a medical procedure based on at least one ePCR data field values, and control the AR glasses to display medical procedure instructions for the identified medical procedure, and as virtual objects superimposed on a real-space view of one or more of a patient and an item of medical equipment. The AR glasses may include a camera communicatively coupled to the at least one processor. The camera may be configured to capture a bar code and/or a QR code in response to one or more of an audible, gesture, and/or a tactile signal from a caregiver. The at least one processor may be configured to populate one or more of a medication ePCR data field, a medical equipment ePCR data field, and a medical procedure ePCR data field based on the bar code and/or the QR code. The camera may be configured to capture an image of at least a portion of a patient's body in response to one or more of an audible, gesture, and/or a tactile signal from a caregiver and the at least one processor may be configured to analyze the image of the portion of the patient's body to identify a side of the patient's body including the imaged portion as a right side of the patient's body or a left side of the patient's body, provide a caregiver prompt requesting confirmation of the side of the patient's body, in response to a caregiver confirmation, populate patient encounter information associated with the portion of the patient's body in ePCR data fields assigned to the side of the patient's body. The ePCR data fields assigned to the side of the patient's body may include one or more of a limb data field, a torso data field, a head data field, and an organ data field. The at least one processor may be configured to receive the audio input as text information from a speech-to-text conversion application residing on a remote server communicatively coupled to the at least one processor. The at least one processor may be configured to execute a speech-to-text application stored in the memory. The at least one processor may be configured to communicatively couple to an EMS dispatch system, receive EMS dispatch information, and determine one or more ePCR data field values based on the EMS dispatch information. The at least one processor may be configured to communicatively couple to a medical records database, receive medical records database information, and determine one or more ePCR data field values based on the medical records database information. The at least one processor may be configured to communicatively couple to one or more medical devices, receive patient data from the one or more medical devices, and determine one or more ePCR data field values based on the patient data from the one or more medical devices.

Other capabilities may be provided and not every implementation according to the disclosure must provide any, let alone all, of the capabilities discussed. Further, it may be possible for an effect noted above to be achieved by means other than that noted and a noted item/technique may not necessarily yield the noted effect.

BRIEF DESCRIPTION OF THE DRAWINGS

Various aspects of the disclosure are discussed below with reference to the accompanying figures, which are not intended to be drawn to scale. The figures are included to provide an illustration and a further understanding of various examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure. A quantity of each component in a particular figure is an example only and other quantities of each, or any, component could be used.

DETAILED DESCRIPTION

Figure 1A:
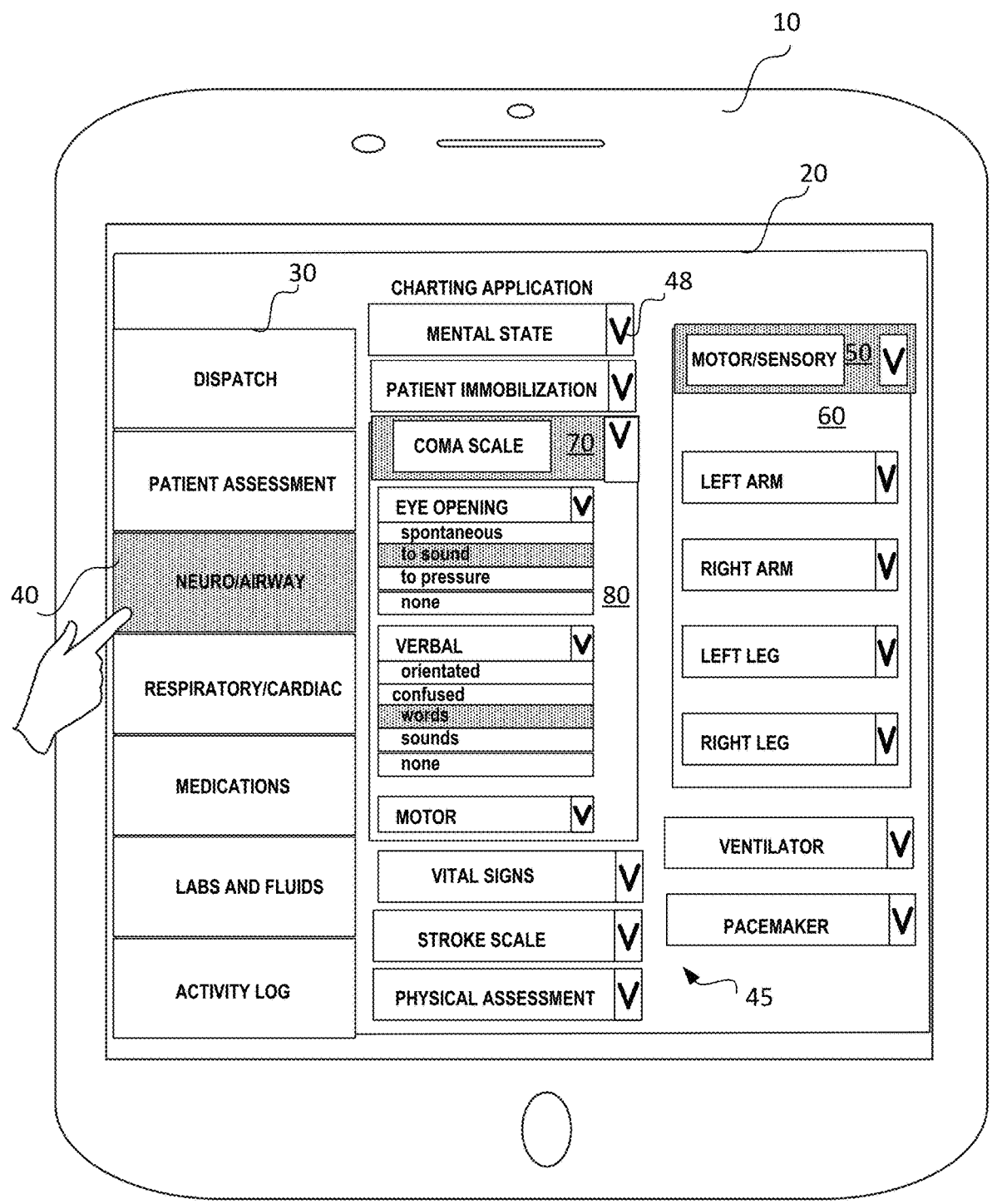
FIG. 1A shows an example of a manually populated ePCR.

Complete and accurate patient medical records, including patient biographical information, medical condition, medications, allergies, and the like may impact accurate diagnosis and treatment. For example, consider an illustrative scenario of a crew of emergency medical services (EMS) caregivers in an ambulance being called upon to treat a patient suffering from an emergency medical condition (e.g., cardiac arrest, trauma, respiratory distress, drug overdose, etc.) and to transport the patient to a hospital. During the course of this emergency encounter, the EMS caregivers may be required to generate an electronic PCR (ePCR). This ePCR may comprise information regarding the patient, such as observed patient symptoms during the encounter, observed patient physiological parameters (such as heart rate, ECG traces, temperature, blood-oxygen data, and the like), and treatments or medications administered during the encounter. The patient charting information may include information, such as any known allergies to medication, relevant medical history, and/or additional patient medical conditions. This patient charting information may also include patient demographic information and/or information regarding the emergency medical event, such as type of service requested, response mode, and triage classification.

In order to provide a complete and accurate ePCR for an emergency medical services patient encounter, the caregivers need to enter patient care record data contemporaneously with, i.e., during, the ongoing encounter. However, entering this data during the encounter diverts the attention of the caregivers away from the patient and reduces the amount of time a caregiver can devote to patient care. This is particularly true if the documentation process relies on hands-on data entry. For example, data entry to a computing device, such as a tablet, laptop, or other mobile device processing the ePCR may require manual entry via a touchscreen, keyboard, stylus, or another manual data entry device.

Due in part to data reporting format and/or content requirements for ePCRs, such as, for example, NEMSIS (National Emergency Medical Services Information) or HL7 (Health Level Seven International), EMS and/or other medical professionals often spend a significant amount of time documenting their patient encounters. In various implementations, the ePCR may include 50-1000 fields for which a data entry is required (e.g., required by laws of a state or another jurisdiction and/or required for adherence to a data collection standard such as NEMSIS). Since the user cannot reduce or customize the number of data entry fields, the accuracy and completeness of the ePCR may improve as a result of automated filling of at least a portion of these fields. The voluminous number of required fields may cause users to skip or rush through these fields, particularly in the context of an emergency response. However, skipped, inaccurate, and/or incomplete data entry may negatively affect patient care and patient outcomes.

NEMSIS is an example of an official EMS data collection standard for EMS agencies which allows transfer of data between systems and provides a national EMS repository for reporting and research. NEMSIS provides consistent definitions of data elements used in EMS and other pre-hospital care settings. The NEMSIS data collection via NEMSIS-compliant ePCRs may enable analysis of this data for evaluation of and evidence based improvements in patient care across an array of EMS agencies. In particular, the NEMSIS-compliant ePCRs conform to a structured XML standard for the ePCR data. NEMSIS and the XML standard are examples only and other formats and/or content requirements are within the scope of this disclosure. Governments and/or other authorities or agencies may also require various data content for an ePCR. Many of the required fields may be irrelevant to a particular emergency encounter and/or may include the same information for the particular emergency encounter regardless of the patient. Excessive time spent documenting data may contribute to a frustrating user experience for the caregiver and/or a degradation in the care provided to patients.

As a further complexity, some documentations and data reporting format and/or content requirements for electronic patient charting by emergency response agencies include 50-1000 data entry fields. The NEMSIS (National Emergency Medical Services Information) compliant format predominant in the United States provides an example of such a documentation requirement. Completion of such a lengthy form may further consume the time of caregivers at the expense of patient care. Additionally, the voluminous number of required fields may cause users to skip or rush through these fields, particularly in the context of an emergency response. However, skipped, inaccurate, and/or incomplete data entry may negatively affect patient care and patient outcomes. For example, hospital care that follows EMS encounter may lose efficacy without a complete record of treatments and patient conditions during the EMS encounter. Also, the data fields may provide care guidance to the EMS caregivers and may enable EMS agency analytics that drive EMS training and improvements. Additionally, the incomplete ePCR reduces the ability for EMS agencies to generate accurate and timely billing. Thus, overall, excessive time requirements for ePCR documentation contribute to a frustrating user experience for the caregiver and/or a degradation in the care provided to patients.

NEMSIS is an example of an official EMS data collection standard for EMS agencies which allows transfer of data between systems and provides a national EMS repository for reporting and research. NEMSIS provides consistent definitions of data elements used in EMS and other pre-hospital care settings. The NEMSIS data collection via NEMSIS-compliant ePCRs may enable analysis of this data for evaluation of and evidence based improvements in patient care across an array of EMS agencies. In particular, the NEMSIS-compliant ePCRs conform to a structured XML standard for the ePCR data. NEMSIS and the XML standard are examples only and other formats and/or content requirements are within the scope of this disclosure. Governments and/or other authorities or agencies may also require various data content for an ePCR. Many of the required fields may be irrelevant to a particular emergency encounter and/or may include the same information for the particular emergency encounter regardless of the patient. Excessive time spent documenting data may contribute to a frustrating user experience for the caregiver and/or a degradation in the care provided to patients.

The ePCR may include multiple data set sections that cover various aspects of the documentation of an emergency encounter. These data set section may include, for example, data sets for airway, cardiac arrest, EMS crew, medical device, dispatch, patient disposition, patient examination, patient history, injury, laboratory results, and medications. There may be also be custom configurations and sections. As an example, a patient history section may include the data fields indicated below in Table 1. Examples of field values for the data fields are also provided in Table 1. The data field values may be associated with an ICD code (e.g., International Classification of Diseases) for billing purposes.

TABLE 1

| Data field | Field value |
| --- | --- |
| Last name of Patient's Practitioner | Smith |
| First name of Patient's Practitioner | Chris |
| Advance Directives | none |
| Medication Allergies | Penicillin |
| Environmental/Food Allergies | Peanut |
| Medical/Surgical History | Type 2 diabetes |
| Medical History Obtained From | Patient's husband |
| Patient's Immunization | Flu |
| Immunization Year | Current year |
| Current Medications | Metformin |
| Current Medication Dose | 500 |
| Current Medication Dosage Unit | mg |
| Current Medication Administration | Oral |
| Alcohol/Drug Use | none |
| Pregnancy | yes |
| Last Oral Intake | none |

As another example of ePCR data, Table 2 below shows examples of data fields and data field values for ePCR documentation of a pre-scheduled dialysis transport.

TABLE 2

| Data field | Field value |
| --- | --- |
| Call Source | Phone call |
| Dispatch Center | Verifast EMS Services |
| Run Number | 47 |
| Incident Number | 56-87 |
| Dispatched Complaint | Palliative Care |
| Patient Acuity at Dispatch | Priority 4 (Non-Acute) |
| Changed Priority | Pre-Scheduled |
| Trauma call type | Medical and trauma |
| Call type | BLS |
| Response Mode | Pre-Scheduled |
| Additional Response Mode | No lights or Sirens |
| Pickup Zone | 16 |
| Response Delay | None |
| Type of Service | Interfacility transport |
| Patient Disposition | Treated & transported |

Referring to FIG. 1A, an example of a manually populated ePCR is shown. The computing device 10 may provide a user interface 20 for a charting application. For a complete ePCR, the charting application may allow the user to walk through the multiple pages 30 of the ePCR. A selection of a page (e.g., the neuro/airway page 40) may display multiple data categories 45 each with a drop down menu control 48 or another control that allows a display of the information needed for the data category. For example, the selection of "coma scale" 70 drops down the menu 80 with subcategories for coma scale. Each category and/or subcategory may correspond to one or more data fields that each require entry of a field value. For example, the category of coma scale corresponds to the data fields of "eye opening," "verbal," and "motor." The data field "eye opening" requires a field value of "spontaneous," "to sound," "to pressure," or "none" with "to sound" selected in this example. Similarly, the data field of "verbal" requires a field value of "orientated," "confused," "words," "sounds," or "none" with "words" selected in this example. The selection of "motor/sensory" 50 drops down the menu 60 with subcategories for motor/sensory. Each of the subcategories "left arm," "right arm," "left leg," and "right leg" is a data field that requires entry of a data field value. The Tables 1 and 2 show above show examples of data fields and field values specific to the particular categories of patient history and dialysis transport. In order to complete the ePCR, the user may need to step through all or most of the categories and subcategories and enter data field values for all of the data fields in these categories and subcategories. The total number of required data field values may be on the order of 50-1000 as discussed above. Thus the manual population of the ePCR becomes an onerous task that takes the caregiver's attention and hands away from patient treatment and evaluation.

In light of these issues, an automated ePCR data capture system may provide accurate and hands-free contemporaneous ePCR data capture during the patient encounter without the reductions in data accuracy and efficacy of care as discussed above. Unlike data entered after completion of a patient encounter, the contemporaneous data entry reduces or eliminates data entry errors and/or the amount of missing required information (e.g., based on a data entry standard such as NEMSIS) for a particular call type or protocol. Furthermore, such a system eliminates the need for caregivers to divert time and attention away from patient care for the purpose of documentation. For example, medics can use their hands to take a pulse, inject drugs, and apply CPR rather than take notes on a glove or hold and enter data into a computer tablet. This automated system minimizes, and in some instances, eliminates manual human interference in data capture for the ePCR. The automated data capture may occur, for example, via wearable user interface devices, such as earpieces, watches, and/or glasses, that enable data capture from the caregiver via speech recognition and/or augmented reality gestures. Additionally, the ePCR computing device (i.e., the computing device managing the automated ePCR data capture and executing the ePCR software) may communicate with other on-scene devices and/or remote devices. These other devices may transmit or otherwise provide information relevant to the patient encounter directly to the ePCR computing device via device-to-device and/or network communications. The automated data capture based on device communications may further increase the accuracy and efficiency of documentation. For example, these other devices may include medical devices used to monitor and/or treat the patient, a computer aided dispatch (CAD) server or platform, medical record database server(s), and/or location devices, such as GPS or other navigation devices. The location devices may enable the ePCR computing device to utilize location data to provide automatic recording of, for example, elapsed times and estimated times of arrival at a patient or hospital.

The automated ePCR data capture system may not only provide the advantage of automated data capture, but may leverage this automation to provide an advantage of caregiver assistance in real-time based on the captured data. For example, the automated ePCR data capture system may monitor the ePCR form and solicit or query for missing data from caregivers and/or or other devices and/or may infer missing data field values from previously captured values. As another example the automated ePCR data capture system may provide clinical guidance such as caregiver prompts, reminders, and/or alerts as determined by the ePCR computing device. With the automated data collection system described herein, such assistance is available as just-in-time information, for example, immediate alerts to critical changes in patient vital signs. The system may provide the clinical guidance via audio instructions and/or augmented reality images.

As yet another advantage, the automated data capture may enable a pit-crew approach to data entry by an EMS team. In other words, the automated data capture enables a divide and conquer approach. For example, all EMS team members can provide data directly to a central automated ePCR system rather than relaying information to a team member assigned to manual entry of data to the ePCR. The automated system may thus remove the need for a designated team member to devote time to merely recording data rather than providing patient care. Further, as each member of an EMS team provides the data to the ePCR, the other members may be alerted as the ePCR system captures data. These alerts may provide timely updates on patient status and possibly lifesaving information by relaying documented critical changes in a patient condition or critical elements of a patient's medical history (e.g., allergies and/or medications and contraindications thereof). Additionally, the information provided to the individual team members may be tailored to their specific roles thereby reducing or eliminating extraneous and/or irrelevant information for that particular caregiver. This may reduce caregiver distraction and confusion and improve their efficiency and ability to provide efficacious patient care. For example, an EMS team member preparing a transport gurney may need to know about critical skeletal issues documented by a team member examining the victim but may not need to know about the victim's prescription medication history.

Figure 1B:
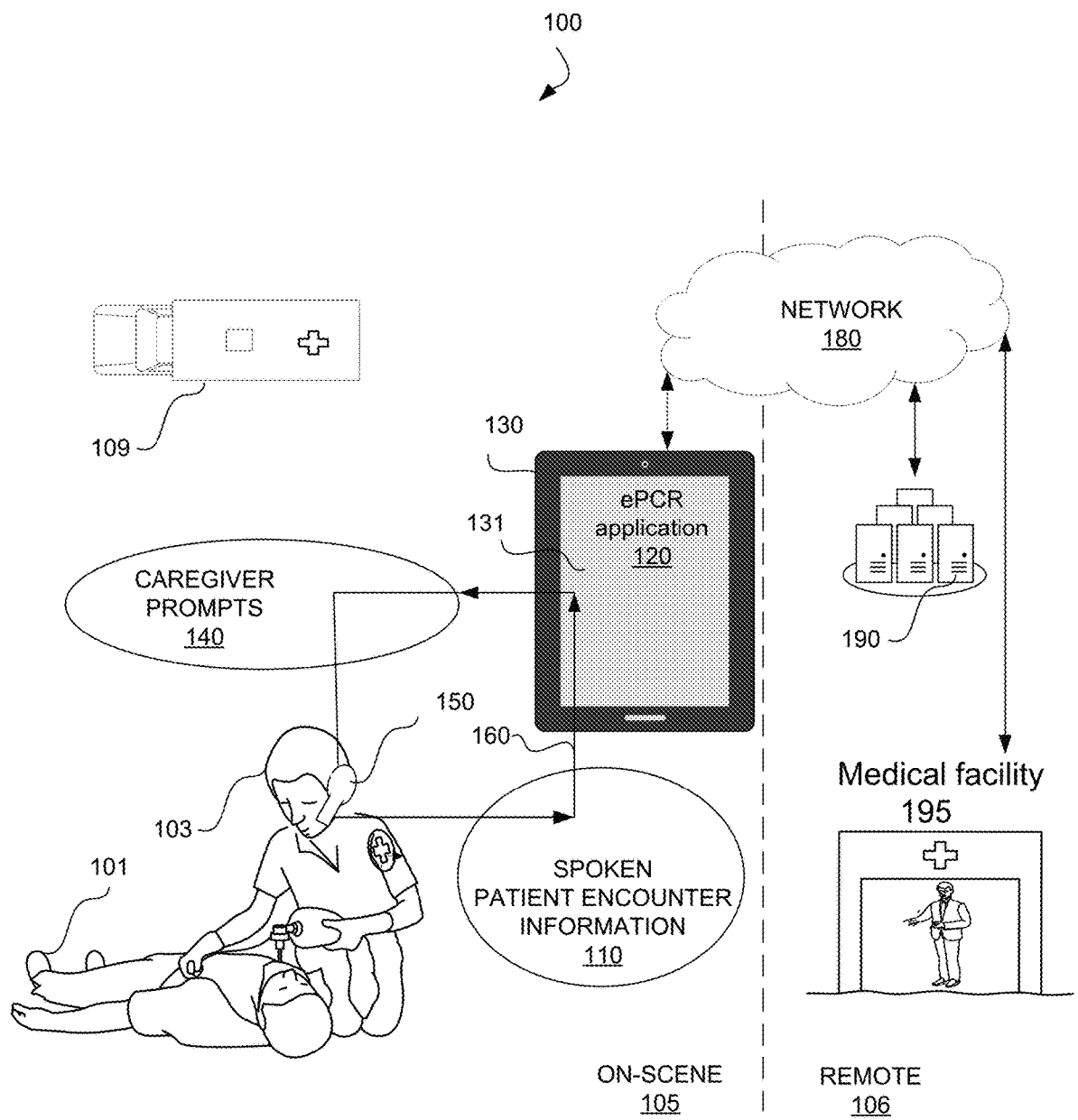
FIGS. 1B and 1C show schematic illustrations of an example of a patient data charting system with automated ePCR data capture and caregiver prompting.
Figure 10:
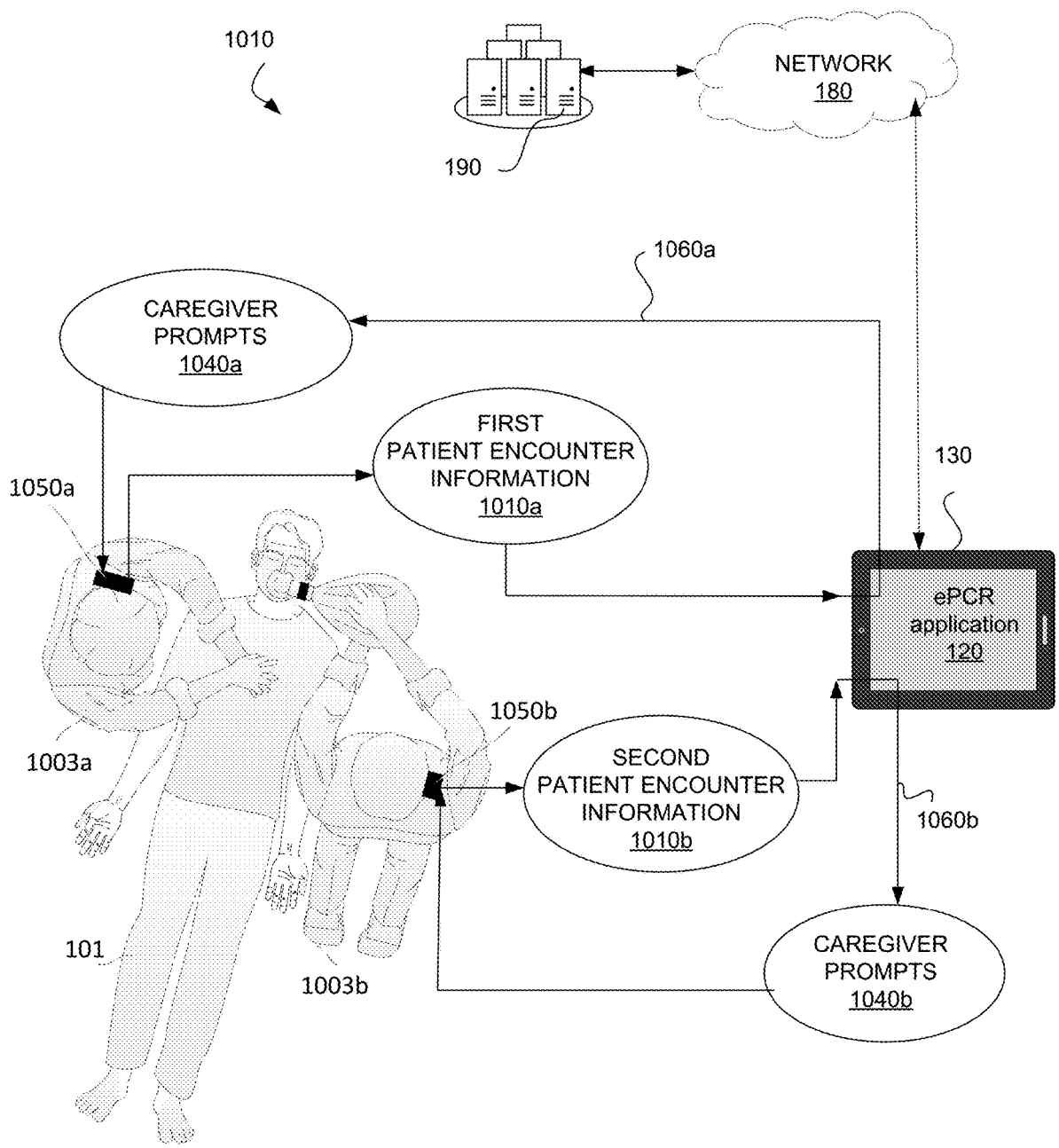
FIG. 10 shows an example of a patient data charting system with automated ePCR data capture and caregiver prompting.

Referring to FIG. 1B, an example of a patient data charting system with automated ePCR data capture and caregiver prompting is shown. In the system 100, a caregiver 103 is shown treating a patient or victim 101. The caregiver 103 may be, for example, an emergency caregiver such as, for example, but not limited to, an emergency medical technician (EMT), a paramedic, an emergency services volunteer, a firefighter, a first responder, a physician, a nurse, etc. Although the system 100 shows a single caregiver 103, the caregiver 103 may be part of team of two or more caregivers (for example, the plurality of caregivers 1003*a* and 1003*b* as shown in FIG. 10). The patient 101 may be a victim of a medical event, which may be, for example, an emergency medical event or a scheduled EMS transport. The caregiver 103 and the patient 101 are co-located on-scene 105 at the site of the patient's medical event. Additionally, the caregiver 103 may be associated with an emergency vehicle 109, for example, an ambulance or a fire truck, also located on-scene 105. The caregiver 103 may also be associated with a mobile computing device 130, for example, a laptop computer, a computer tablet, a smartphone, etc. The mobile computing device 130 may include an electronic patient care record (ePCR) application 120.

In the illustrative scenario of a crew of emergency medical services (EMS) caregivers in an ambulance being called upon to pick up and treat a patient suffering from an emergency medical condition (e.g., a heart attack, or a traumatic injury) and to deliver the patient to a treating hospital the EMS caregivers need to enter patient charting information during the course of the emergency encounter. This patient charting information may comprise information regarding the patient, such as observed patient symptoms during the encounter, observed patient physiological parameters (such as heart rate, ECG traces, temperature, blood-oxygen data, and the like), and treatments or medications administered during the encounter. The patient charting information may include information, such as any known allergies to medication, relevant medical history, and/or additional patient medical conditions. This patient charting information may also comprise information regarding the emergency medical event, such as type of service requested, response mode, and triage classification.

The mobile computing device 130 may include a user input device (shown here, for example, as a touchscreen 131) configured for entry of ePCR information requiring hands-on manual data entry by the caregiver 103. This type of information entry likely requires the caregiver 103 to use their hands to enter information instead of using their hands to treat the patient 101. Additionally, this type of information entry diverts the caregiver's visual attention away from the patient 101 and towards the mobile computing device 130. Therefore, such information entry may adversely affect the quality and duration of care provided to the patient 101 by the caregiver 103. As an alternative, the caregiver 103 may utilize a hands-free wearable user interface device for automated data capture.

In an implementation, the wearable user interface device may be an earpiece 150. The earpiece 150 may include a speaker and a microphone (e.g., the speaker 152 and the microphone 154 shown in FIG. 1C). In an implementation, the earpiece may further include a haptic output device 158.

The wearable user interface device, for example the earpiece 150, and the mobile computing device 130 may be communicatively coupled. In an implementation, the caregiver 103 may speak about the patient encounter, the microphone 154 may capture this spoken patient encounter information 110, and provide this information to the mobile computing device 130 via this wireless communicative coupling 160.

The mobile computing device 130 and/or a computing device 190 located at a remote location 106 and communicatively coupled to the mobile computing device 130 via a network 180 may convert the spoken patient encounter information 110 to text patient encounter information. The network 180 may be a computer network (e.g., an Internet protocol network), a cellular communications network, or a combination thereof. The mobile computing device 130 may execute an ePCR application configured for automated ePCR data capture. Via this application, the mobile computing device 130 may store the text in an appropriate data field of a stored ePCR. Further, based on this patient encounter information, the ePCR application 120 may determine one or more audible caregiver prompts 140 and provide those to the caregiver 103 via the wireless communicative coupling 160 and the wearable device, for example, the earpiece 150.

Figure 1C:
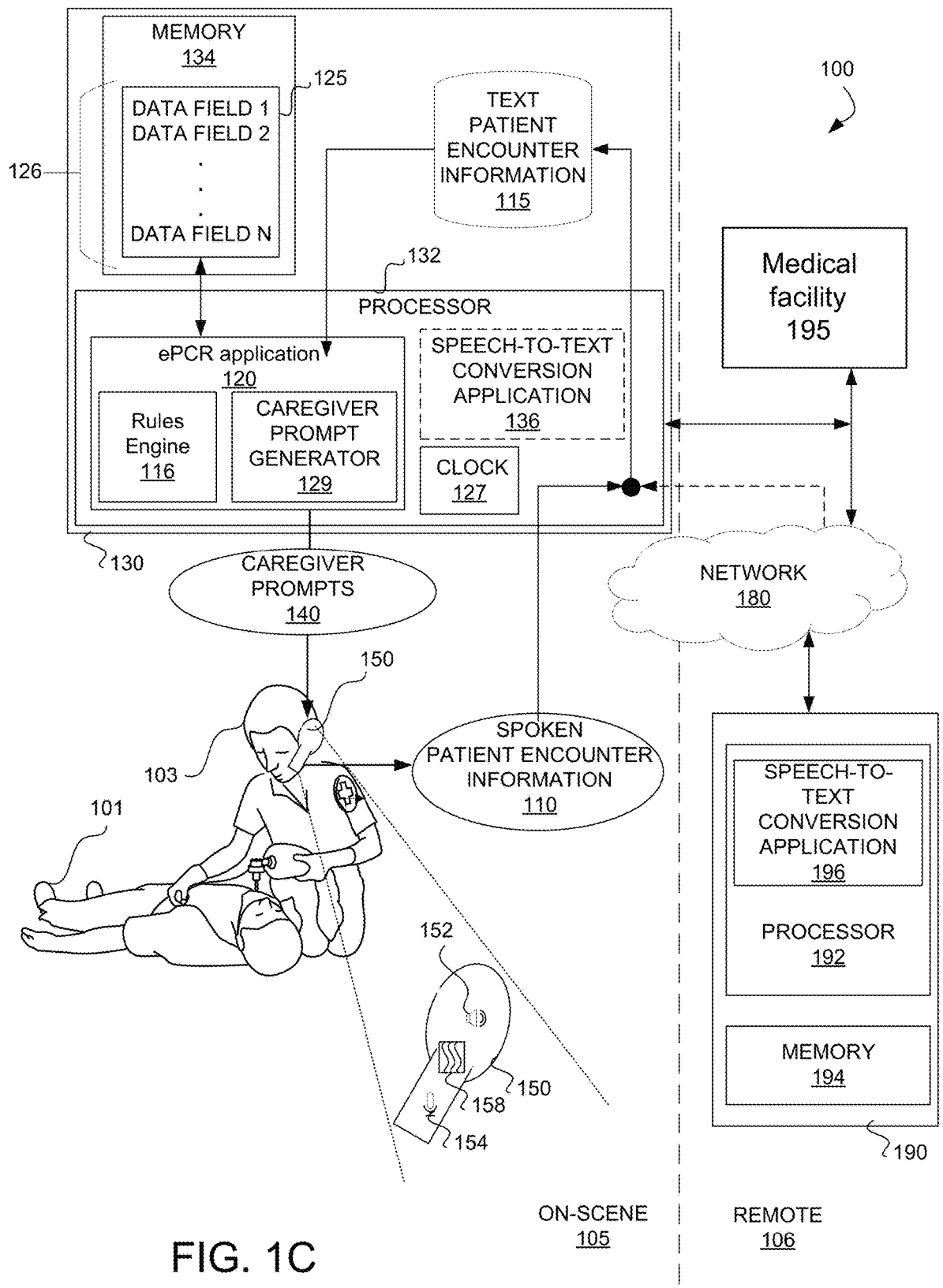

Referring to FIG. 1C, the system 100 illustrated schematically in FIG. 1B is shown in further detail. As discussed above, the earpiece 150 is shown with a speaker 152 and a microphone 154 configured to provide and receive, respectively, audible information to and from the caregiver 103. In an implementation, the speaker 152 is configured to supplement or augment sounds normally heard by the caregiver 103. Accordingly, the speaker 152 may not be "noise cancelling" and may be positioned a distance away from the caregiver's ears so as not to entirely disrupt the caregiver's ability to hear sounds (e.g., speech of other caregivers, audible alerts generated by other devices, environmental sounds, such as sounds indicative of dangerous situations) at the rescue scene. Another option is "transparent" mode like on ear pieces that block of certain kinds of noise but allow through speech, such that voice sounds are clear but things such as constant ambient noise like fans, road noise, airplane engines, and traffic noise are suppressed.

In an implementation, the mobile computing device 130 receives the spoken patient encounter information 110 from the wearable user interface device 150. In an implementation, the processor 132 of the mobile computing device 130 is configured to execute a speech recognition system, for example, a speech-to-text conversion application 136 that resides on the mobile computing device 130. Additionally or alternatively, the mobile computing device 130 is configured to provide the spoken patient encounter information 110 to a remote computing device 190. The remote computing device 190 may include a processor 192, a memory 194, and a speech recognition system, for example, a speech-to-text conversion application 196 that resides on the remote computing device 190. The processor 192 may include a clock 127 configured to provide a current clock time. In an implementation, the mobile computing device 130 may lack the processing capacity to provide the speech-to-text conversion locally without supplemental processing provided by the remote computing device 190. In an implementation, the mobile computing device 130 may rely on the remote computing device 190 for all of the speech-to-text conversion capabilities.

In an example, the audio files may be sent to the speech-to-text conversion application 136 or 196. The speech-to-text conversion application 136 and/or 196 may be a third party speech-to-text engine. Such an engine or service may provide an application programming interface (API) and the ePCR application 120 may use the API to send audio files to the third party conversion service and to receive the converted text files from the third party conversion service. The ePCR application 120 may stream the audio files (e.g., formats such as, for example, MP3, FLAC, LINEAR16, MULAW, AMR, etc.) in real-time to the speech-to-text conversion service. The speech-to-text conversion service may convert the streamed audio files to text in real-time (e.g., during the emergency encounter) and send parseable discrete data back to the ePCR application 120. The speech-to-text conversion service may utilize machine learning and artificial intelligence algorithms to recognize the speech in the audio files as corresponding text.

The speech-to-text conversion service may receive the audio files and return text strings to the computing device 130 and the ePCR application 120. In some examples, if the ePCR application 120 records the audio in a narration mode such as when taking a patient history, the speech-to-text engine may utilize a transcription model for audio that does not fit the other audio models, like long-form audio or dictation. In an implementation, the ePCR application 120 and the computing device 130 may record the audio as high-fidelity, recorded at a 16 kHz or greater sampling rate to improve conversion accuracy.

In an implementation, the speech-to-text conversion service and the ePCR application 120 may utilize a narration mode, or natural language mode, in which the ePCR application 120 may populate the text strings returned by the speech-to-text engine directly into the ePCR data fields (e.g., the various data fields discussed above with regard to Table 1, Table 2, and FIG. 1A). Additionally or alternatively, the speech-to-text conversion service and the ePCR application 120 may utilize a "command and search" mode. In this mode, the ePCR application 120 may recognize various short or single-word utterances as specific voice commands. In an implementation, the voice commands may indicate labels of data fields and the ePCR application 120 may select particular data fields based on these voice commands. For example, one of the voice commands "Select Patient Age 68", or "Patient Age 68", or "Patient Age is 68", or "Male Age 68" may cause the ePCR application 120 to open the specific data fields of "patient age" and "gender" and enter data field values of "68" and "male." In an implementation, the ePCR application 120 may also recognize voice commands as instructions for the ePCR application to perform an action, for example "open patient information page," "pulldown menu," "enter value," etc. As other examples, the voice commands may indicate a section of the ePCR such as, for example, "demographics," "medical history," "dispatch," "patient assessment," "neuro/airway," "respiratory/cardiac," "medications," "labs and fluids," "activity log," or "narrative." Further the voice commands may correspond to specific sub-categories and/or data fields. The ePCR application 120 may locate the data field based on the voice command and then query the caregiver for a data field value, provide a menu either audibly or on a visual display, and/or parse the data field value from a speech string that includes the voice command.

In an implementation, the ePCR application 120 may utilize a speech adaptation mode of the speech-to-text conversion service to recognize particular audio sounds as words specific to the EMS application (e.g., bias the speech recognition to certain text words, for example, to recognize homophones or other easily confused words). For example, the speech adaptation mode may include an instruction to convert the homophonic sounds of "write" and "right" to the text "right" or convert the homophonic sounds of "week" and "weak" to the text "weak," for example, to describe a patient's condition and/or body. The ePCR application 120 may also provide the speech-to-text conversion service with words used frequently within EMS but infrequently outside of EMS to ensure proper recognition and conversion. As another example, the speech adaptation mode may recognize specific words or phrases in the context of EMS and medical terminology. For example, if a caregiver characterizes a victim as "apneic" the speech adaptation mode may recognize this word as a medical term applied to persons suffering from a cessation of breath due to a variety of emergency conditions rather than a chronic condition of "apnea." These words sound similar but "apneic" is the more accurate interpretation for an emergency medical chart than "apnea."

The processor 132 of the mobile computing device 130 may provide text patient encounter information 115 (e.g., received from the local speech-to-text conversion application 136 and/or the remote speech-to-text conversion application 196) to the ePCR application 120. The ePCR application 120 as executed by the processor 132 may enable automated data capture for a stored ePCR 125. The ePCR application 120 may store the patient encounter information in an appropriate data field 126 (e.g., one of Data Field 1, Data Field 2, . . . , Data Field N) of the stored ePCR 125 (e.g., stored in the memory 134 of the mobile computing device 130). The patient encounter information may be an ePCR data field value and may include one or more words, one or more numbers, or combinations thereof. The ePCR application 120 as executed by the processor 132 may further enable automated caregiver prompting based on the automated data capture. For example, based on the patient encounter information (e.g., the spoken information 110 converted to text information 115) provided to the ePCR application 120, an audible caregiver prompt generator 129 of the ePCR application 120 may generate and provide audible caregiver prompts 140 to the wearable device, for example, the earpiece 150. In this example, the speaker 152 of the earpiece 150 may provide the prompts 140 to the caregiver 103 as audible information.

The ePCR application 120 may also include a rules engine 116. The rules engine 116 may apply rules to first data fields and/or data field values in order to infer data field values for second data fields. Application of the rules by the rules engine 116 may also trigger reminders and/or alarms for the caregiver 103 based on the data field values. The ePCR application 120 may include rules based on physiological facts (e.g., pregnant=female and/or pregnant male), medical treatment protocols, and/or machine learning. For example, the medical treatment protocols may specify specific transport conditions for trauma or specific examination procedures for a bleeding head wound. The rules engine may automatically populate data field values based on these conditions or procedures and/or may generate reminders for care in response to data field values indicative of these conditions. Further examples of the rules engine 116 are provided below. The rules engine 116 may also function as a data validation engine.

In an implementation, the system 100 may include a medical facility 195 communicatively coupled to the computing device 130 via the network 180. The processor 132 and ePCR application 120 may provide and/or receive information to and/or from the medical facility 195 (e.g., a server, mobile device, computing device, and/or terminal at the medical facility). In an implementation, the medical facility 195 may be a pre-selected medical facility, may be a medical facility selected by the caregiver 103 and input to the ePCR application 120 during the patient encounter. Additionally or alternatively, the location device 310 discussed below with regard to FIG. 3A may select a medical facility based on geographic proximity and/or caregiver confirmation.

Figure 1D:
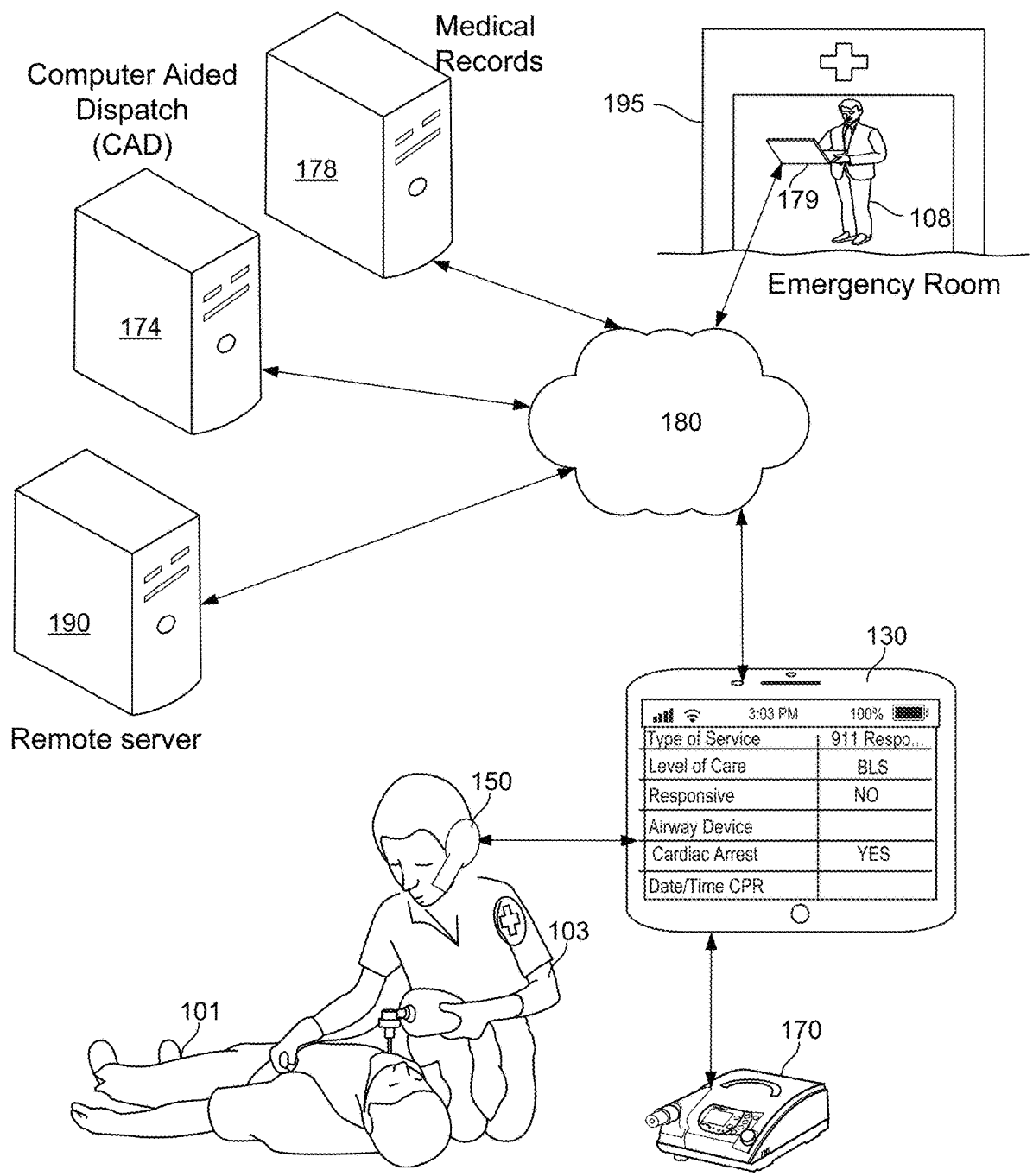
FIG. 1D shows examples of communicative couplings between a computing device hosting the ePCR application and external computing devices.

Referring to FIG. 1D, examples of communicative couplings between a computing device hosting the ePCR application and external computing devices are shown schematically. In various implementations, the mobile computing device 130 may send and/or receive information from one or more external communicatively coupled devices in addition or as an alternative to the wearable user interface device 150. The external devices may include one or more medical devices 170, as described in further detail with regard to FIGS. 8 and 9. Additionally or alternatively, the computing device 130 may be configured to communicatively couple, via the network 180 (e.g., as discussed in FIG. 1C) to one or more of the remote server(s) 190 (e.g., as discussed in FIG. 1C), computer aided dispatch (CAD) server(s) 174, medical records server(s) 178, and/or one or more computing devices 179 associated with a medical facility 195. In an implementation, the computing device(s) 179 may be associated with remotely located medical personnel 108. The ePCR application 120 may populate one or more data field values based on patient and/or emergency event information received from the CAD server(s) 174, the medical record server(s) 178 and/or the computing device(s) 179. The CAD server(s) 174 may provide EMS dispatch information. The EMS dispatch information may include a time and location of the emergency event, demographic information for the patient, EMS crew information, chief complaint information, patient transport information, etc. The EMS dispatch information may include a delay time between a 911 call and the dispatch of an emergency crew, a time of the 911 call, and a time of the dispatch of the emergency crew. The location of the emergency event may include a longitude and latitude and may include a third dimension to indicate a floor of a multi-story building. The EMS dispatch information may further include records of dispatcher based triage. The dispatcher may direct triage tasks by bystanders prior to the arrival of an emergency crew and these tasks may correspond to data fields of the ePCR. The medical records server(s) 178 may provide medical records database information such as, for example, medical history information for the patient. The medical history information may include medications, chronic conditions, physician information, historical treatment information, etc.

Figure 2A:
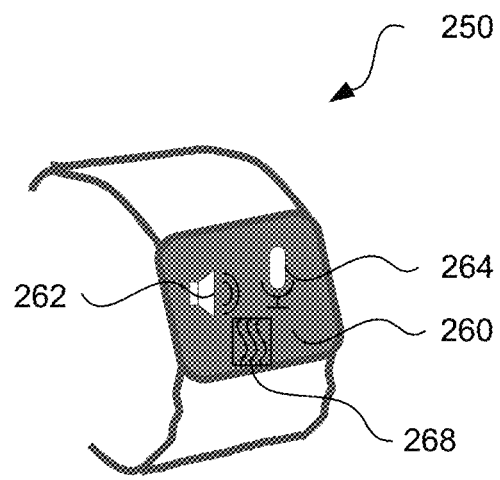
FIGS. 2A and 2B show examples of wearable user interface devices.
Figure 2B:
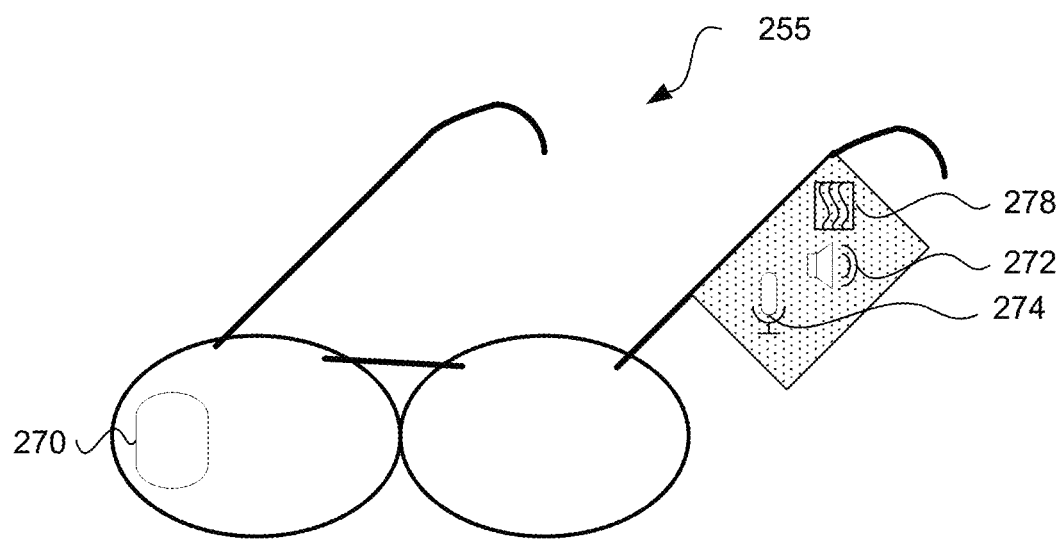

Referring to FIGS. 2A and 2B, additional examples of wearable user interface devices are shown schematically. In addition to or as an alternative to the earpiece 150 shown in FIGS. 1B and 1C, the wearable user interface device may be a watch 250. The watch 250 may include a display 260, a speaker 262, and a microphone 264. As another example, the wearable user interface device may be augmented reality (AR) glasses 255. The AR glasses 255 may include a speaker 272 and a microphone 274. In an implementation, the speaker 272 is configured to supplement or augment sounds normally heard by the caregiver 103. Accordingly, the speaker 272 may not be "noise cancelling" and may be positioned a distance away from the caregiver's ears so as not to entirely disrupt the caregiver's ability to hear sounds (e.g., speech of other caregivers, audible alerts generated by other devices, environmental sounds, such as sounds indicative of dangerous situations) at the rescue scene.

In an implementation, the AR glasses 255 may further include a display 270. The display 270 may be an augmented reality display as discussed in more detail with regard to FIG. 14. The watch 250 and/or the AR glasses 255 may include a haptic output device (e.g., the haptic devices 268 and 278). The haptic devices 268 and/or 278 (e.g., vibration motors) may be configured to provide vibration feedback to the caregiver 103. The haptic devices 268 and/or 278 may be configured to emit various patterns and intensities of vibration to convey information to the caregiver 103. For example, the haptic devices 268 and/or 278 may be compact linear actuators that vibrate at varying patterns and intensities as directed by, for example, the processor 132 and/or a processor associated with the watch 250 and/or the AR glasses 255. Such an actuator may include a spring and magnet for manipulating a mass coupled thereto. In some instances, providing vibration feedback, rather than audio alerts and/or visual indicators, may be less likely to distract other caregivers 103 from resuscitation activities they are performing. In other examples, the vibration feedback may supplement audio alerts and/or visual indicators or replace the audio alerts in a noisy environment.

In an implementation, the caregiver 103 may use a combination of two or more of the earpiece 150, the watch 250, and the AR glasses 255 to communicate with the mobile computing device 130. Further, in an implementation, the earpiece 150, the watch 250, and/or the AR glasses 255 may be configured to communicatively couple with one another.

Figure 3A:
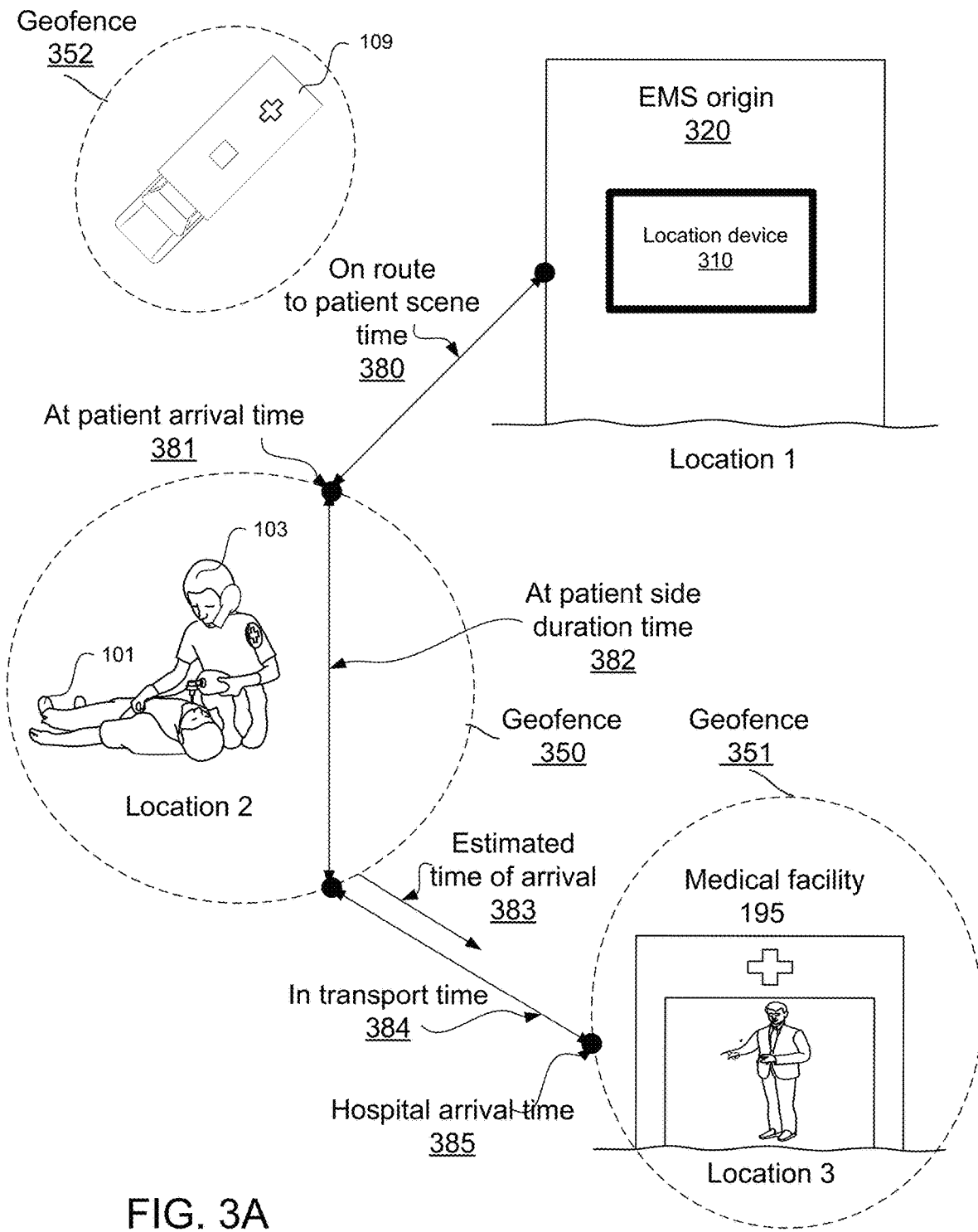
FIGS. 3A, 3B, and 3C show an example of a patient data charting system with automated ePCR data capture and caregiver prompting based in part on location information.
Figure 3B:
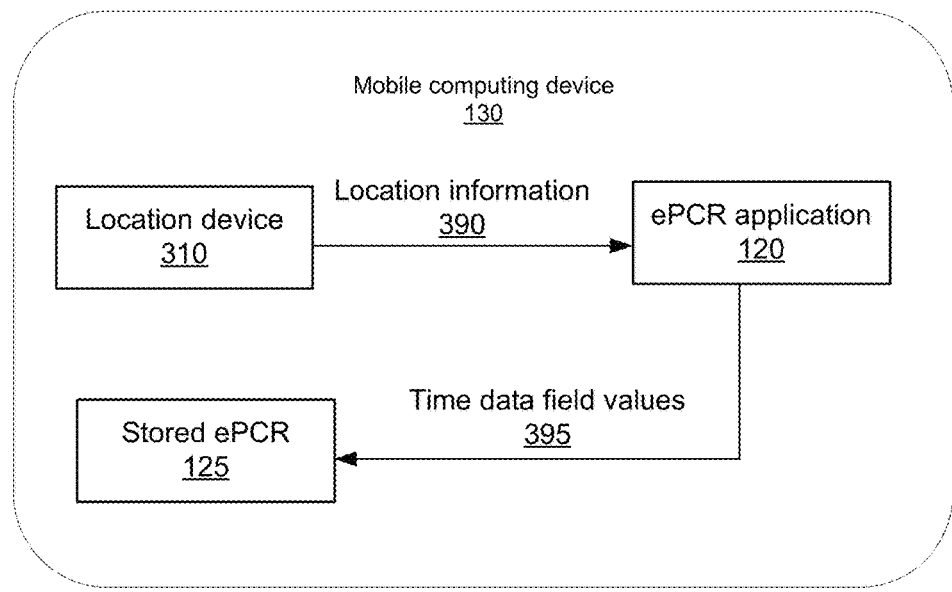
Figure 3C:
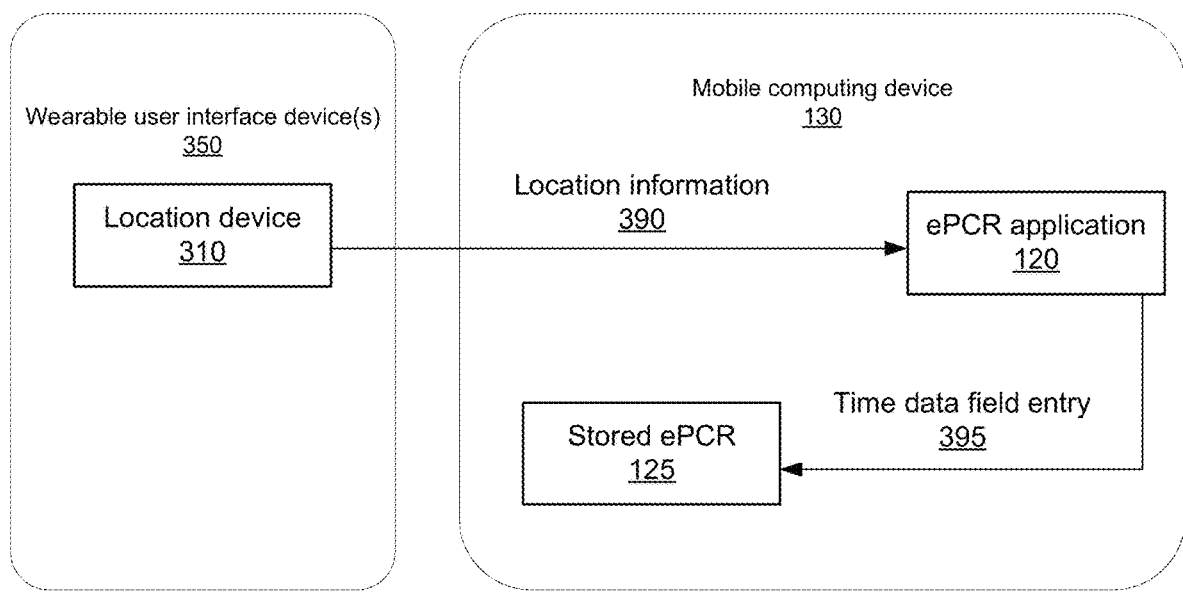

Referring to FIGS. 3A, 3B, and 3C, an example of a patient data charting system with automated ePCR data capture and caregiver prompting based in part on location information is shown. In an implementation, the system 100 (e.g., as shown in FIGS. 1B and 1C) may include a location device 310. As illustrated in FIGS. 3B and 3C, one or more of the mobile computing device 130 and the wearable user interface device(s) 350 may include, or host, the location device 310. The wearable user interface device(s) 350 may include one or more of the earpiece 150, the watch 250, and the AR glasses 255. The location device 310 may be, for example, a global positioning system (GPS) device, a wireless communications location device, or a combination thereof. The GPS device may determine location based on GPS satellite signals, the wireless communications location device may determine location based on wireless communication radio signal strength, and the combination may use both types of signals to determine location.

As illustrated schematically in FIGS. 3B and 3C, the location device 310 may determine location information 390 associated with the patient encounter information recorded in the stored ePCR 125. The location device 310 may provide the location information 390 to the ePCR application 120. The ePCR application 120 as executed by the processor 132 may determine one or more time data field values 395 for the stored ePCR 125. The time data field values 395 may be times determined based on the clock 127 and the location information 390. These times may include, for example, but not limited to, an on-route-to-patient-scene time 380, an at-patient-arrival-time 381, an at-patient-side duration time 382, an in-transport time 384, an estimated time of arrival at a hospital 383, and a hospital arrival time 385. This automated time determination and data entry relieves the caregiver 103 from noting times, calculating times, and entering times into the stored ePCR 125. As illustrated in FIG. 3B, the location device 310, the ePCR application 120 and the stored ePCR 125 may all reside on the mobile computing device 130. In an implementation, as illustrated in FIG. 3C, the location device 310 may reside on the wearable user interface device 150 associated with the caregiver 103. The location device 310 may provide the location information 390 to the ePCR application 120 that resides on the mobile computing device 130 via a wireless communicative coupling between the wearable user interface device 150 and the mobile computing device 130.

In an implementation, the system 100 may include a plurality of location devices. For example, the wearable user interface device 150 and the mobile computing device 130 may both include location devices 310 that provide location information 390 to the ePCR application 120. In an implementation, a caregiver team may include a plurality of caregivers each with a wearable user interface device and one or more of these interface devices may include a location device 310. The ePCR application 120 as executed by the processor 132 may collect location information 390 from all of the location devices 310. This aggregate of location information may enable the ePCR application 120 to track individual caregivers and share location and time information amongst caregivers on a crew via audible caregiver prompts 140. In an example, a first caregiver on a team may be physically located at the patient 101 and providing manual CPR. A second caregiver on the team may need to locate an AED, retrieve medical supplies from the ambulance and/or attend to another medical duty away from the patient. The ePCR application 120 may use the aggregate location information to update the first caregiver on the location and timing of the second caregiver.

Referring again to FIG. 3A, in an example, the caregiver 103 or a caregiver team may receive dispatch information about a medical event at an EMS origin 320, which may be a first location (e.g., Location 1). The EMS origin 320 may be a fire station or an EMS agency location. The caregiver 103 or caregiver team may travel to the patient 101 in a vehicle, for example, the ambulance 109. The patient location may be a second location (e.g., Location 2). The caregiver 103 or caregiver team may provide treatment at the patient scene and then transport the patient to a hospital or other medical facility 195 at a third location (e.g., Location 3). The location device 310 may record and/or determine coordinates for Location 1, Location 2, and Location 3 along with a time stamp for each location. The location device 310 may provide the coordinates and time stamps in the location information 390 provided to the ePCR application 120. The ePCR application 120 may then determine the time values for data field entries 395 to the stored ePCR 125. Further, the location device 310 may provide a rate of change in location to the ePCR application 120. The ePCR application 120 may use the rate of change to determine an estimated time of arrival 383 at the medical facility 195.

In an implementation, the ePCR application 120 as executed by the processor 132 may determine or establish one or more geofences 350 for use in determining times associated with the patient encounter. In an implementation, the CAD 174 may establish the geofences for use by the ePCR application 120. For example, the ePCR application 120 may receive GPS coordinates for the emergency scene from the CAD 174 and establish a geofence of 100 meters around the GPS coordinates. Once the mobile device 130 crosses the geofence, the ePCR application 120 or a navigation application included in and/or accessible by the ePCR application 120 may measure the rate of movement of the mobile device 130. The ePCR application 120 may record a time on scene based on the length of time that this rate of movement is approximately zero or between 0-10 kph. In an implementation, the ePCR application 120 may store GPS coordinates for one or more medical facilities. Based on an entry of a medical facility destination into the ePCR application 120 and/or the navigation application, the ePCR application 120 may retrieve the GPS coordinates for the medical facility 195 and establish the geofence for the medical facility. In an implementation, the ePCR application 120 and/or the navigation application may track the location of the ambulance, compare this tracked location to a list of medical facilities, and establish a geofence 351 around the medical facility 195 closest to the tracked location of the ambulance 109. If the ambulance 109 moves past this first medical facility, the ePCR application 120 may recalculate the distance to the medical facilities on the list and re-establish a new geofence based on the recalculated distance and updated location of the ambulance 109.

FIG. 3A shows examples of a geofence 350 (e.g., a first geofence) around the victim and a geofence 351 (e.g., a second geofence) around the medical facility 195. For example, the application 120 and/or the CAD 174 may establish the geofences 350 and 351 around the victim 101 and/or the medical facility 195. Based on these geofences, the ePCR application 120 may automatically determine a time that the EMS crew arrived at the emergency scene, a time that the EMS crew left the emergency scene, and/or a time that the EMS crew arrived at the medical facility. In an implementation, the geofence 350 may be a three-dimensional geofence to detect, for example, entry and exit from a floor of a building.

In an implementation, the ePCR application 120 and/or the CAD 174 may establish the geofence 350 around the patient location. Once the mobile device 130 enters this virtual boundary, the ePCR application 120 may automatically trigger an at-patient-scene status and associate all data entries to the stored ePCR 125 with this status. Conversely, once the mobile device leaves the virtual boundary of the geofence, a second timer is started that indicates en route time to the hospital.

In some examples, the ePCR application 120 may start when the mobile device 130 enters the virtual boundary of the geofence. When this third timer reaches a specified threshold, the ePCR application 120 may generate a transport alarm or other indicator to the caregiver to indicate that the caregiver is spending too long at scene and they should be preparing the patient for transport. For instance, trauma victims with gunshot or knife wounds or other exsanguination injuries may respond better with a quick triage type of treatment at scene followed by rapid transport to the medical facility than to a longer and more comprehensive treatment at the scene. The ePCR application 120 may include manually adjusted user settings for timer thresholds or may automatically select the timer threshold based on the type of medical condition being treated (e.g., the chief complaint) or other patient parameter.

In an implementation, the ambulance 109 may include a location device 310 and the ePCR application 120 may establish a geofence 352 around the ambulance 109. In an implementation, one or more of the caregiver 103 and a gurney may include an RFID tag or other type of near-field transceiver, for instance low-power Bluetooth. The caregiver 103 may secure an RFID tag or other near-field transceiver to the patient 101. The ePCR application 120 may recognize the entry of one or more of these RFID tags into the geofence around the ambulance 109 and automatically record a start of patient transport and initiate caregiver prompts associated with patient transport. For example, if the transport timer is below a set threshold when the mobile device 130 enters the virtual boundary around the ambulance, another alarm or indication will go off that indicates that the caregiver is moving the victim to the ambulance too soon. For example, a medical protocol may require 20 minutes of on-scene CPR for a cardiac arrest and the transport alarm may warn the EMS crew that they have provided an insufficient duration of on-scene CPR.

Often, in the time-sensitive environment of EMS, caregivers estimate times after the event, write times on latex gloves, and/or transpose written notes after the event. Caregivers may revert to these and other inaccurate recording methods so that the caregiver 103 can provide necessary medical care without interruption. This automated capture of time data improves the accuracy of these entries and enables the caregiver 103 to maintain focus on the patient 101 without the distraction and burden of recording these times. Additionally, as discussed further below, the ePCR application 120 may provide the at patient side duration time and/or the estimated time of arrival to caregiver(s) in an automated fashion as audible caregiver prompts 140. This may enable the caregiver(s) to adjust medical care based on time (e.g., accelerate movement of patient to the ambulance if time on scene exceeds a desired value, implement supplemental medical care in the ambulance if the estimated time of arrival is longer than expected, etc.) and improve the efficacy of medical care without distraction of the EMS crew.

In some clinical situations such as treating patients with a heart attack (i.e. myocardial infarction) or stroke, the total time duration from EMS arrival at the patient location ("at scene") to the time of delivery of the therapeutic intervention ("door-to-balloon" time or "911-call-to-balloon" time) are critical durations by which to accurately measure as well as utilize in Statistical Process Control or Quality Improvement (SPC, QI) of the medical system. It has been shown in numerous studies that reducing the door-to-balloon time will improve survival rates. However, in order to actualize quality improvement (QI), the whole range of actions and interventions involved in the patient care continuum need to be measured and optimized. For instance, the process from the time of EMS dispatch receiving the 911 call to the time of a patient receiving the therapeutic intervention needs to be broken down into a sequence of individual steps and durations required for each step (e.g. 911 call to arrival at scene; scene to at patient side, at patient side to aspirin or other therapy delivered; at patient side to en route to hospital emergency department (ED); ED to definitive therapy. Breaking down the total duration into smaller segments allows for a more effective QI process to occur on each individual process element. With geofencing and near-field transceivers as discussed above durations for each of the segments of the total duration can be measured and displayed during the event as well as after the fact review of the event for post-event quality assurance/quality improvement (QA/QI). The event can be displayed as a timeline in either graphical or tabular/list form with individual durations for the process segments or sub-segments. Average EMS system performance as well as EMS system performance goals may be displayed alongside the actual measured real-time durations within the ePCR display. Data from other cloud-based applications such as Dispatch and Emergency department intake/EMR/EHR software may be utilized to fill in duration measurements occurring either before the start of ePCR or medical device timers or after arrival at the hospital.

Figure 4:
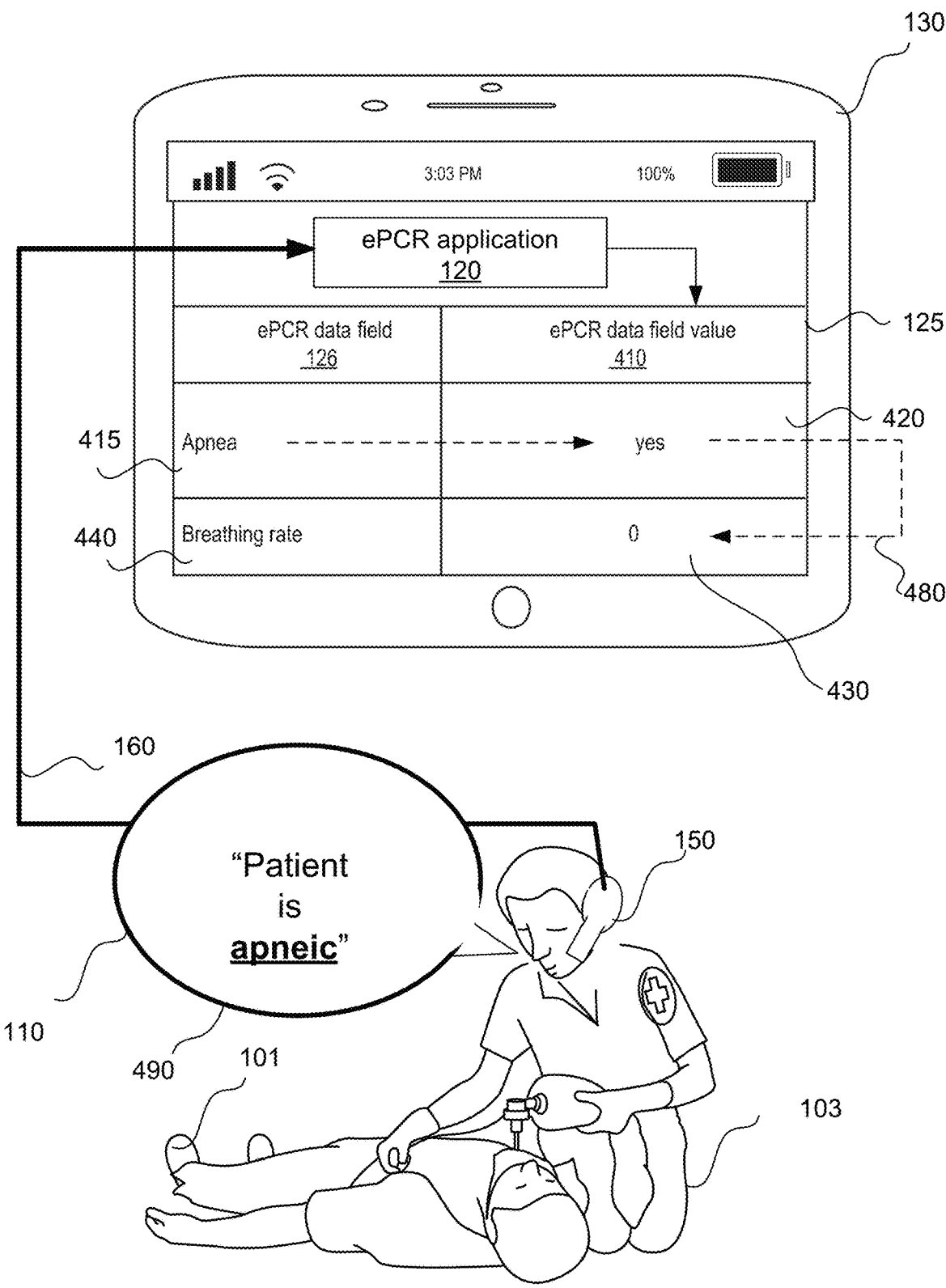
FIG. 4 shows an example of ePCR data fields automatically populated based on key words and/or inference.

Referring to FIG. 4, an example of ePCR data fields automatically populated based on key words and/or inference is shown. In this exemplary illustration, the caregiver 103 associated with a wearable user interface device, the earpiece 150, attends to a victim 101. The caregiver 103 provides spoken patient encounter information 110. The wearable user interface device captures the spoken patient encounter information 110 and provides this information to the ePCR application 120 via a wireless communicative coupling 160 between the wearable user interface device and the mobile computing device 130. In an implementation, the spoken patient encounter information 110 may include one or more predetermined keywords 490. In this example, "apneic" is a predetermined keyword 490. The ePCR application 120 as executed by the processor 132 may provide the captured spoken patient encounter information 110 to a speech-to-text conversion application (e.g., the application 136 and/or 196) and the resulting text patient encounter information 115 may include the same predetermined keyword 490.

The one or more predetermined keywords 490 may correspond to an identifier 415 for an ePCR data field 126. In an implementation, the one or more predetermined keywords 490 may exactly match an ePCR data field identifier 415 or may match a portion or grammatical variant of the ePCR data field identifier 415. For example, in FIG. 4, a portion of the spoken information 110 "Patient is apneic," namely, "apneic" corresponds to the ePCR data field identifier 415 of "Apnea." Further, in this example "apneic" is a grammatical variant of "apnea." In an implementation, the keyword may be a synonym or reference to the ePCR data field identifier 415. The ePCR application 120 may include a look-up table or other synonym or word association or word mapping application that associates keywords 490 with the ePCR data fields 126 and identifiers 415.

In an implementation, the one or more predetermined keywords 490 may include a body part. The ePCR application 120 may identify one or more ePCR data fields 126 based on the body part keyword. The ePCR application 120 may populate the data field 126 with a body part description included in the caregiver speech 110 in conjunction with the body part keyword.

Based on the predetermined keyword 490, the ePCR application 120 is configured to identify the ePCR data field 126 and populate the ePCR data field 126 with the ePCR data field value 410. In the example of FIG. 4, the specific ePCR data field value 420 for the "Apnea" data field 415 is "yes." The ePCR application 120 may determine that the keywords "patient is" correspond to an ePCR data field value 420 of "yes." As another example, the spoken patient encounter information 110 may include the words "blood pressure 130 over 90." The ePCR application 120 may map the predetermined keywords "blood pressure" to an ePCR data field 126 and identify the words "130 over 90" as the ePCR data field value 410 for the blood pressure ePCR data field.

In an implementation, the ePCR application 120 may infer 480 a second ePCR data field value 430 for a second ePCR data field 440 from a first ePCR data field value 420 for a first ePCR data field 415. The ePCR application 120 may include a template, a look-up table, or another correspondence tool that indicates values of one or more second ePCR data fields 440 based on one or more first ePCR data field values. In the example of FIG. 4, the ePCR application 120 infers a data field value of "zero breaths/minute" for the breathing rate data field from the data field value of "yes" for the apnea data field. As another example, the ePCR application 120 may infer a data field value of "not applicable" for one or more second data fields based on data field values for one or more first data fields. For instance, the ePCR application 120 may infer a value of "not applicable" in the data field of "pregnant" based on a value of "male" in the data field of "gender." As further inference examples, in a trauma case, the ePCR application 120 may infer data field values of "no spinal immobilization," "no backboard," and/or "seated" in transport data fields based on values of "mobile," "no pain," and/or "walking" in the observation data field.

In an implementation, the ePCR application 120 may infer data field values based on a vocabulary database and a set of rules applied to the vocabulary database by the rules engine 116 (e.g., as shown in FIG. 1C). In such an implementation, a particular vocabulary word triggers a rule and the rule triggers an action. For example, the vocabulary database may include the word "apneic." The rule for an occurrence of "apneic" in the converted speech of the caregiver may be "set apnea field to yes." Based on this rule, in response to the word "apneic," the ePCR application 120 may enter a value of "yes" in the apnea data field. The vocabulary database may include cross-references for multiple words that correspond to a same data field. For example, "saturation" and "pulse ox" may both point to the "pulse oximetry" data field because "saturation" and "pulse ox" are common phrases used by an EMS crew to refer to "pulse oximetry." The rules engine may further provide for inferred values with a rule for a second data field value based on the value of a first data field. In the "apneic" example, the rule for "apneic" in the converted speech of the caregiver may be "set apnea field to yes and set breathing rate field to 0." Alternatively, the ePCR application 120 may apply rules to specific fields, for example, "if apnea field=yes, the breathing rate field=0" and apply this rule to both the apnea field and the breathing rate field.

In an implementation, the ePCR application 120 may infer data field values according to the rules engine 116 based on one or more medical protocols. The rules engine 116 may associate particular medical observations with data field values for related data fields. For example, a caregiver may record the observations "mobile," "no pain," and "walking" in the ePCR for a trauma victim. The ePCR application 120 may implement the rules engine 116 to infer the values of "no spinal immobilization," "no backboard," and "seated" in the transport data fields of the ePCR based on the recorded observations. These data field values correspond to medical protocols which indicate that a mobile walking patient that is not reporting pain can be transported without spinal immobilization, without a backboard, and in a seated position. The rules engine 116 may also link data fields according to ICD codes applied within the ePCR application 120.

Figure 5A:
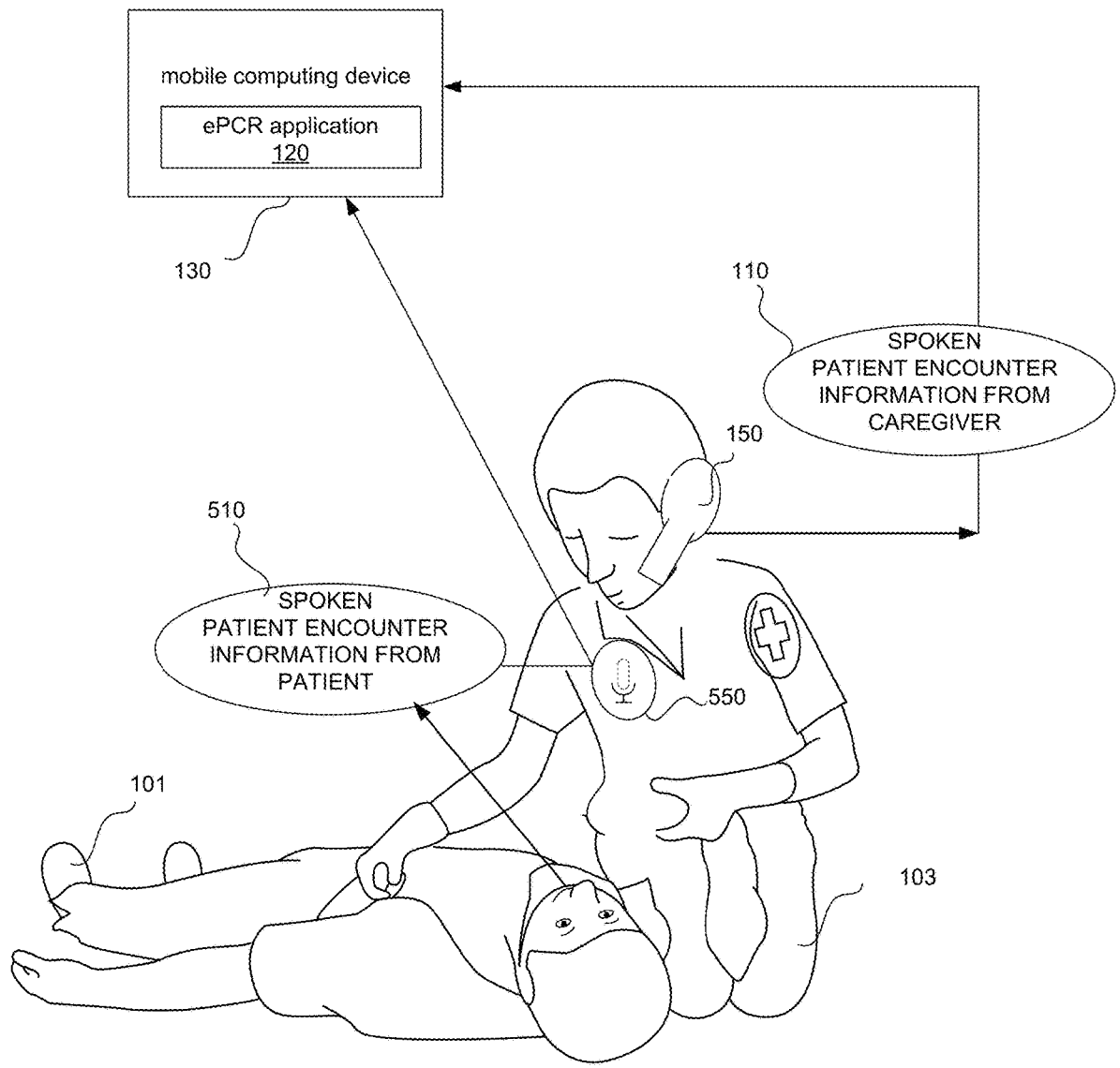
FIG. 5A shows an example of a patient data charting system with automated ePCR data capture and caregiver prompting that includes a patient microphone.

Referring to FIG. 5A, an example of a patient data charting system with automated ePCR data capture and caregiver prompting that includes a patient microphone is illustrated. In an implementation, a patient microphone 550 is configured to capture patient speech 510 preferentially. The patient microphone 550 may be disposed on the caregiver 103, as shown, for example, in FIG. 5A, in a position that preferentially captures patient speech 510 over caregiver speech 110 and ambient noise. The patient microphone 550 may be disposed on a portion of the caregiver's body that is likely to be proximate to the patient's mouth. In an implementation, the caregiver 103 may affix the patient microphone 550 to the patient 101 or to an item of medical equipment on or proximate to the patient to preferentially capture patient speech 510. The microphone 550 and the wearable user interface device, e.g., the earpiece 150, may provide spoken patient encounter information to the mobile computing device 130 via one or more wireless communicative couplings between the devices 150 and 550 and the device 130. In an implementation, the ePCR application 120 as executed by the processor 132 is configured recognize that the spoken patient encounter information includes the patient speech 510 and the caregiver speech 110. Further, the ePCR application 120 may be configured to differentiate between the patient speech 510 and the caregiver speech 110. For example, the ePCR application 120 may differentiate based on whether speech input comes from the first microphone (e.g. the microphone 154 in FIG. 1C) and the earpiece 150 or comes from the second microphone 550. For example, the speech input may include metadata that identifies the device that provides the speech input to the mobile computing device 130. In an implementation, the ePCR application 120 may be configured for voice recognition of the caregiver 103 and may assign speech not recognized as caregiver speech to the patient 101. In an implementation, the ePCR application 120 may use a combination of these methods and/or may determine the source of the speech based on the content of the speech. For example, the ePCR application 120 may associate various keywords with either the caregiver 103 or the patient 101.

Figure 5B:
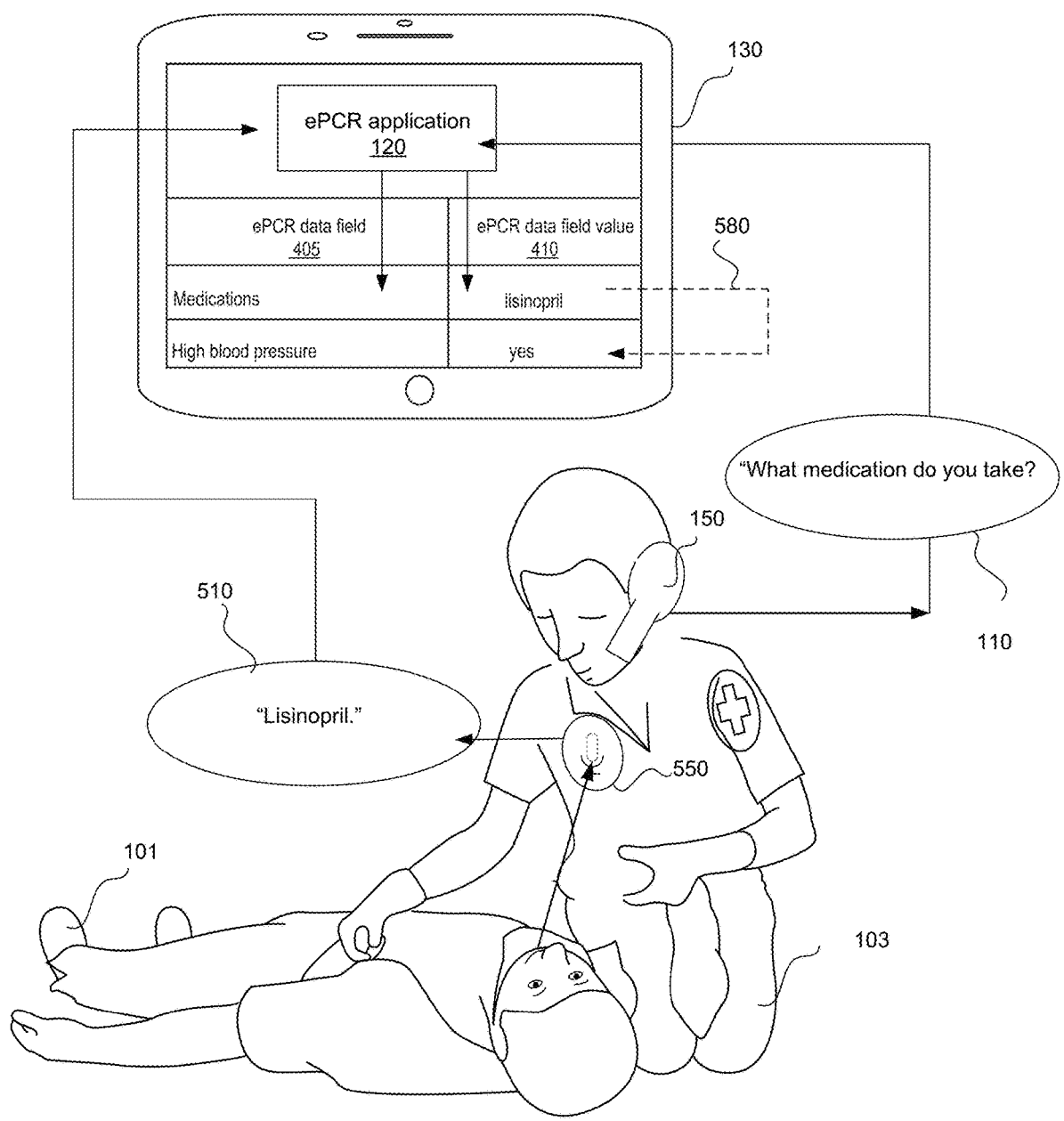
FIG. 5B shows an example of ePCR data fields automatically populated based on key words in caregiver and patient speech.

Referring to FIG. 5B, an example of ePCR data fields automatically populated based on key words in caregiver and patient speech is shown. In an implementation, the ePCR application 120 may populate one of more first ePCR data fields with values based on the caregiver speech 110 and may populate one or more second ePCR data fields with values based on the patient speech 510. In an implementation, the ePCR application 120 may identify one or more ePCR data fields based on the caregiver speech 110 and populate the one or more identified ePCR data fields with values based on the patient speech 510. For example, the caregiver speech 110 may include a question that identifies a data field and the patient speech may include an answer that includes a value for the identified data field.

As a more specific example, the caregiver may ask, "What medications do you take?" In response, the ePCR application 120 may identify the "patient medication" data field 405 based on the caregiver speech 110. The patient may answer, "lisinopril." In response, the ePCR application 120 may enter a data field value 410 of "lisinopril" in the patient medication data field based on the patient speech 510. In an implementation, the ePCR application 120 may identify the data field 405 and the data field value 410 based on the patient speech 510. For example the ePCR application 120 may include a reference table that identifies "lisinopril" as a medication.

Referring further to FIG. 5B, in an implementation, the ePCR application 120 may infer ePCR data field values based on the caregiver speech 110 and/or the patient speech 510. For example, the ePCR application 120 may infer 580 an ePCR data field value of "yes" for the ePCR data field "high blood pressure" based on the data field value of "lisinopril" for the ePCR data field of "medications." The ePCR application 120 may include a template, a look-up table, or another correspondence tool that indicates values of one or more second ePCR data fields and data field values based on one or more first ePCR data fields and data field values.

In an implementation, the ePCR application 120 may utilize a database compiled based on machine learning to correlate medications and conditions. For example, based on historic data, machine learning may indicate a probability that a medication indicates a particular condition. As an example, if this probability is 99% or higher, the ePCR application 120 may automatically infer a data field value for a condition based on entry of a medication. If the probability is between 80-99%, the ePCR application 120 may prompt the caregiver to ask the patient or a bystander or consult a medical record to confirm the condition. In an implementation, the ePCR application 120 may search a victim's medical record as received from a medical record database 178 for the condition and/or the medication. If the probability is below 80%, then the ePCR application 120 may not enter a data field value for that condition.

As another example, the ability of the patient to speak indicates that the patient is verbally responsive. Therefore, the ePCR application 120 can enter a null value (e.g., zero or not applicable or another indicator of an irrelevant data field based on the patient's medical condition) into one or more ePCR data fields that are incompatible with a verbally responsive patient. As a more specific example, the stored ePCR 125 may include a cardiac arrest data section for information about a patient in cardiac arrest. However, a cardiac arrest patient will not be verbally responsive. Therefore, in response to patient speech 510, the ePCR application 120 may enter a null value into all of the data fields in the cardiac arrest data section of the stored ePCR 125. If the stored ePCR 125 is in a format compliant with the National Emergency Medical Services Information System (NEMSIS), the cardiac arrest section of the stored ePCR 125 may include eArrest data fields. The ePCR application 120 may set all of the eArrest data fields to the null value.

In an implementation, in response to patient speech 510, the ePCR application 120 may determine a data and time value for an at patient arrival time. The ePCR application 120 may use this time as a supplement, a comparison, and/or in lieu of the at-patient-arrival-time 381 determined based on location information (e.g., as discussed above with regard to FIG. 3A).

Figure 6A:
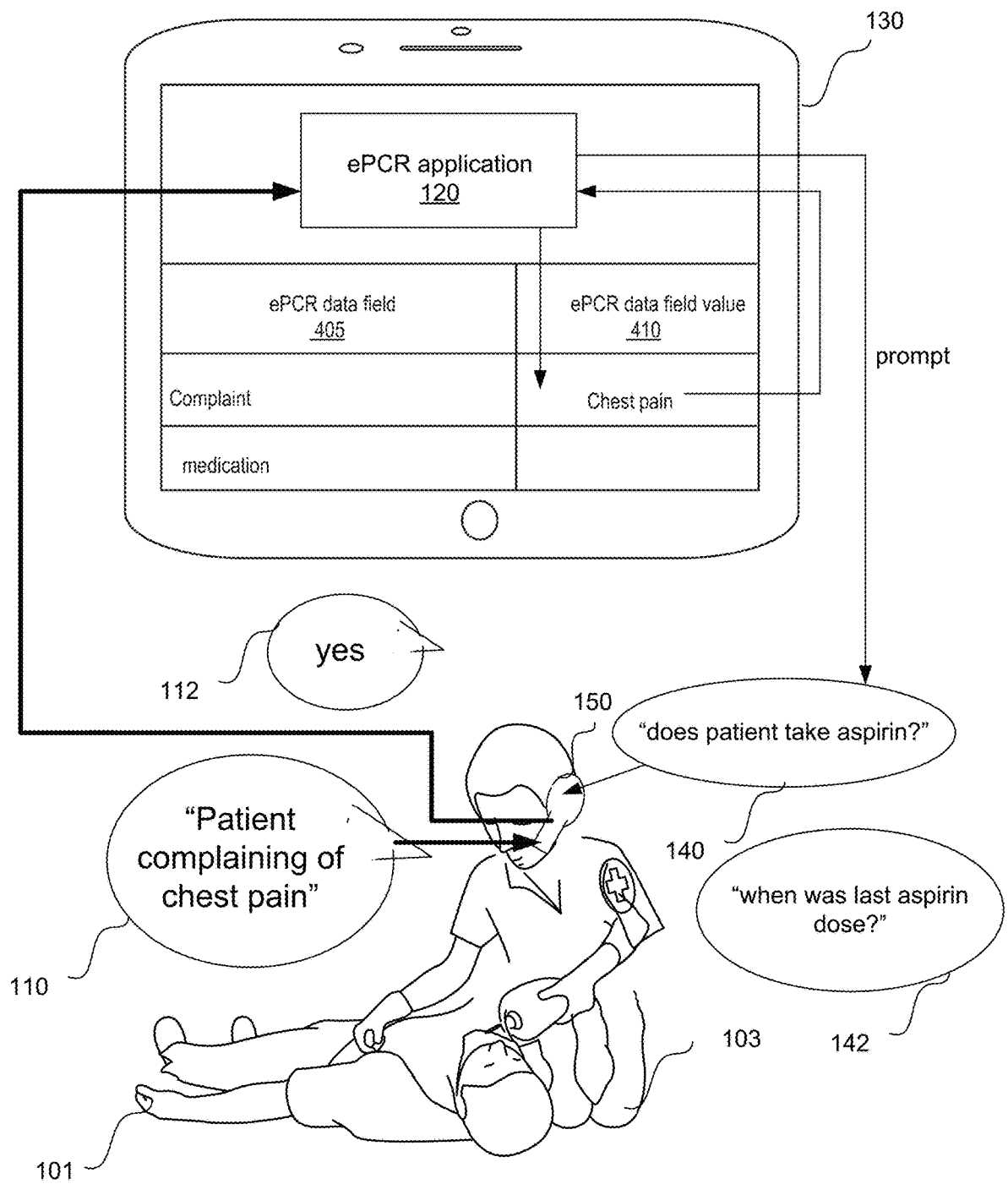
FIGS. 6A, 6B, and 6C show examples of audible caregiver prompts generated based on automated ePCR data capture.
Figure 6B:
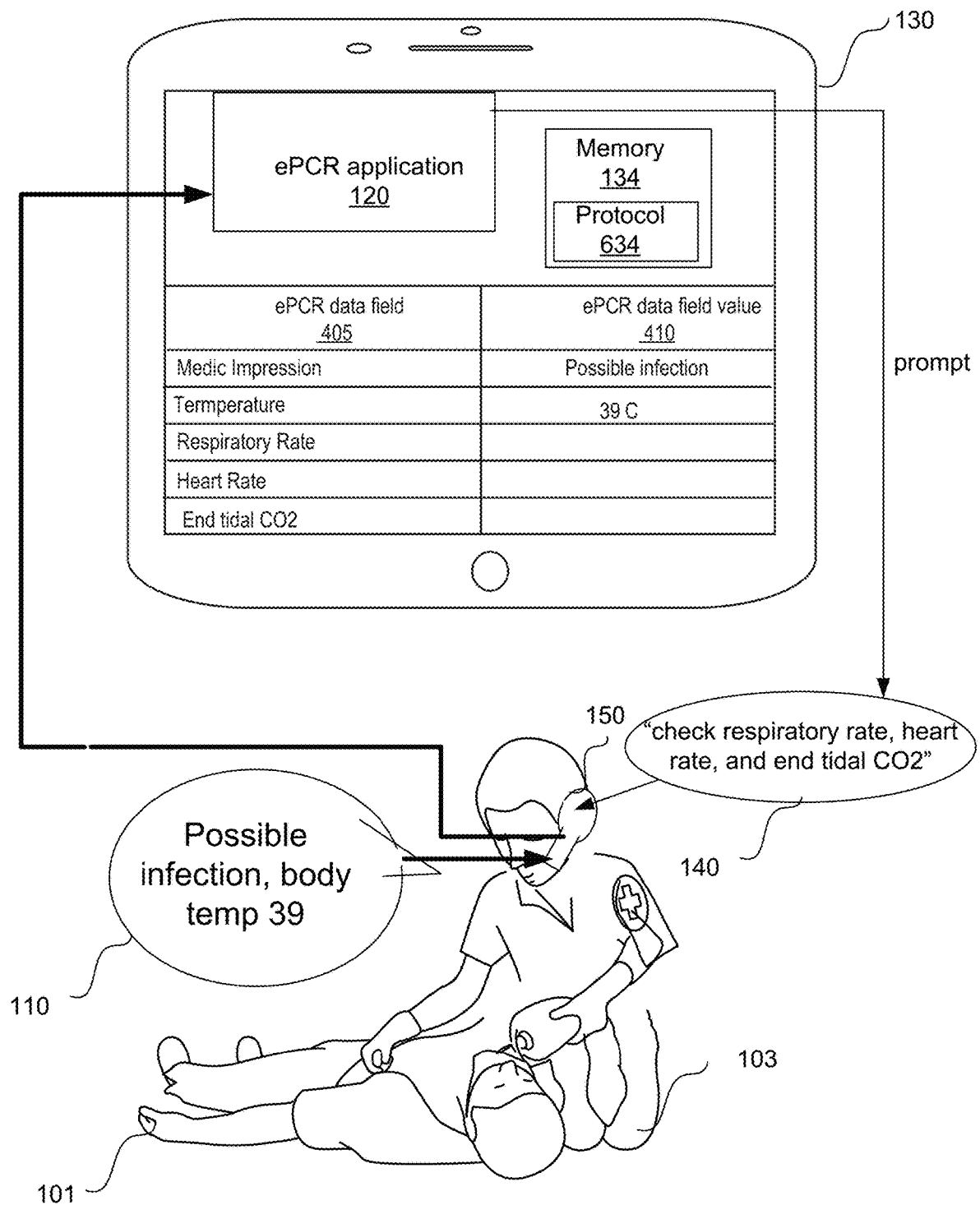
Figure 6C:
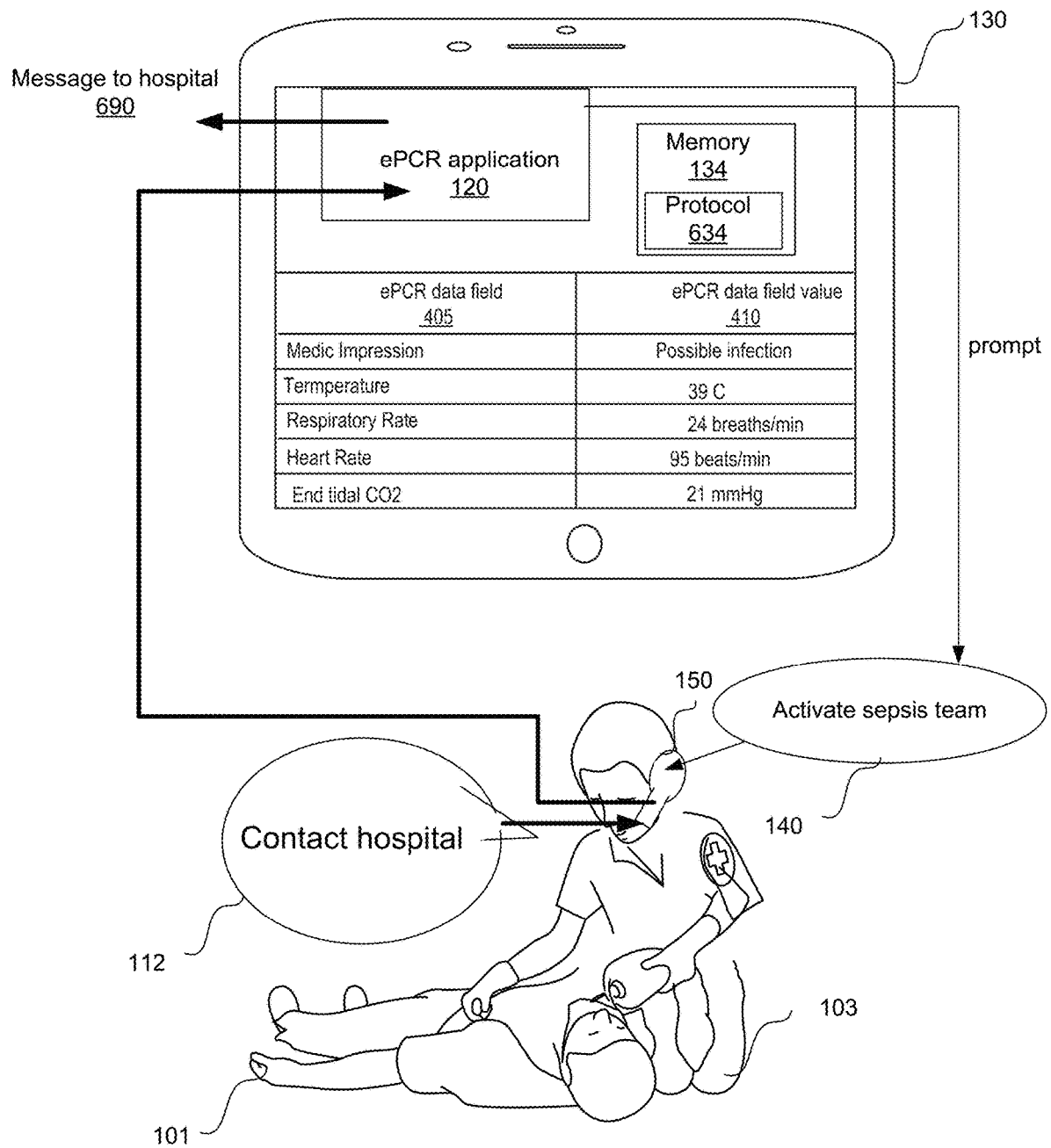

Referring to FIGS. 6A, 6B, and 6C, with further reference to FIG. 1B examples of audible caregiver prompts generated based on automated ePCR data capture are shown. In an implementation, the ePCR application 120 as executed by the processor 132 may generate audible caregiver prompts 140 based on captured patient encounter information in the stored ePCR 125. For example, as shown in FIG. 6A, the ePCR application 120 may identify an unpopulated ePCR data field that is associated with a populated ePCR data field and generate an audible caregiver prompt that includes a request for a value for the unpopulated ePCR data field. For example, the caregiver speech 110 may indicate "chest pain" but the medication field may be unpopulated. In response, the ePCR application 120 may generate an audible caregiver prompt 140 to check if the patient takes aspirin. The ePCR application 120 may generate a follow-up prompt 142 in response to a caregiver response 112 to the audible caregiver prompt 140. For example, with a caregiver response 112 of "yes" to the audible caregiver prompt 140, the ePCR application 120 may fill in a value of "aspirin" in the medications data field and then generate a follow-up prompt 142 of "When was the last aspirin dose?" The ePCR application 120 may further populate the stored ePCR with the time of the last aspirin dose.

Referring to FIG. 6B, the ePCR application 120 may provide the audible caregiver prompt 140 based on one or more unpopulated ePCR data fields 405 and based on the medical protocol 634 stored in the memory 134. For example, the medical protocol 634 may be a sepsis protocol that requires a measurement of temperature, respiratory rate, heart rate, and end tidal CO2. In response to the populated fields, for example, medic impression with a value of "possible infection" and a temperature value indicating an elevated temperature, the ePCR application 120 may identify related fields of respiratory rate, heart rate, and end tidal CO2 as unpopulated and generate an audible caregiver prompt 140 to remind the caregiver to provide these values.

Referring to FIG. 6C, the ePCR application 120 may provide the audible caregiver prompt 140 based on one or more populated ePCR data fields 405 and based on the medical protocol 634. For example, the medical protocol 634 may be a sepsis protocol that requires a sepsis alert based on values of temperature, respiratory rate, heart rate, and end tidal CO2. In this case, the audible caregiver prompt may be "activate sepsis team" as a reminder to the caregiver 103 to contact the hospital on route to activate the sepsis team. In an implementation, based on a caregiver response 112 requesting "contact hospital" from the caregiver 103, the ePCR application 120 may provide a message 690 to a pre-selected or nearby hospital to activate the sepsis team. For example, the ePCR application 120 may provide the message 690 to the hospital or medical facility 195 via the network 180.

In an implementation, the ePCR application 120 may repeat the audible caregiver prompt 140 one or more times. Administered medications, neurological assessments, and vital sign measurements are some examples of procedures that the caregiver 103 may need to repeat at regular intervals. The repeat may occur at a pre-determined interval. In an implementation the repeat may occur until the ePCR application 120 receives the caregiver response (e.g., receives an audible response via the microphone 154) and populates the data field based on the caregiver response. In an implementation, the ePCR application 120 may repeat the audible caregiver prompt a pre-determined number of times. In an implementation, a user of the ePCR application 120 may designate particular ePCR data fields as high priority and some as low priority and may repeat the audible caregiver prompt more times and/or more frequently for the high priority fields than for the low priority fields. In various implementations, the wearable user interface device may provide a haptic prompt in addition to the audible caregiver prompt.

Figure 6D:
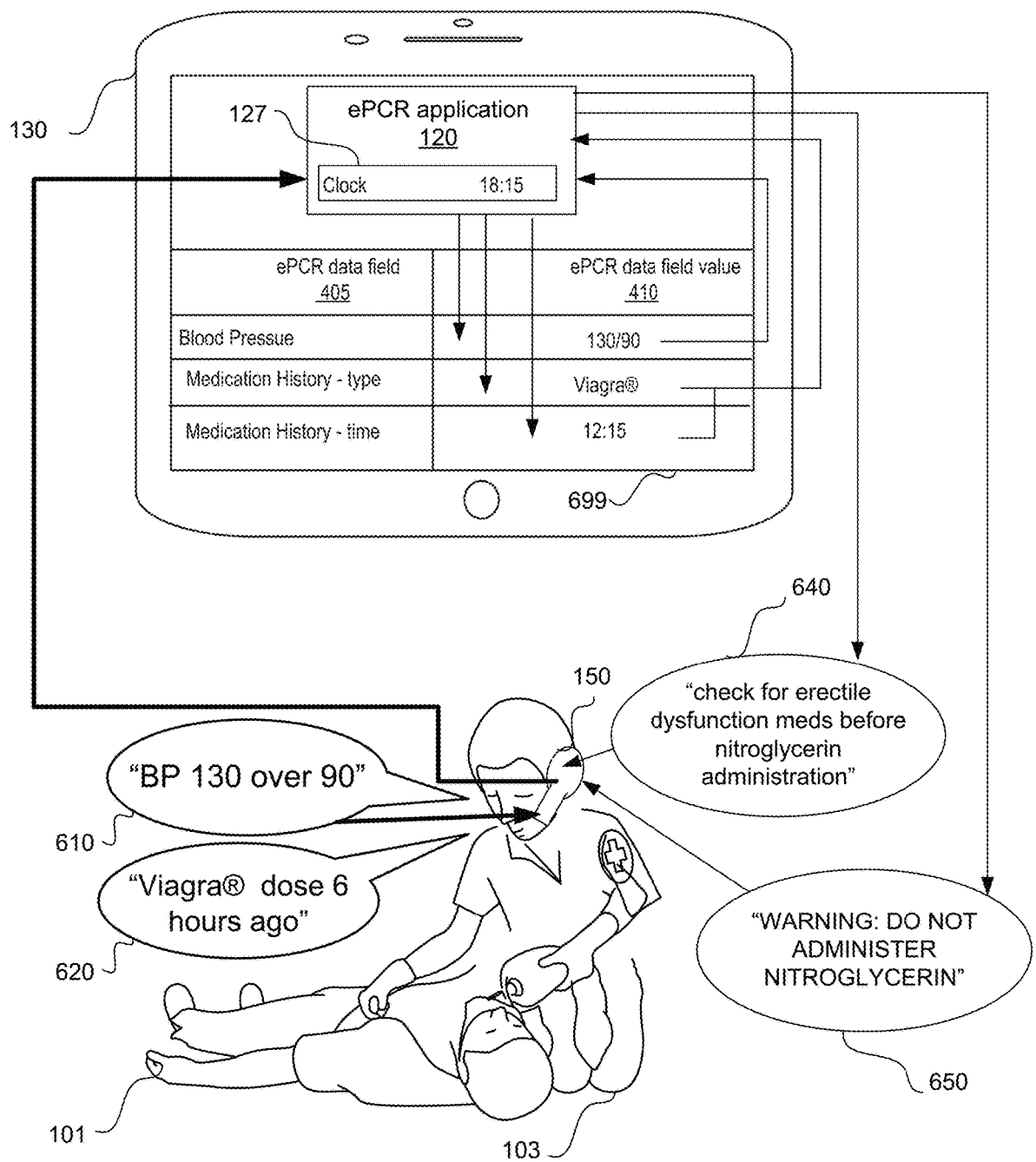
FIG. 6D shows an example of a patient care activity reminder based on an ePCR data field value.

Referring to FIG. 6D, an example of a patient care activity reminder based on an ePCR data field value is shown. In an implementation, the ePCR application 120 may provide a reminder of patient care activities based on a captured data field value according to a medical protocol. In an implementation, the rules engine 116 may link data fields to activate appropriate queries and/or reminders for the caregiver 103. For example, first information 610 from the caregiver 103 may provide the data field value 410 for blood pressure. The data field value 410 may correspond to high blood pressure. Based on this data field value, the ePCR application 120 may generate a first audible caregiver prompt 640 to remind the caregiver 103 to check for erectile dysfunction medication history for the patient before administering nitroglycerin. The caregiver 103 may provide the data field value 410 for medications with second information 620 from the caregiver. This caregiver 103 may provide the second information 620 in response to the prompt 640. In the example of FIG. 6D, the second information 620 may include a type of erectile dysfunction medication and a time that the patient took the medication. Based on the clock 127 and the second information 620, the ePCR application 120 may determine a time that the patient took the medication and automatically enter a data field value 699 for this time. Additionally or alternatively, based on the second information 620, the ePCR application 120 may generate a second audible caregiver prompt 650. This second audible caregiver prompt 650 may be a warning or alarm. For example, based on the field values 410 of "Viagra®" and an administration time within 24 hours, the ePCR application 120 may generate the alarm or patient care warning for the caregiver not to administrate nitroglycerin. In the example of FIG. 6D, the patient care warning is based on a medical therapy contraindication.

Figure 6E:
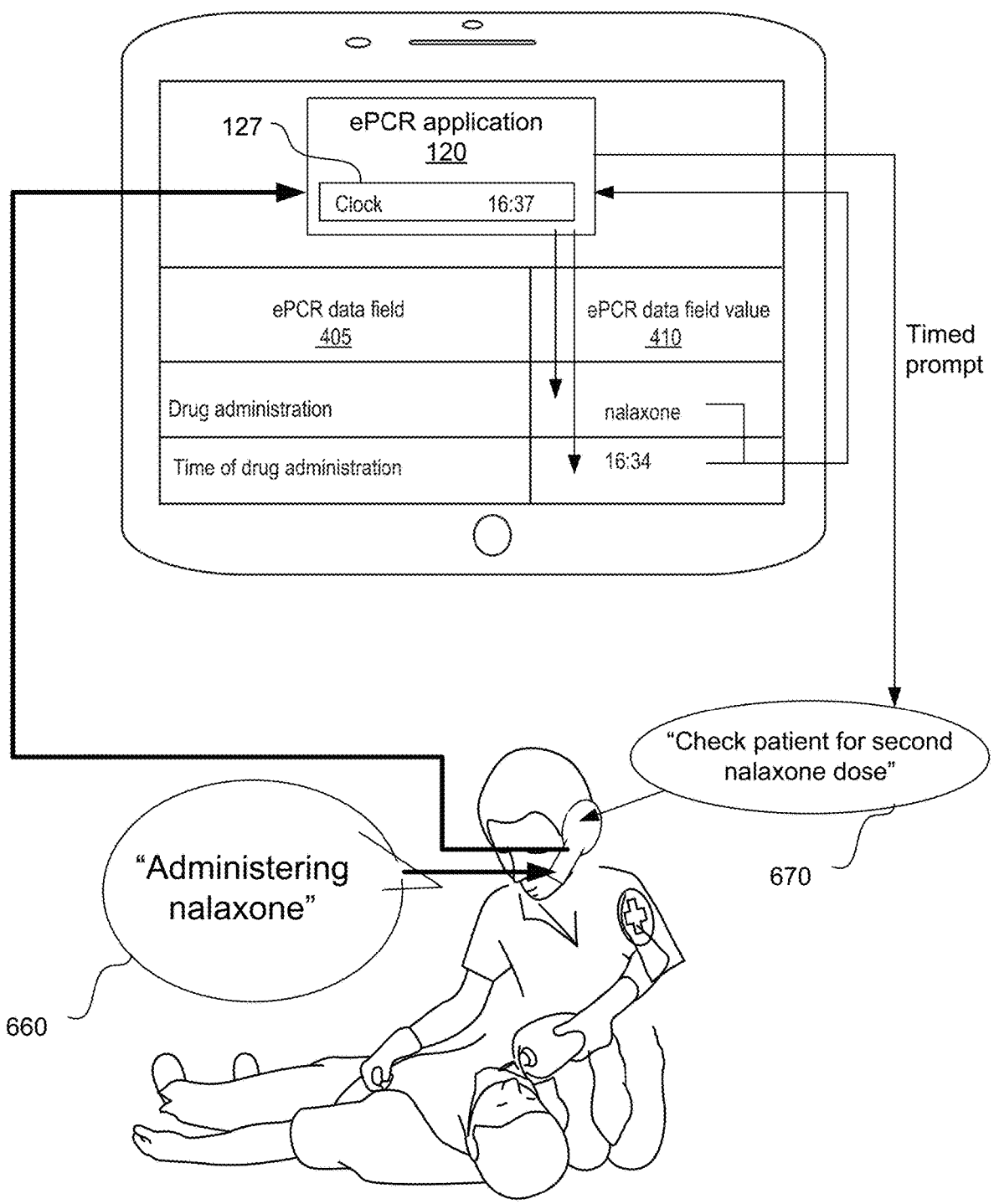
FIG. 6E shows an example of a timed alarm for patient care activities by the caregiver based on captured ePCR data field values.

Referring to FIG. 6E, an example of a timed alarm for patient care activities by the caregiver based on captured ePCR data field values is shown. In an implementation, the alarm or patient care warning may be a timed alarm for patient care activities by the caregiver. The timed alarms may correspond to treatments within the medical protocol 634. For example, a caregiver 103 may automatically record an administration of naloxone to a patient via the caregiver speech 660. The ePCR application 120 may enter the drug administration along with a time of administration. Based on these field values 410, the ePCR application 120 may generate a timed alarm 670 for a second dose of medication. In the naloxone example, the ePCR application 120 may provide this timed alarm 670 two to three minutes after the initial data entry via the caregiver speech 660 based on naloxone administration guidelines from the medical protocol 634. The timed alarm 670 may also apply to treatments and/or monitoring other than drug administration. For example, the timed alarm may be an alarm to repeat a 12 Lead ECG, a vital sign measurement, etc. The timed alarm 670 may occur at a pre-determined interval, for example, according to the medical protocol 634. Additionally or alternatively, the timed alarm may occur in response to a new or updated ePCR data field 405 and/or data field value 410. For example, automated entry of a value for the drug administration data field 405 may trigger a timer for the timed alarm 670.

In an implementation, a data field value in the stored ePCR may trigger a predetermined alarm interval. As examples, recordation of epinephrine delivery may trigger an alarm or reminder to repeat a dosage every three minutes and recordation of administration of CPR compressions may trigger an alarm to repeat every two minutes. Alternatively or additionally, a data field value in the stored ePCR may trigger the ePCR application to request a time interval from the caregiver 103. For example, in response to a recordation of glucose or dextrose delivery, the ePCR application 120 may query the caregiver for a time interval until a reminder to repeat administration of glucose or dextrose. In an implementation, the ePCR application 120 may automatically adjust a time interval or provide a caregiver alert prior to or with an alarm based on physiological data entries that correspond to the alarm. For example, if the stored ePCR indicates an administration of NARCAN®, the ePCR application 120 may activate a timer to provide an alarm to remind the caregiver 103 to repeat the administration. The timer may use a 2-3 minute interval and provide the alarm at the end of this interval. However, the ePCR application 120 may also monitor the breathing rate of the victim. For example, the ePCR application 120 may automatically update the breathing rate data field value based on data received from the medical device 170. If the ePCR application 120 records non-zero breathing rate prior to the expiration of the 2-3 minute timer, the ePCR application 120 may stop the alarm and/or provide a notification to the caregiver. For example, the notification may be "breathing resumed-NARCAN® repeat alarm canceled." As another example, in response to a dose of glucose or dextrose and an indication of hypoglycemia in an ePCR data field, the ePCR application 120 may provide a repetitive alarm to repeat the administration of glucose or dextrose and repeat a blood sugar measurement. With each recorded measurement, the ePCR application 120 may monitor the blood sugar for a rise over 80 mg/dL. If this value is reached, the ePCR application 120 may notify the caregiver 103 and pause the alarm.

Figure 6F:
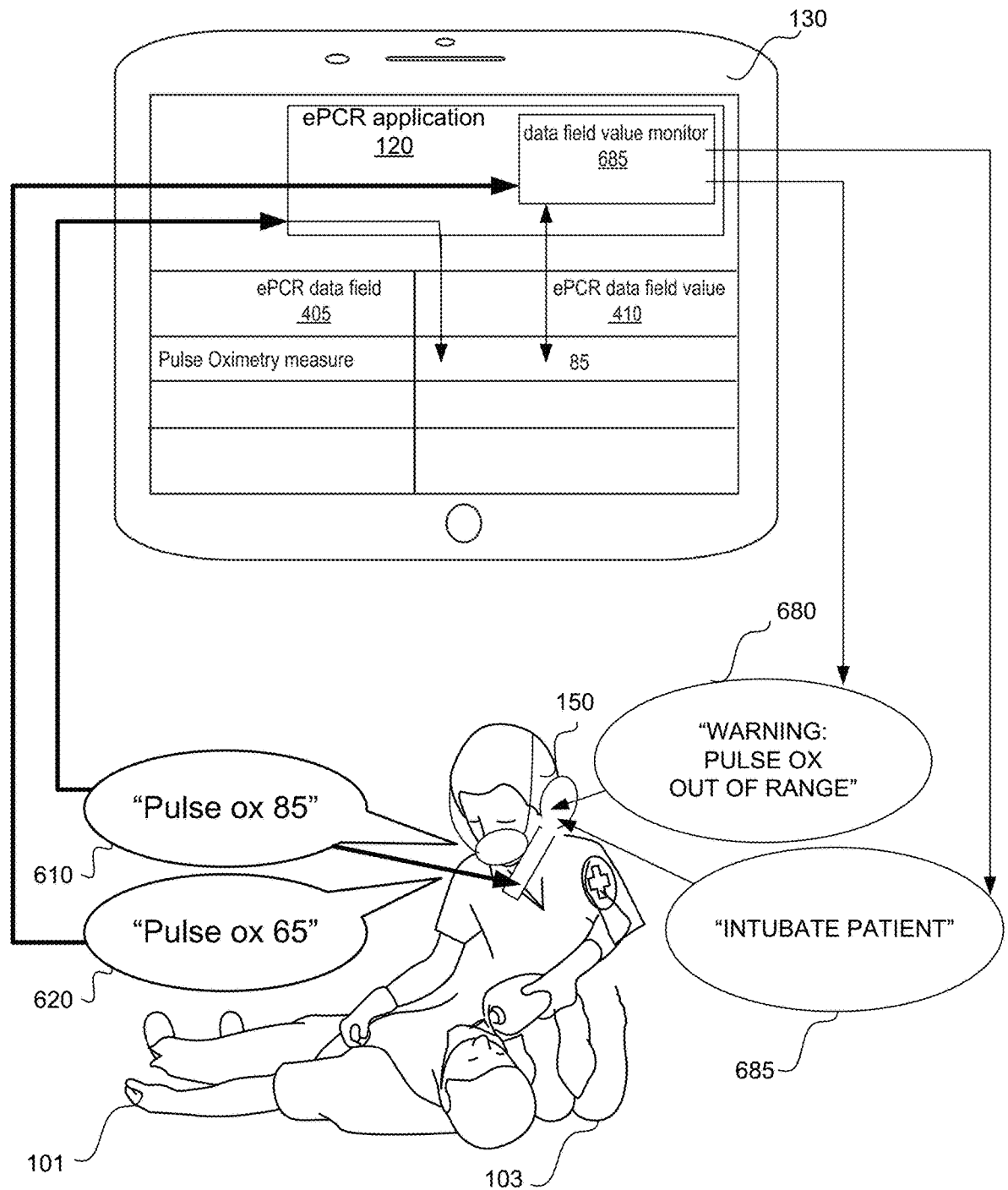
FIG. 6F shows an example of a caregiver prompt based on an evaluation of a patient physiological parameter.

Referring to FIG. 6F, an example of a caregiver prompt based on an evaluation of a patient physiological parameter is shown. In an implementation, the ePCR application 120 may generate a caregiver prompt based on a physiological parameter being unequal to a target value and/or outside of an acceptable range for the target value. For example, the ePCR application 120 may receive a data field value 410 for a data field 405 corresponding to a physiological parameter. The ePCR application 120 may include a data field value monitor 685 configured to compare one or more data field values 410 to a target value and/or a target range. For example, the medical protocol 634 may include target values and/or target ranges for one or more physiological parameters. Based on the comparison, the data field monitor 685 may determine that one or more physiological parameters are unequal to the target value and/or outside of the target range. In response, the ePCR application 120 may generate at least one audible caregiver prompt. The at least one caregiver prompt may be a patient care warning 680 that indicates that the physiological parameter is unequal to the target and/or outside of a target range. For example, the physiological parameter may be a vital sign. In an implementation the value of the physiological parameter may be an initial data field value 410 (i.e., the first value entered for the physiological parameter). For example, the caregiver 103 may arrive at the patient 101 and measure an initial pulse oximeter reading of 65%. The ePCR application 120 may provide the warning 680 in response to this initial value being unequal to the target and/or outside of a target range (e.g., the target range may be 80%-100% for pulse oximetry). Additionally, the ePCR application 120 may provide the warning 680 in response to a change in the physiological parameter. For example, a patient 101 may call 911 due to difficulty breathing and suspected COVID-19 infection. The caregiver 103 may obtain an initial pulse oximetry reading of 85%. Subsequently, the patient's condition may deteriorate precipitously and the pulse oximetry reading may drop to 65%. In response to this change, the ePCR application 120 may generate the warning 680 to alert the caregiver 103 to the change in patient condition. Additionally or alternatively, the ePCR application 120 may generate a patient care activity prompt 685. For example, in response to the precipitous change in the pulse oximetry reading, the ePCR application 120 may generate the activity prompt 685 to intubate the patient 101.

Figure 7A:
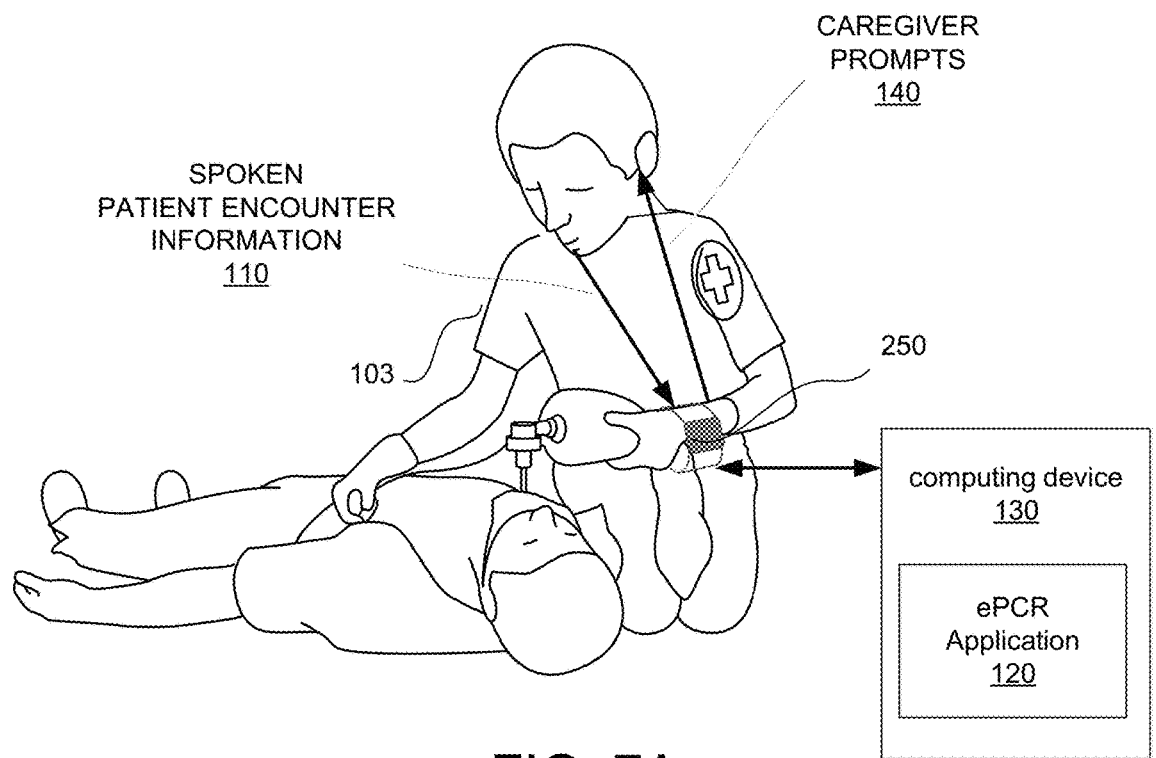
FIG. 7A shows a schematic illustration of capturing caregiver speech and providing caregiver prompts via a watch.
Figure 7B:
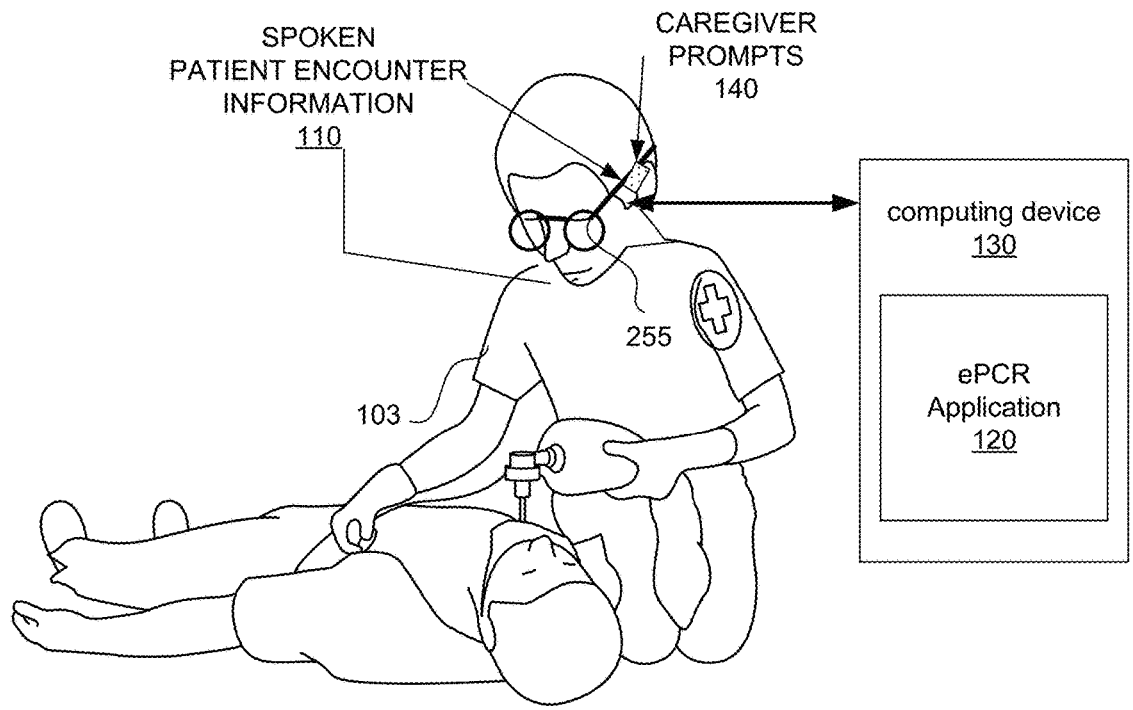
FIG. 7B shows a schematic illustration of capturing caregiver speech and providing caregiver prompts via glasses.

Referring to FIGS. 7A and 7B, schematic illustrations of capturing caregiver speech and providing caregiver prompts via a watch and glasses, respectively, are shown. In FIG. 7A, the caregiver 103 wears the watch 250. The watch 250 may be configured to capture audible patient encounter information 110 and provide caregiver prompts 140 as audible, visual and/or haptic prompts. The watch 250 may be communicatively coupled to the computing device 130. The ePCR application 120 as executed by the processor 132 may populate ePCR data field values 410 based on the spoken patient encounter information 110. Further, the ePCR application 120 as executed by the processor 132 may generate the caregiver prompts 140 for provision by or on the watch 250 as described above for caregiver prompts 140 provided to the earpiece 150. In FIG. 7B, the caregiver 103 wears the AR glasses 255. The AR glasses 255 may be configured to capture audible patient encounter information 110 and provide caregiver prompts 140 as audible, visual and/or haptic prompts. The AR glasses 255 may be communicatively coupled to the computing device 130. The AR glasses 255 may be configured to capture audible patient encounter information 110 and provide caregiver prompts 140 as audible, visual and/or haptic prompts. Further, the ePCR application 120 may generate the caregiver prompts 140 for provision by or on the AR glasses 255 as described above for caregiver prompts 140 provided to the earpiece 150.

Figure 8:
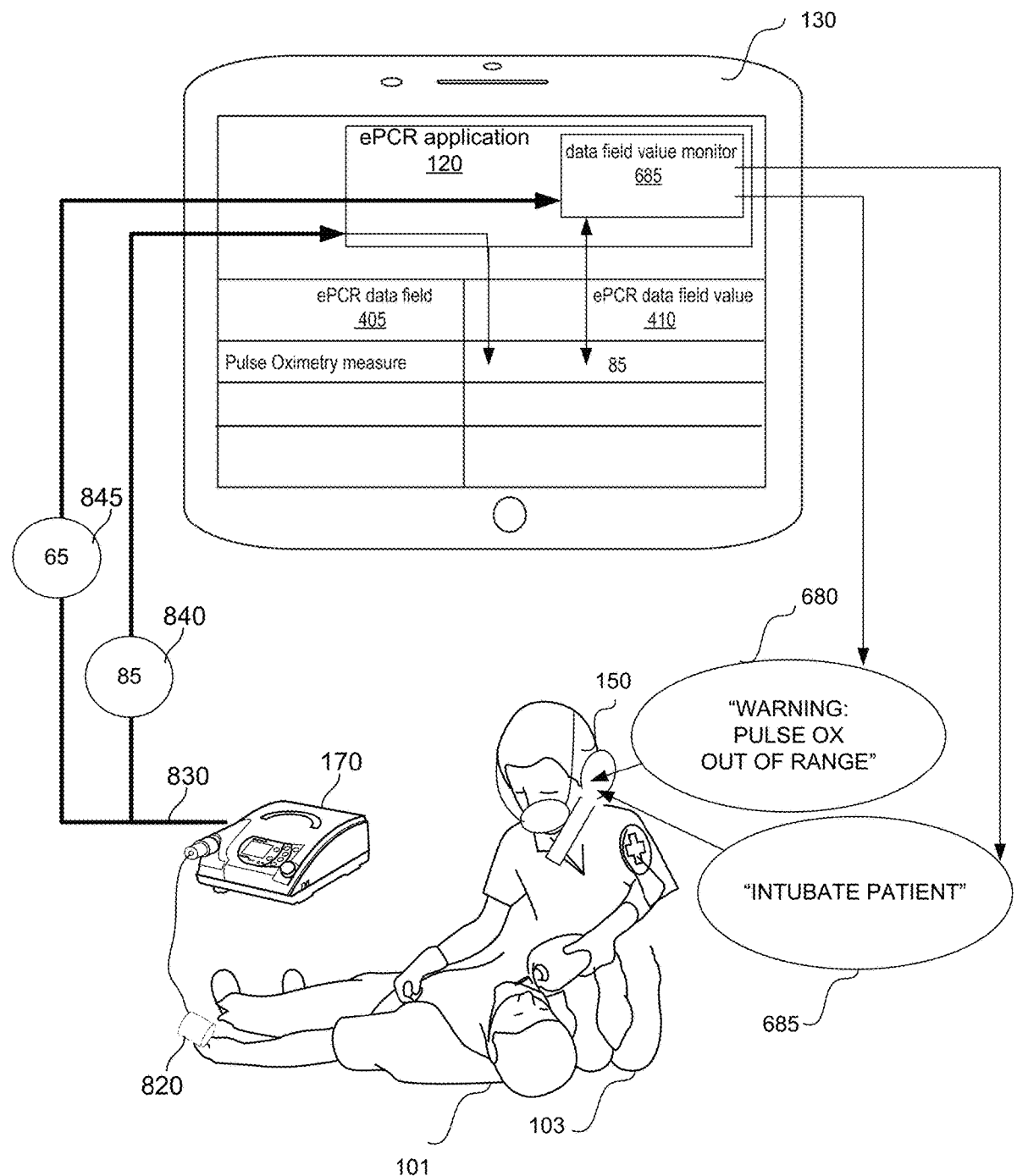
FIGS. 8 and 9 show schematic diagrams of communications between medical devices and the ePCR application.
Figure 9:
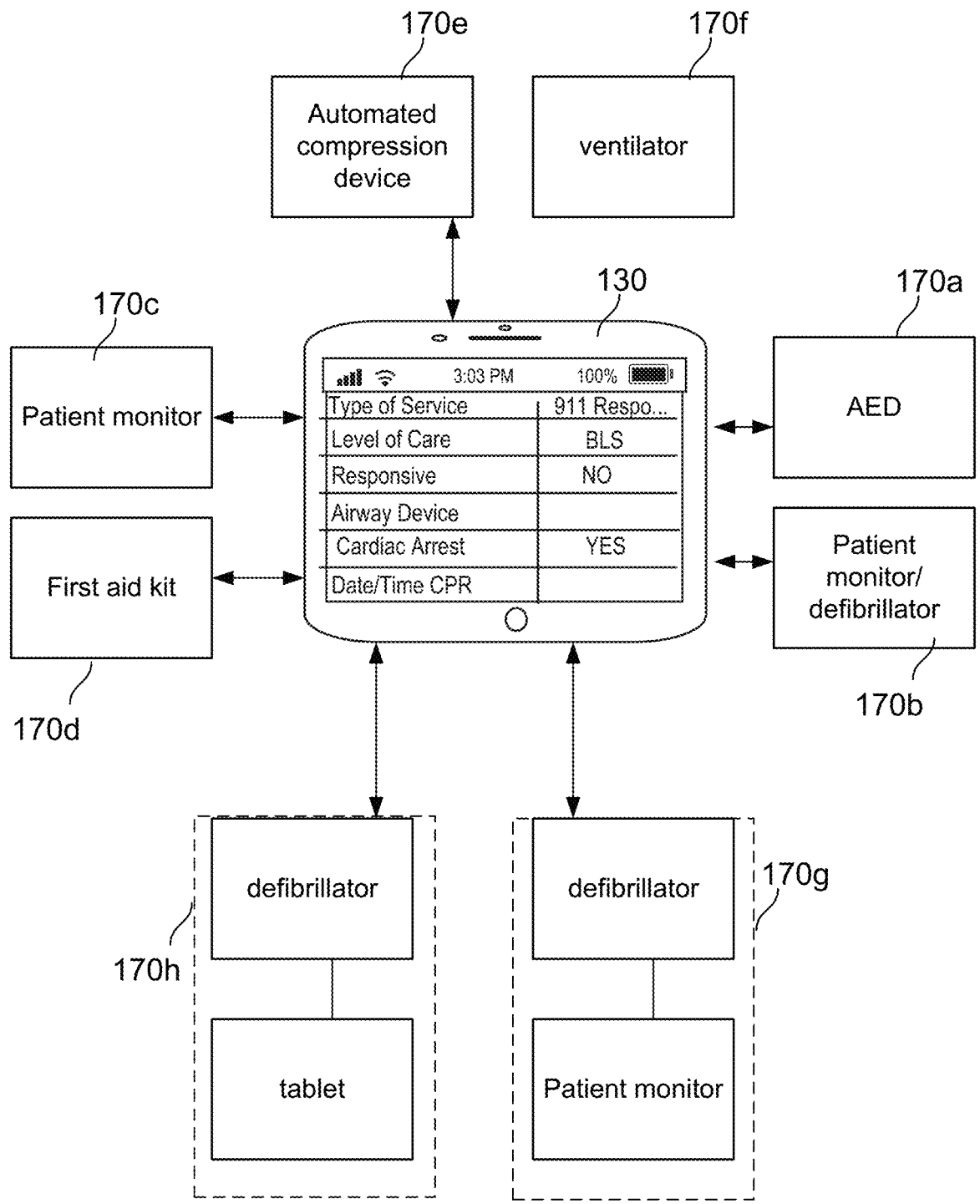

Referring to FIGS. 8 and 9, with further reference to FIG. 1D, schematic diagrams of communications between medical devices and the ePCR application are shown. In an implementation, the computing device 130 may be communicatively coupled to the medical device 170 and receive medical device information from the medical device. In an exemplary use case scenario, the medical device 170 may be a patient monitor/defibrillator. In an exemplary scenario similar to that described with regard to FIG. 6F, a patient 101 may call 911 due to difficulty breathing and a suspected COVID-19 infection. The medical device 170 may include a pulse oximetry sensor 820. The caregiver 103 may attach the pulse oximetry sensor 820 to the patient 101 and the medical device 170 may monitor and send the pulse oximetry measurement to the ePCR application 120 via the communicative coupling 830 between the medical device 170 and the computing device 130. The medical device 170 may obtain an initial pulse oximetry reading of 85% and send this initial measurement 840 to the ePCR application 120. The ePCR application 120 may automatically populate the pulse oximetry data field 405 with the initial measurement 840 from the medical device 170. Subsequently, the patient's condition may deteriorate precipitously. The medical device 170 may obtain a subsequent measurement 845 of 65% and send this subsequent measurement 845 to the ePCR application 120. The ePCR application 120 may include the data field value monitor 685. The data field value monitor 685 may compare the initial measurement 840 and the subsequent measurement 845 to a target value and/or a target range. Additionally, the ePCR application 120 may compare the subsequent measurement 845 to a previous measurement, for example, the initial measurement 840. Based on one or both of these comparisons, the ePCR application 120 may generate an audible caregiver prompt 680 as a warning. The warning may indicate one or more of the deviation of the measurement from the target and/or target range and/or the change in value between the subsequent measurement 845 and a previous measurement, for example, the initial measurement 840. In an implementation, the ePCR application 120 may generate the patient care activity prompt 685. For example, in response to the precipitous change in the pulse oximetry reading, the ePCR application 120 may generate the activity prompt 685 to intubate the patient 101.

The medical device 170 is shown in FIG. 8 as a single device for simplicity. However, as shown in FIG. 9, the medical device 170 may include one or more medical devices including, for example, a defibrillator (e.g., an automated external defibrillator 170a), a patient monitor/defibrillator 170b, a patient monitor 170c, a first aid or trauma kit 170d, an automated compression device 170e, and a ventilator 170f. In an implementation, the medical device may further include a bag-valve mask and/or an airflow sensor. In an implementation, the medical device may be a modular medical device that includes a patient monitor communicatively coupled to a defibrillator 170g or that includes a patient monitor/defibrillator communicatively coupled to a dedicated computer tablet 170h. One or more of the medical devices 170a-170h may include medical imaging capability, for example, ultrasound or laryngoscopy. The computing device 130 may communicatively couple to and receive data field values 410 from one or more of the medical devices 170a-170h associated with the patient 101.

Referring to FIG. 10, an example of a patient data charting system with automated ePCR data capture and caregiver prompting is shown. In the system 1010, a caregiver team that includes at least a first caregiver 1003a and a second caregiver 1003b are shown treating a patient or victim 101. Each caregiver 1003a and 1003b is associated with a respective hands-free wearable user interface device, 1050a (e.g., a first wearable user interface device) and 1050b (e.g., a second wearable user interface device), respectively for automated data capture. The wearable user interface devices 1050a and 1050b may be communicatively coupled to the computing device 130 and the ePCR application 120. The ePCR application 120 may receive first patient encounter information 1010a from the first wearable user interface device 1050a and receive second patient encounter information 1010b from the second wearable user interface device 1050b.

In an implementation, the wearable user interface devices 1050a and 1050b may be earpieces as shown in the example of FIG. 10 and each include a speaker and a microphone. The caregiver 1003a and/or 1003b may speak about the patient encounter, and the microphone of the device 1050a and/or 1050b may capture this spoken patient encounter information 1010a and/or 1010b, respectively. The devices 1050*a* and/or 1050*b* may provide audible information to the mobile computing device 130 via the wireless communicative coupling 1060*a* and/or 1060*b*, respectively. As similarly described in regard to FIG. 1B, the mobile computing device 130 and/or the remote computing device 190, which is communicatively coupled to the mobile computing device 130 via the network 180, may convert the spoken patient encounter information 110 to text patient encounter information.

In the example of FIG. 10, the devices 1050*a* and 1050*b* are shown as earpieces. However, in various implementation, the caregivers 1003*a* and 1003*b* may each be associated with an earpiece, a watch, glasses, or a combination thereof. The first and second patient encounter information 1010*a* and 1010*b* may be audible information and/or may be information entered by the caregiver to a watch display and/or an augmented reality display associated with the glasses. The caregivers in FIG. 10 are shown with the same type of wearable user interface device for simplicity only. In an implementation, the caregivers 1003*a* and 1003*b* may have the same or different types and/or combinations of wearable user interface devices.

The mobile computing device 130 may execute the ePCR application 120 configured for automated ePCR data capture. Via this application, the mobile computing device 130 may store the patient encounter information in an appropriate data field of a stored ePCR. Further, based on this patient encounter information, the ePCR application 120 may determine one or more audible caregiver prompts 1040*a* and 1040*b*. The mobile computing device 130 may provide the caregiver prompts 1040*a* and 1040*b* to one or more of the first and second wearable devices 1050*a* and 1050*b*.

Figure 11:
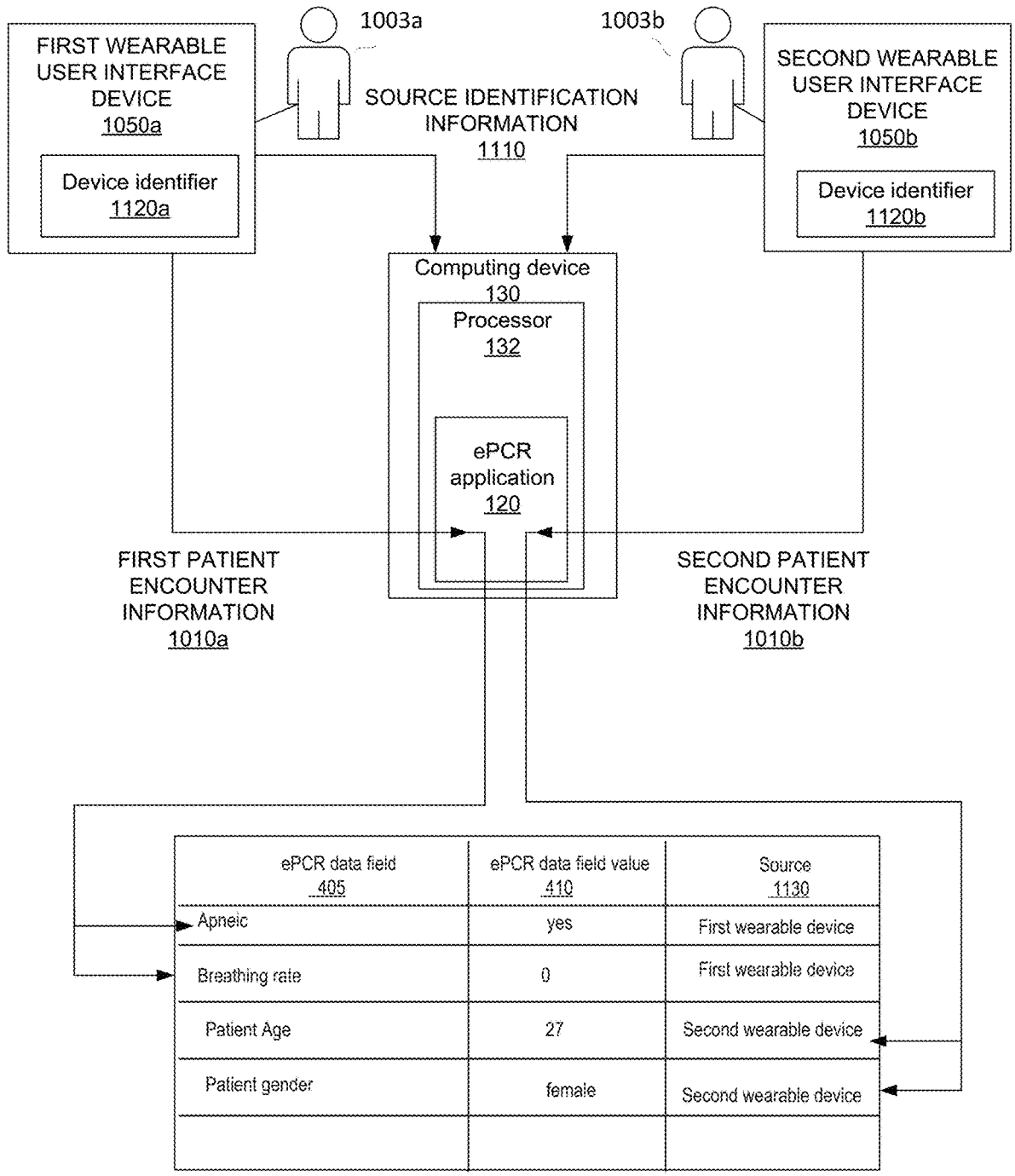
FIG. 11 shows an example of an automated ePCR system configured to distinguish between two or more sources of patient encounter information.

Referring to FIG. 11, an example of an automated ePCR system configured to distinguish between two or more sources of patient encounter information is shown. In this example, the ePCR application 120 as executed by the processor 132 may identify the first wearable user interface device 1050*a* as a source of the first patient encounter information 1010*a* and the second wearable user interface device 1050*b* as a source of the second patient encounter information 1010*b* based on source identification information 1110. The first wearable user interface device 1050*a* may be associated with the first caregiver 1003*a* and the second wearable user interface device 1050*b* may be associated with the second caregiver 1003*b*. In an implementation, the source identification information 1110 may be a device identifier (e.g., a first device identifier 1120*a* and a second device identifier 1120*b*). For example, the wearable user interface devices 1050*a* and 1050*b* may provide the device identifiers to the mobile computing device 130 during a pairing operation to establish communications. Additionally or alternatively, the wearable user interface devices 1050*a* and 1050*b* may provide the device identifiers as metadata with the patient encounter information 1010*a* and/or 1010*b*.

As shown schematically, the ePCR application 120 may populate ePCR data field value(s) 410 for ePCR data field(s) 405 based on the first patient encounter information 1010*a* and/or the second patient encounter information 1010*b*. For example, the first wearable user interface device 1050*a* may be the source of the data field value of "yes" for the data field "apneic" and the data field value of "0" for the data field of "breathing rate." The second wearable user interface device 1050*b* may be the source of the data field value of "5" for the data field "patient age" and the data field value of "female" for the data field of "patient gender." In an implementation, the ePCR application 120 may store the source identification information and/or an indication of the source of the data field values in the memory 134 and/or in the stored ePCR 125.

Figure 12A:
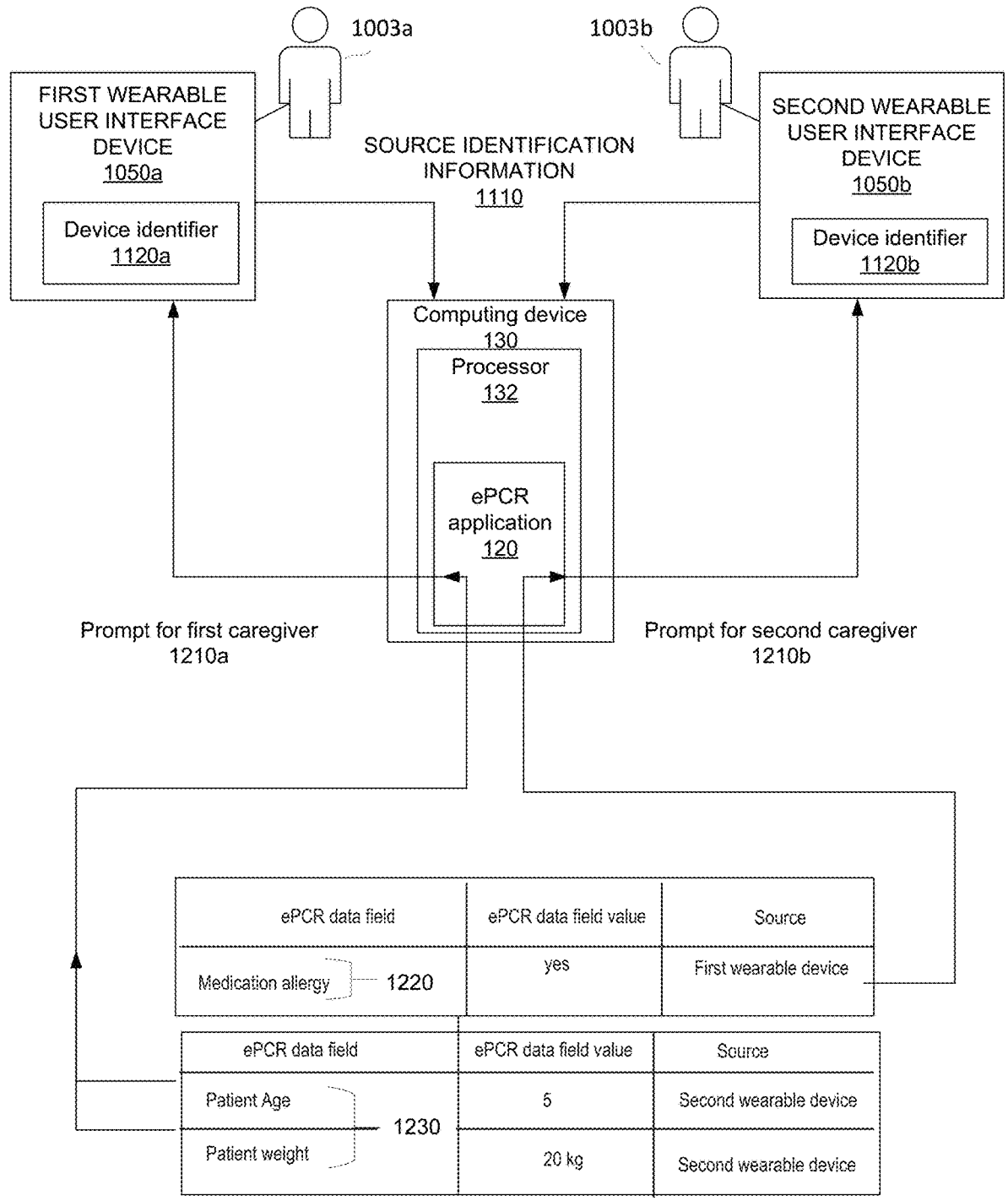
FIG. 12A shows an example of an automated ePCR system configured to provide prompts to a first caregiver based on patient encounter information from a second caregiver.

Referring to FIG. 12A, an example of an automated ePCR system configured to provide prompts to a first caregiver based on patient encounter information from a second caregiver is shown. The ePCR application 120 may selectively provide the data field values to one or more wearable user interface devices. Based on the source identification information, the ePCR application 120 may select one or more wearable user interface devices that are communicatively coupled to the computing device 130 but were not the source of the data field value information provided in the caregiver prompt. In this manner, the ePCR application 120 can share data provided by one caregiver with one or more other caregivers.

In an example implementation, ePCR application 120 may populate the data fields 1220 with values provided by the first wearable device 1050*a* associated with the first caregiver 1003*a*. The values for these fields provide a basis for a prompt 1210*b* for the second caregiver. As one example, the first caregiver 1003*a* may attend to the patient first while the second caregiver 1003*b* prepares medications. The first caregiver 1003*a* may note a medication allergy of the patient and provide this information to the ePCR application 120. The ePCR application 120 may provide the medication allergy information as a prompt 1210*b* for the second wearable user interface device 1050*b*. In response, the second caregiver 1003*b* may receive the allergy information and prepare an appropriate medication for the patient. As another example, the ePCR application 120 may populate the data fields 1230 with values provided by the second wearable device 1050*b* associated with the second caregiver 1003*b*. The values for these fields provide a basis for a prompt 1210*a* for the first caregiver. As one example, the second caregiver 1003*b* may attend to the patient first and note that the patient is a 20 kg child. The second caregiver 1003*b* may provide this information to the ePCR application 120. The ePCR application 120 may provide the age and weight via a prompt 1210*a* for the first wearable user interface device 1050*a*. In response, the first caregiver 1003*a* may receive the age and weight information and adjust medications or treatment equipment accordingly.

In another example, the first caregiver 1003*a* may attend to the patient first while the second caregiver 1003*b* prepares to ventilate the patient. The first caregiver may enter the approximate weight and height of the patient on the ePCR. The ePCR application 120 may calculate the preferred ventilation tidal volume and rate and provide the tidal volume and rate as prompts 1210*b* for the second wearable user interface device 1050*b*. The preferred ventilation tidal volume and rate may also be communicated to the air flow sensor (e.g., an Accuvent®) or defibrillator where ventilation feedback is being calculated or displayed. In response, the second caregiver 1003*b* may deliver ventilations via a bag valve mask (BVM) that are measured via the air flow sensor and feedback provided to the second rescuer responsible for the ventilations.

The ePCR application 120 may generate the caregiver prompts 1210*a* and 1210*b* as similarly described above with regard to FIGS. 6A-6F. For example, in various implementations, the caregiver prompts 1210*a* and 1210*b* may include an alarm. The alarm may be a timed alarm for patient care activities and/or a patient care warning based on the data field values in the stored ePCR 125. The patient care warning may be, for example, a drug or medical therapy contraindication. In an implementation, the ePCR data field value is a physiological parameter, such as a vital sign, and the alarm indicates that this parameter is out of a range or unequal to a target value.

In various implementations, the ePCR application 120 may receive multiple values for one or more data fields. To resolve this issue, the ePCR application 120 may populate the one or more data fields according to one or more conflict resolution protocols. For example, the ePCR application 120 as executed by the processor 132 may assign one or more first sections of the ePCR to the first caregiver 1003a and patient encounter information 1010a received from the first wearable user interface device 1050a. Similarly, the ePCR application 120 as executed by the processor 132 may assign one or more second sections of the ePCR to the second caregiver 1003b and patient encounter information 1010b received from the second wearable user interface device 1050b. Based on these assignments, the ePCR application 120 may restrict population of a data field to the patient encounter information received from the assigned device. Alternatively, the ePCR application 120 may prioritize population of the data field based on the assignment. For example, the ePCR application 120 may populate a data field with a value received from an unassigned user interface device and then replace this value with a value received from an assigned user interface device. The ePCR application 120 may request confirmation from one or more of the user interface devices prior to replacing a value based on an assignment. In an implementation, the ePCR application 120 may include a notification of a change or difference in the value as part of the replacement confirmation. In an implementation, the assignment of a wearable user interface device to a section of the ePCR may be a predetermined assignment. For example, an EMS crew may include members with different assigned roles where each assigned role corresponds to a section of the ePCR. An agency supervisor or medical director may assign these roles and the associated section prior to any dispatched call. Alternatively, the crew may set up these assignments on route to the emergency scene. In an implementation, the predetermined assignments may be default assignments and the crew may rearrange these assignments on route to the victim based on the makeup of the crew.

In an implementation, the ePCR application 120 may populate data fields with values according to selection rules. For example, the data field may be a single use data field configured to hold a single value. The ePCR application 120 may populate this data field with the first value in the combined first and second patient encounter information 1010a and 1010b that corresponds to the data field. In an implementation, the ePCR application 120 may receive a second and subsequent value for the data field in the combined first and second patient encounter information 1010a and 1010b. The ePCR application may generate a caregiver prompt (e.g., the prompt 1210a for the first caregiver, the prompt 1210b for the second caregiver, or a combination thereof) to confirm replacement of the first data field value with the second and subsequent data field value. Upon receipt of a response from either the first or second wearable user interface device, the ePCR application 120 may replace the value. In an implementation, only one or a select subset of the caregivers may have authorization to confirm the replacement of the data field value. In this case, the ePCR application 120 may store the source identification information corresponding to the authorized caregiver and only replace the data field value if the source of the confirmation corresponds to the stored source identification information. In an implementation, the at least one data field may be a multi-use field. The multi-use field may include more than one value. For this type of field, the processor 325 may populate the data field with multiple values from one or more of the patient encounter information 1010a and 1010b.

Figure 12B:
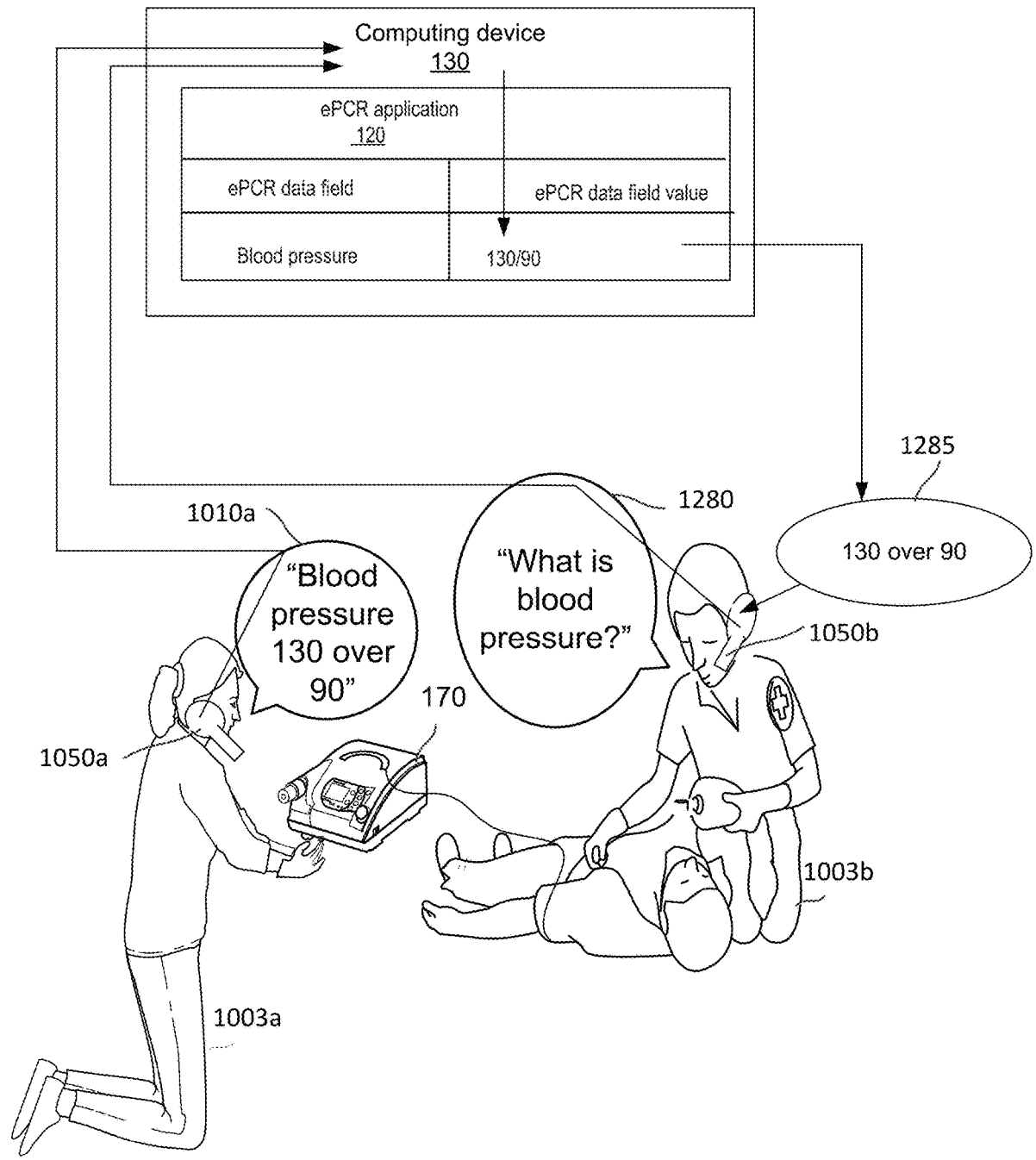
FIG. 12B shows an example of an automated ePCR system configured to provide prompts in response to a caregiver query.

Referring to FIG. 12B, an example of an automated ePCR system configured to provide prompts in response to a caregiver query is shown. In an implementation, the first caregiver 1003a may provide patient encounter information 1010a to the mobile computing device 130 via the first wearable user interface device 1050a. The second caregiver 1003b may ask the ePCR application 120 for information previously provided to the ePCR application 120 by the first caregiver 1003a. The second wearable user interface device 1050b may provide the caregiver query 1280 to the mobile computing device 130. In response to the caregiver query 1280, the ePCR application 120 and the mobile computing device 130 may provide a query response 1285 to the second wearable user interface device 1050b. In an implementation, the ePCR application 120 may receive patient encounter information at a first time from the first caregiver and provide that information in the query response 1285 at a second time in response to a caregiver query 1280 from one or more of the first and second caregivers. Additionally or alternatively, the ePCR application 120 may receive medical device information via a communicative coupling between the medical device 170 and the mobile computing device 130. The ePCR application 120 may populate data field values based on the medical device information and provide these data field values in the query response 1285.

Figure 13:
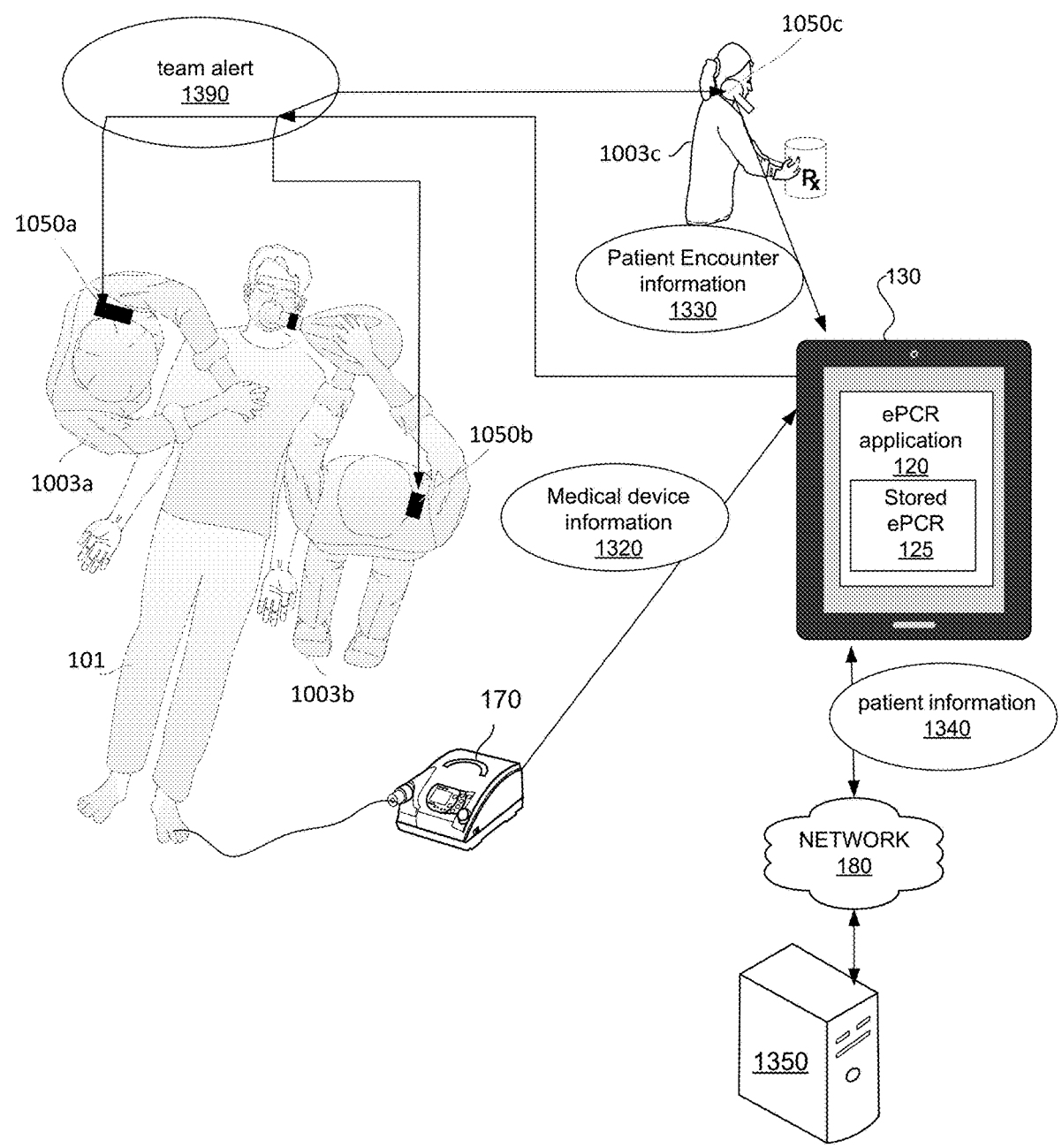
FIG. 13 shows an example of an automated ePCR system configured to provide team alerts.

Referring to FIG. 13, an example of an automated ePCR system configured to provide team alerts is shown. In practice, an EMS team or crew often includes two or more caregivers. The team alert 1390 may relay information determined by one or more caregivers or a medical device to the rest of the EMS team. In various implementations, the team alert 1390 may include one or more of patient medication information, patient allergy information, vital sign measurement(s), changes in vital sign measurement(s), physiological parameter(s), changes in physiological parameter(s), treatment information, and/or information derived from these types of information. In an implementation, the team alert 1390 may be a medication alert based on a medication history data field and/or an administered medication data field.

In some scenarios, members of an EMS team perform different tasks. For example, in the case of a drug overdose, one or more team members may be preparing the victim for transport and one or more other team members may be actively monitoring the victim's breathing rate and administering NARCAN® and/or performing CPR. The team members actively monitoring the patient may receive a primary alert from the ePCR application 120 about any changes in the patient breathing. For a primary alert, the ePCR application 120 may require an acknowledgement to ensure that the caregiver(s) are aware of critical medical information. However, the team members preparing the victim for transport may receive this information as a secondary alert without a required acknowledgement. For these team members, the information is important but not critical to completion of their assigned task.

In the example of FIG. 13, the EMS team includes three caregivers 1003a, 1003b, and 1003c. Each caregiver is associated with a wearable user interface device (e.g., the devices 1050a, 1050b, and 1050c). These devices are shown as earpieces as an example only. In an implementation, the wearable user interface devices for two or more caregivers may include one or more earpieces, one or more watches, one or more glasses, and combinations thereof. The whole EMS team may all use the same type or types of devices or the type(s) of device(s) may vary between team members.

As an exemplary scenario, the EMS team with caregivers 1003a, 1003b, and 1003c may arrive at the patient's house in response to a 911 call. The caregivers 1003a and 1003b may begin treatment of the patient in the living room. Meanwhile, the caregiver 1003c may locate a medication for the patient 101 in the bathroom or bedroom of the patient's house. The caregiver 1003c may provide the medication information (e.g., the patient encounter information 1330) to the ePCR application 120 via the wearable user interface 1050c. In response, the ePCR application 120 may save the medication information in the stored ePCR 125 and may generate a team alert 1390 that includes the medication information. In an implementation, the computing device 130 may send the team alert 1390 to all of the wearable user interface devices associated with the EMS team. In this manner, the caregiver 1003c that provided the patient encounter information 1330 knows that the alert has gone out to the entire team. In an implementation, the computing device 130 may exclude the source device (the device 1050c in this example) and send the team alert 1390 to all of the wearable user interface devices 1050a and 1050b except the source device 1050c.

As discussed in the example above, the ePCR application 120 at the mobile computing device 130 may receive patient encounter information 1330 from a caregiver via a wearable user interface device. Additionally or alternatively, the ePCR application 120 may receive medical device information 1320 from a medical device 170 and/or other patient information 1340 from a remote computing device 1350 (e.g., a computing device associated with emergency dispatch, a medical records database, a remote physician or other caregiver, a healthcare facility, etc.). Based on the patient encounter information 1330, medical device information 1320, and/or other patient information 1340, the ePCR application 120 may populate one or more data field values in the stored ePCR 125. Based on these values, the ePCR application 120 may generate a team alert 1390 and provide the alert to one or more or to all of the wearable user interface devices (e.g., 1050a, 1050b, and 1050c) associated with the EMS team.

In an implementation, the medical device information 1320 may include information for the patient 101 recorded by the medical device 170. For example, this information may include vital signs and/or other physiological parameters and/or treatment information (e.g., defibrillation shock, first aid, drug administration, ventilation, chest compressions, etc.). The patient encounter information 1330 may include information provided to the ePCR application 120 about the patient encounter by a caregiver via a wearable user interface device. For example, the patient encounter information 1330 may include patient demographics, emergency scene descriptions, narrative information, vital signs and/or other physiological parameters, caregiver observations, treatment information, drug information, allergy information, transport information, etc. The other patient information 1340 may include historical patient information (e.g., previous medical conditions or care, drug information, allergy information, etc.).

In an implementation, the team alert 1390 may include and repeat information received by the ePCR application 120 (e.g., the medical device information 1320, the patient encounter information 1330, and/or the other patient information 1340). For example, the ePCR application 120 may receive a vital sign value, such as a heart rate or pulse oximetry value in the medical device information 1320 or the patient encounter information 1330 and repeat that vital sign value in the team alert 1390 provided to the caregivers. As another example, the ePCR application 120 may receive medical device information 1320 indicating that a third defibrillation shock has been applied and repeat this information in the team alert 1390. As a further example, the ePCR application 120 may receive other patient information indicating a patient history of respiratory disease or drug overdose and repeat this information in the team alert 1390.

In an implementation, the team alert 1390 may include information inferred or derived from information received by the ePCR application 120 (e.g., the medical device information 1320, the patient encounter information 1330, and/or the other patient information 1340). For example, the ePCR application 120 may receive a name of a medication and provide a team alert 1390 with a patient medical condition associated with the medication. For instance, if the name of the medication is fluticasone propionate, then the team alert 1390 may be "medication indicates asthma." As another example, if the ePCR application 120 receives patient encounter information indicating a dose of Viagra® within the last six hours, the team alert 1390 may be "nitroglycerin contraindicated."

In an implementation, team alert 1390 may provide information in the team alert 1390 based on a change in information received by the ePCR application 120. For example, this information may include an alarm indicating a change in patient status such as a change-in-vital-sign alarm. For example, the ePCR application 120 may receive a first data field value for blood pressure of 120/80 followed by a second data field value of 130/90 for the same data field. The ePCR application may provide a team alert 1390 of "increase in blood pressure to 130 over 90." The change in information may apply to vital signs or other monitored physiological parameters for the patient based on information received by the ePCR application 120 from the caregivers and/or from the medical device.

In an implementation, the team alert 1390 may include a timing alert. For example, the timing alert may include an en-route-to-patient-scene time, an at-patient-arrival-time, an at-patient-side duration time, an in-transport time, an estimated time of arrival at a hospital, and/or a hospital arrival time. In this manner, the ePCR application 120 may keep all members of an EMS team apprised of times relevant to patient care decisions and treatments.

Figure 14A:
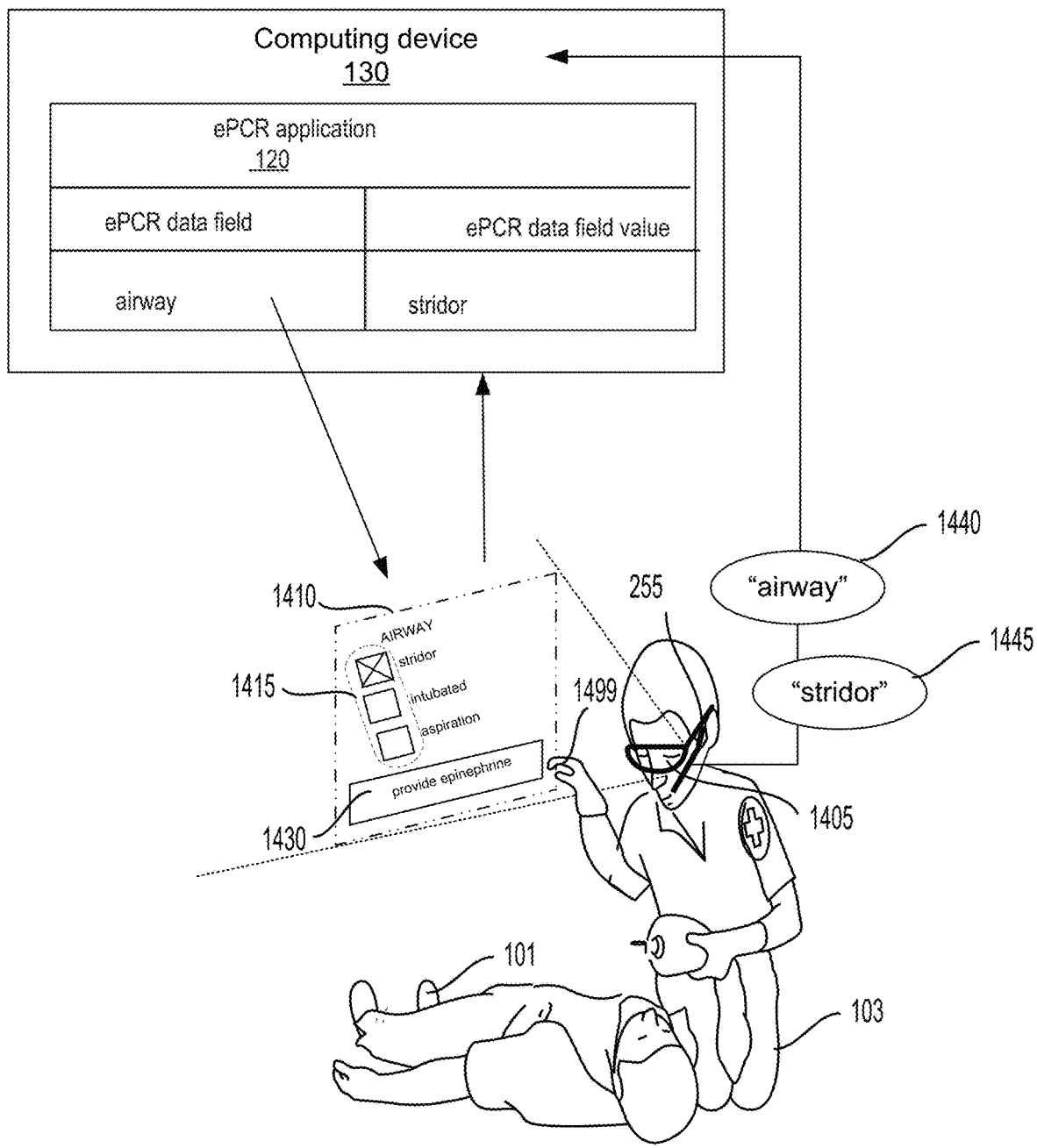
FIGS. 14A and 14B show examples of an augmented reality wearable user interface display for ePCR data entry.
Figure 14B:
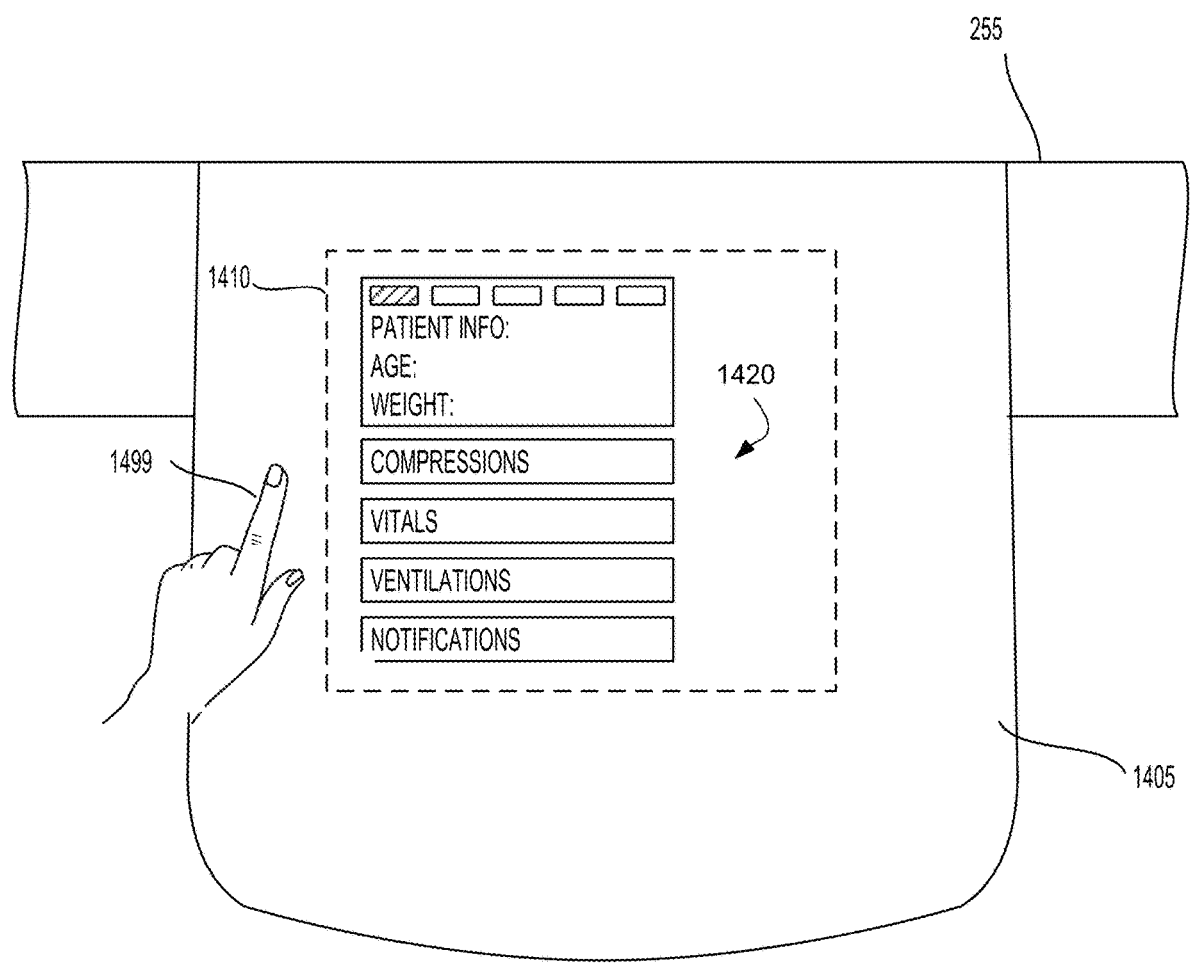

Referring to FIGS. 14A and 14B, with further reference to FIG. 2B, examples of an augmented reality wearable user interface display for ePCR data entry are shown. In an implementation, the wearable user interface device that communicates with the mobile computing device 130 and the ePCR application 120 may be the AR glasses 255. As described in further detail with regard to FIG. 18, the AR glasses 255 may include a processor 1832, a memory 1831, a projector 1824, and other components configured to provide an augmented reality (AR) display image 1410 at the lens 1405 of the AR glasses 255. In an implementation, the AR glasses 255 may include a communications interface 1840 that enables the processor 1832 to communicatively couple to the computing device 130 and the ePCR application 120. In an implementation, the memory 1831 may include the ePCR application 120 and the processor 1832 may execute functions of the ePCR application 120. In such an implementation, the processor 1832 may communicatively couple with one or more other computing devices, such as, for example, the remote computing device 190, the CAD computing device 174, the medical records computing device 178, the medical facility computing device 179, and/or the medical device 170. Similarly to the processor 132, the processor 1832 of the AR glasses 255 may execute a speech-to-text conversion application 136 for speech captured by the microphone 274 and/or may rely on a speech-to-text conversion application 196 associated with the remote computing device 190.

In an implementation, the caregiver 103 may interact with the AR display image 1410 to provide patient encounter information to the ePCR application 120. For example, the caregiver 103 may interact with the AR display 1410 via hand gesture input 1499 to a virtual touchpad 1415. For example, the AR display 1410 may provide prompts (e.g., drop-down menu(s) 1420 or other selectable display features and/or caregiver notifications 1430, such as instructions and/or recommendations) for data fields of an ePCR form. The caregiver 103 may indicate selections of menu item(s) or responses to prompts via the hand gesture input 1499 to the virtual touchpad 1415. Alternatively or additionally, the caregiver 103 may provide a verbal data input 1445 to the ePCR application 120 based on the prompts on the AR display 1410.

In an implementation, as shown in FIG. 14B, the caregiver 103 may select a portion of the ePCR form from a drop-down menu 1420. As an example, the drop-down menu may provide options of "patient info-compressions-vitals-ventilations-notifications." As another example, the drop-down menu 1420 may provide a selectable menu of "Airway—Breathing—Circulation" and provide the portion of the ePCR form corresponding to the selected item. The example in FIG. 14A shows a portion of an airway section of the ePCR. In various implementations, the AR display 1410 may provide a menu and/or an ePCR portion that includes or corresponds to airway, arrest, crew, device, dispatch, disposition, exam, history, injury, labs, medications, narrative, and/or one or more other or custom data field sections of the ePCR form. In an implementation, the selectable ePCR portions may correspond to NEMSIS format portions for ePCR. In an implementation, the caregiver 103 may provide an audible request 1440 for a portion of the ePCR form via the microphone 274 (e.g., as shown in FIG. 2B). The ePCR application 120 may receive the audible request 1440 via the communicative coupling between the mobile computing device 130 and the AR glasses 255. In response, the ePCR application 120 may provide the requested ePCR portion to the AR glasses 255 for AR display.

Figure 15A:
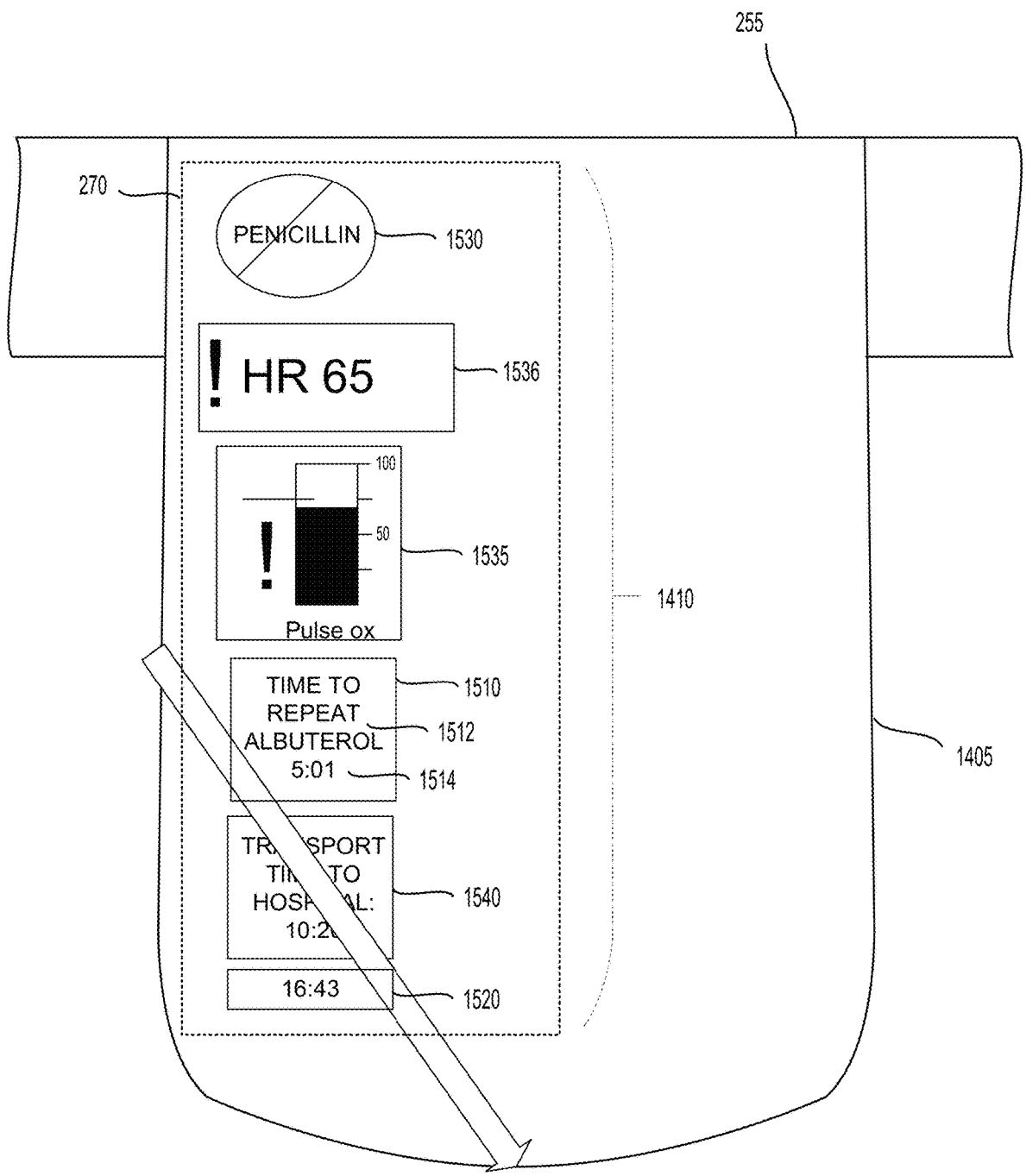
FIG. 15A shows an example of an augmented reality wearable user interface display for ePCR alarms.

Referring to FIG. 15A, with further reference to FIG. 2B, an example of an augmented reality wearable user interface display for ePCR alarms is shown. In an implementation, the notification(s) 1430 may be caregiver prompts that include alarms. In various implementations, the image 1410 may include graphical, textual, and/or numerical representations of the alarms. The alarms may include, for example, a timed alarm 1510 for a patient care activity. The patient care activity may include a patient treatment and/or a patient evaluation. The patient treatment may include a delivery of therapy, for example, a drug administration, an intubation, an administration of oxygen, CPR, a defibrillation shock, pacing, airway nebulizer, epinephrine, aspirin etc. The patient evaluation may include a measurement or check of a physiological parameter including a vital sign, a patient interrogation (e.g., to evaluate cognition and/or pain), etc.

The ePCR application 120 may determine the patient care activity corresponding to a populated data field value based on a medical protocol. For example, if the data field value for medication indicates "albuterol," the medical protocol may advise a repeat administration of this medication at a particular time interval. The ePCR application 120 may provide an advised patient care activity 1512 and an associated timer 1514 for the display of the timed alarm 1510 at the AR glasses 255. The timer 1514 may be a countdown timer and/or a clock time. The AR glasses 255 may display a current time 1520 for reference. At the expiration of the countdown timer, the AR glasses 255 may change the nature of the displayed alarm, provide an audible alarm via the speaker 272, and/or provide a haptic alarm. The change in the nature of the displayed alarm may include one or more of a color change, a size change, a position change, and/or a change from a steady display to a flashing display.

As another example, the ePCR application 120 may determine a patient care warning based on one or more populated data field values in the stored ePCR. In various implementations, the patient care warning may be a drug contraindication and/or a medical treatment contraindication. For example, the "allergy" data field may indicate an allergy to penicillin and the ePCR application 120 may control the AR glasses 255 to display this contraindication as the patient care warning 1530. As another example, the "medication" data field may indicate a recent Viagra® dose and the ePCR application 120 may control the AR glasses 255 to display "do not administer nitroglycerin" as the patient care warning 1530.

As a further example, the ePCR application 120 may determine a caregiver procedure warning based on one or more populated data field values in the stored ePCR. For example, the ePCR application 120 may monitor the data field values for respiratory rate, pulse oximetry, end tidal carbon dioxide, and temperature for a personal protective equipment (PPE) warning. The rules engine 116 may apply a rule of "if respiratory rate high, pulse oximetry low, end tidal carbon dioxide high, and temperature high, then provide PPE warning." Therefore, with a high respiratory rate (e.g., over 16 breaths per minute), a high end tidal carbon dioxide (e.g., above 45 mm Hg), and a low pulse oximetry reading (e.g., below 95), the ePCR application 120 may provide a verbal and/or visual warning of "PPE recommended." These data field values may indicate COVID-19 rather than shock because shock would be expected to correspond to a reduced body temperature. In the case of COVID-19, the caregiver procedure warning would remind the caregiver 103 to don PPE.

As another example, the ePCR application 120 may control the AR glasses 255 to display an alarm that includes a patient physiological parameter warning. The ePCR application 120 may receive patient physiological parameters in the patient encounter information received via the microphone 274 and/or the virtual touchpad 1415. Additionally or alternatively, the ePCR application 120 may receive patient physiological parameters in medical device information received from the medical device 170 communicatively coupled to the processor executing the ePCR application 120. The ePCR application 120 may store the patient physiological parameters in the ePCR as data values. For example, the data values may include vital signs (e.g., heart rate, respiration rate, body temperature) and/or other physiological parameters such as a pulse oximetry measurement, a blood pressure, EtCO2, tissue oxygenation etc. In an implementation, the ePCR application 120 may compare the patient physiological parameters to a target value and/or target range according to a medical guideline or protocol. The ePCR application 120 may determine that the patient physiological parameter is outside of the target range and/or unequal to the target value and generate the patient physiological parameter warning as an out-of-range warning 1535. In an implementation, the ePCR application 120 may store a first value of a physiological parameter (e.g., as received from the microphone, the virtual touchpad, and/or the medical device) in the stored ePCR. Subsequently, the ePCR application 120 may receive a second value for the same physiological parameter. The ePCR application 120 may compare the second value with the first value and generate a warning that indicates a detected difference between these values. For example, the ePCR application 120 may receive the first value of the heart rate at 80 bpm. Subsequently, the ePCR application 120 may receive the second value of the heart rate at 65 bpm and generate the change in value warning 1536. This warning may indicate the new value of the physiological parameter and/or may indicate the direction of the change (i.e., increase or decrease). The ePCR application 120 may control the AR glasses 255 to display the warning 1535 and/or 1536.

In an implementation, the ePCR application 120 may assign an urgency rating to the alarms and control the alarm display to indicate this urgency rating. For example, the alarm display may change color and/or change from steady to flashing to indicate the urgency rating. The color may follow a sequence, such as green to yellow to red, based on urgency. The frequency of the flashing display may increase based on urgency. Additionally, the ePCR application 120 may control the haptic device and/or the speaker to provide a tactile and/or audible warning based on urgency. For example, the heart rate warning 1536 may display in a steady green color for heart rates between 60 and 100 with a change of less than 10% from an original value, but change to yellow for a heart rate between 60 and 100 with a change of 10%-25% from the original value and further change to flashing red if the value drops below 60 or goes above 100.

In an implementation, the target range, target value, and/or urgency rating may depend on multiple data field values in the stored ePCR. For example, for heart rate, the ePCR application 120 may determine these factors and the resultant alarm based on an original heart rate combined with a patient age, patient gender, patient medication, chief complaint, and/or other physiological parameters, treatments, or other patient observations that may affect these factors. As a more specific example, the ePCR application 120 may flag a pulse rate of 150 as normal in a 20 year old victim but flag the pulse rate of 150 as urgently high in a 70 year old victim.

In an implementation, the ePCR application 120 may control the AR glasses 255 to display a location based time 1540. For example, the location based time 1540 may be one or more of the on route to patient scene time 380, the at patient arrival time 381, the at patient side duration time 382, the estimated time of arrival 383, the in transport time 384, and/or the hospital arrival time 385, as discussed with regard to FIG. 3A. The AR glasses 255 may display the location based time 1540 as a countdown timer or a clock time. In an implementation, the ePCR application 120 may control the AR glasses 255 to change the display of the location based time 1540 (e.g., color, position, steady to flashing, flashing frequency, etc.) based on the one or more other parameters in the stored ePCR 125 and/or based on a medical protocol.

For example, as mentioned previously, in some clinical situations such as treating patients with a heart attack (i.e. myocardial infarction) or stroke, the total time duration from EMS arrival at the patient location ("at scene") to the time of delivery of the therapeutic intervention ("door-to-balloon" time or "911-call-to-balloon" time) are critical durations by which to accurately measure as well as utilize in Statistical Process Control or Quality Improvement (SPC, QI) of the medical system. These location based times can be concatenated to span a total time of treatment. Based on predetermined maximum values for the individual durations, specific alarms can be set for the individual durations or for the overall treatment time. For instance, if the at-scene location-based duration exceeds a predetermined value of 17 minutes for treating a heart attack victim then a warning will be provided on the various devices that the caregivers need to get the patient into the ambulance to begin transport to a hospital.

Figure 15B:
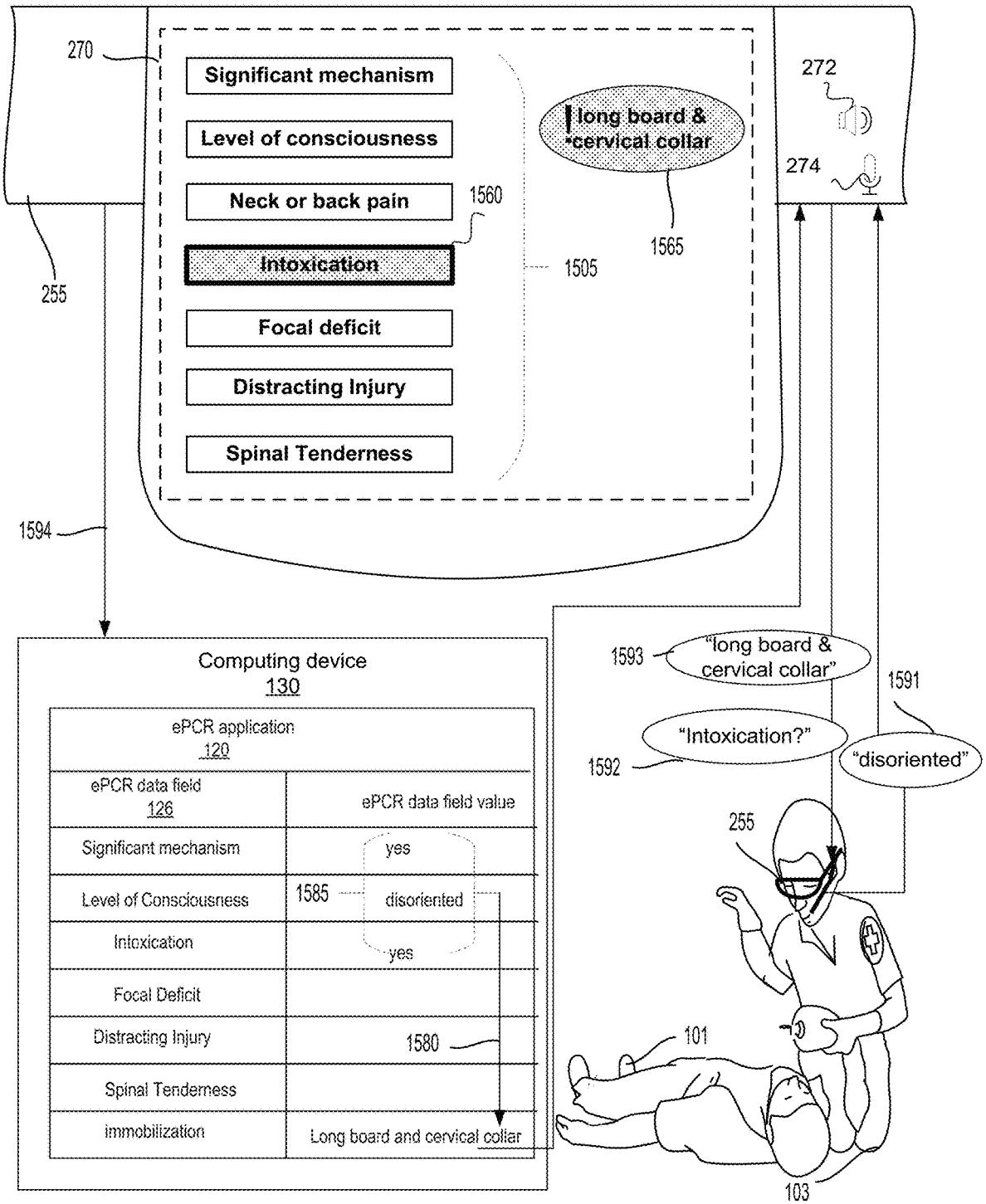
FIG. 15B shows an example of an augmented reality wearable user interface display for protocol reminders.

Referring to FIG. 15B, an example of an augmented reality wearable user interface display for protocol reminders is shown. In an implementation, the rules engine 116 may trigger a set of protocol reminders based on one or more data field values. For example, a data field entry of head injury in a trauma category may trigger reminders and prompts for a spinal immobilization checklist. In an implementation, the AR glasses 255 may provide a visual spinal immobilization checklist 1505. In order to prompt and remind the caregiver 103 to follow the checklist and provide data field values, the ePCR application 120 may highlight entries on the visual list (e.g., the highlighted entry 1560 of "intoxication") and/or may provide audible reminders and prompts (e.g., the audible reminder or prompt 1592 for the caregiver 103 to check for and provide a value for intoxication). The caregiver may provide verbal responses (e.g., the response 1591 of "disoriented") and/or may provide tactile responses at an AR display. The AR glasses 255 may provide the responses to the computing device 130 (e.g., via the communication link 1594). The ePCR application 120 may record the responses 1585 from the caregiver in the corresponding ePCR data fields 126 of the stored ePCR. Based on the recorded responses, the rules engine 116 may infer a value for a data field. For example, the recorded responses 1585 may be sufficient to satisfy a medical protocol criteria for using a long board and cervical collar. Therefore, the ePCR application 120 may automatically populate 1580 the "immobilization" field with the value of "long board and cervical collar" based on application of a rule from the rules engine 116 to the recorded entries 1585. Further, the ePCR application 120 may provide an audible recommendation 1593 for use of the long board and cervical collar and/or a visual alarm or reminder 1565 for the use of the long board and cervical collar.

Figure 16:
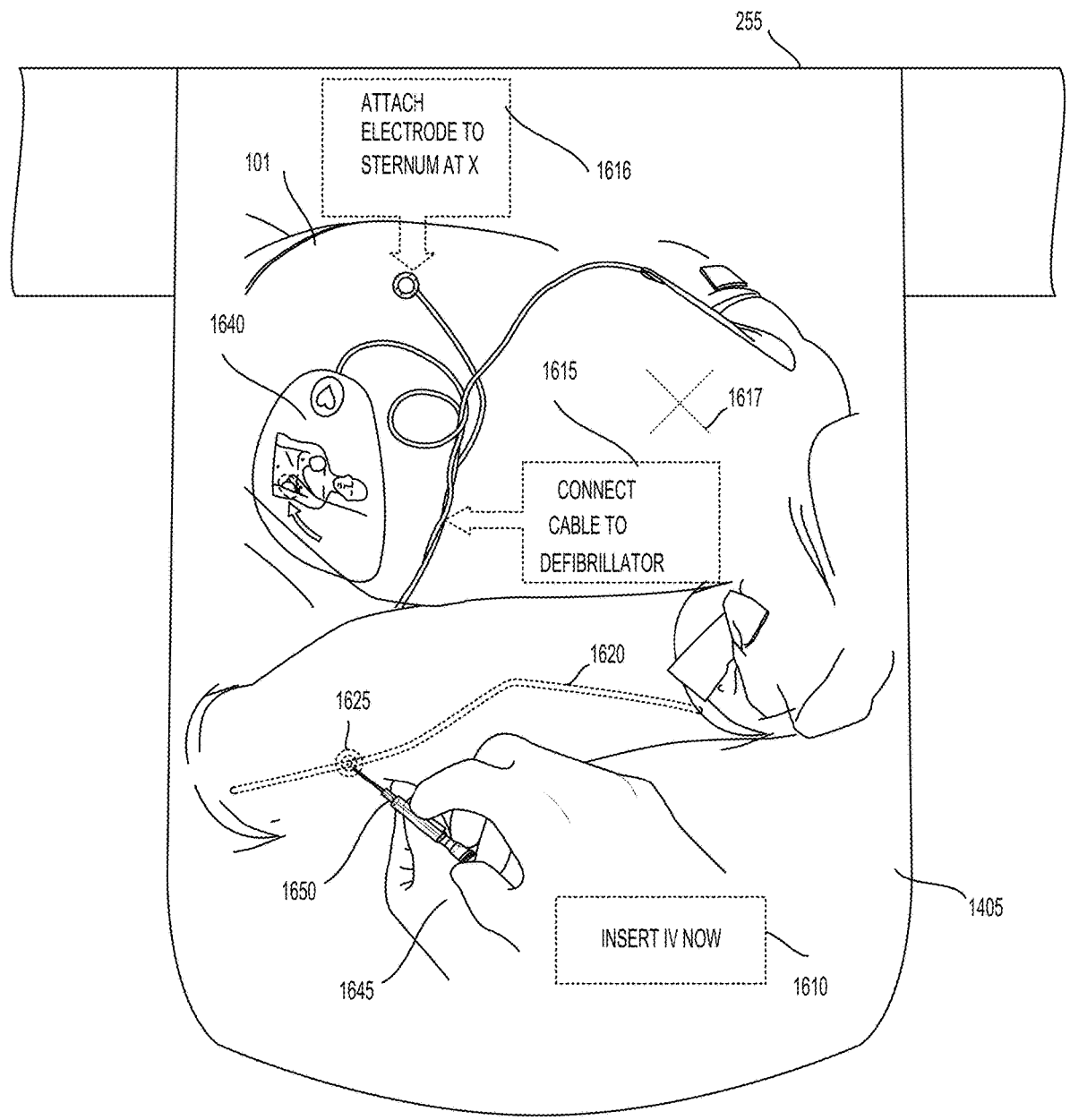
FIG. 16 shows an example of virtual instructions superimposed on a real-space view of an emergency scene.

Referring to FIG. 16, an example of virtual instructions superimposed on a real-space view of an emergency scene is shown. In an implementation, the caregiver may view all or a portion of a patient 101 in the field of view of the AR glasses 255. The caregiver may also view her hands 1645 and medical equipment, such as, for example, defibrillation pads 1640 and a hypodermic needle 1650 in the field of view of the AR glasses 255. These objects, represented in FIG. 16 with solid lines, are real-space objects. The ePCR application 120 may cause the AR glasses 255 to superimpose virtual instructions on these real-space objects. For example, the virtual instructions may include text instructions 1610, such as the "insert IV now" instruction. The virtual instructions may include a text instruction with an equipment indicator, such as the "connect cable to defibrillator" instruction 1615 and the "attach electrode to sternum at x" instruction 1616. The text instruction with the equipment indicator may reference the instruction to a particular item of equipment or a particular component. This may enable the ePCR application 120 to provide detailed instructions on the use of an item of medical equipment. The virtual instructions may further include virtual representations of locations on the patient's body at which to perform a procedure (e.g., the injection site 1625 and the electrode placement site 1617) and/or may further include virtual representations of internal organs (e.g., the blood vessel 1620) in order to guide the caregiver in performing the medical procedures. The ePCR application 120 may generate these virtual instructions in response to and based in part on data field values in the stored ePCR. For example, if the medications data field includes the data field value of "nitroglycerin," the ePCR application 120 may generate the drug injection instructions as shown for example in FIG. 16. As another example, if a medical therapy or medical device field includes an indication that a patient monitor/defibrillator is in use, the ePCR application 120 may generate the electrode instructions as shown for example in FIG. 16. In an implementation, the ePCR application 120 may provide the virtual instructions in response to an audible request from the caregiver for instructions. For example, the caregiver may say "nitroglycerin injection help" and, in response, the ePCR application 120 may provide the virtual instructions.

Figure 17:
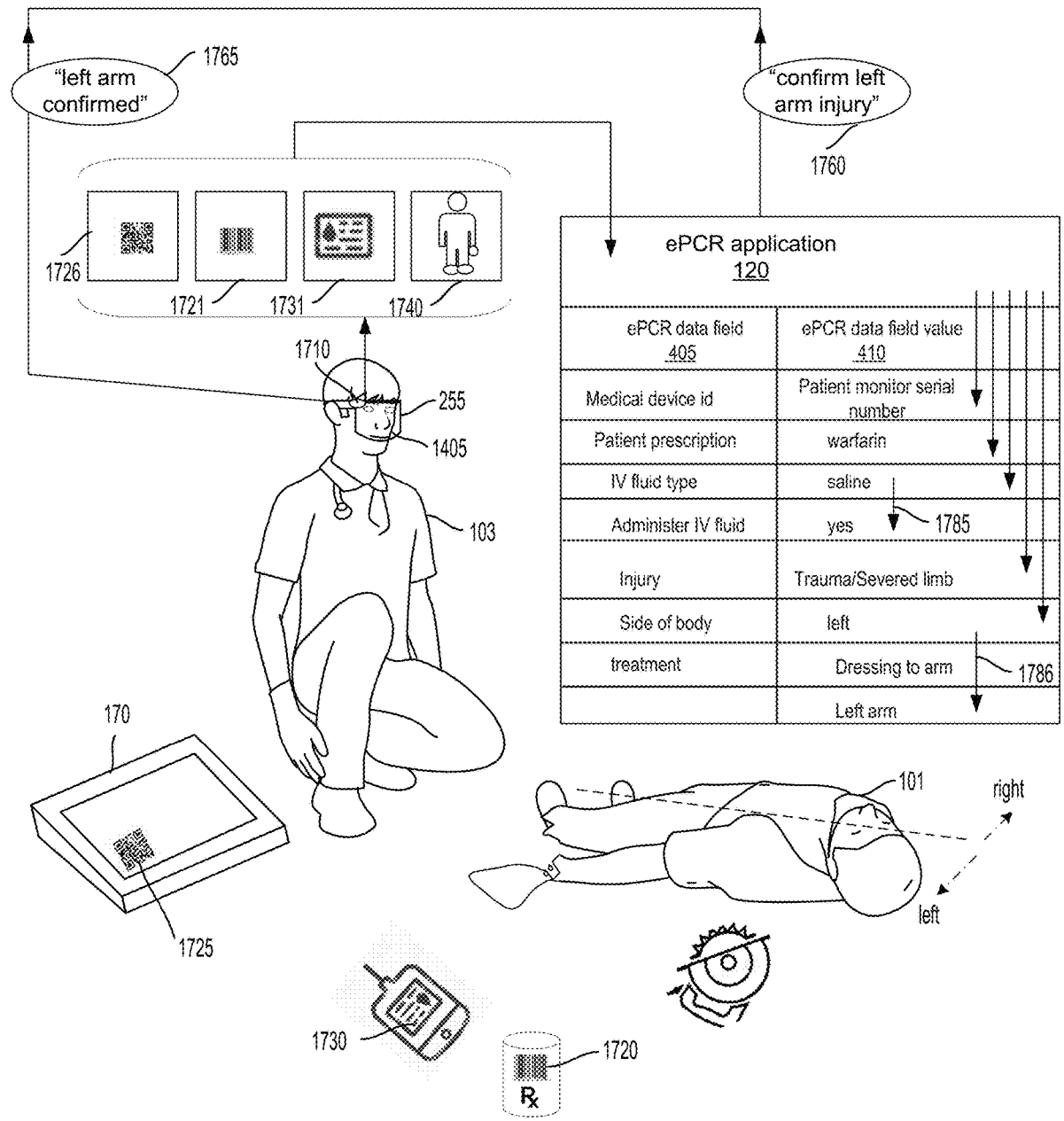
FIG. 17 shows an example of augmented reality glasses with a camera.

Referring to FIG. 17, an example of augmented reality glasses with a camera is shown. In an implementation, the AR glasses 255 may include a camera 1710. The camera 1710 is communicatively coupled to the processor 1832 and may be communicatively coupled to the processor 132 on the computing device 130. In various implementation, the processor 1832 may provide images and/or image interpretation to the processor 132.

The caregiver 103 may control the camera 1710 via audible and/or tactile signals. For example, the caregiver 103 may tap the camera 1710 and, in response, the camera 1710 may capture an image. As other examples, the caregiver 103 may activate the camera 1710 via a gesture to a virtual touchpad displayed on the lens 1405 of the AR glasses 255 and/or via an audible command captured by the microphone 274 (e.g., as shown in FIG. 2B). In an implementation, in response to an activation signal from the caregiver 103, the camera 1710 may capture a bar code image 1721 and/or 1731 of the bar code 1720 and/or 1730 and/or a quick response (QR) code image 1726 of the QR code 1725. For example, the bar code or QR code may identify an item of medical equipment 170 and/or a medication. The camera 1710 may provide the images 1721, 1726 and/or 1731 to the processor 1832. The processor 1832 may provide the images or interpretations of the images (e.g., information extracted from the bar codes and/or QR codes) to the ePCR application 120. In response, the ePCR application 120 may store the information provided by the bar code or QR code in the stored ePCR 125. This information may provide data values for a medication data field or a medical equipment data field. In an implementation, the ePCR application 120 may also infer and fill a data field based on image information. For example, if the medical equipment is an intravenous fluid bag, the ePCR application 120 may infer 1785 a value to populate the medical procedure field of "IV administration," for example with the inferred value of "yes." Further, the ePCR application 120 may determine the type of fluid administered from spoken information by the caregiver, information provided via the virtual touchpad from the AR glasses, and/or a bar code 1730 (or QR code) on the fluid bag, as shown for example in FIG. 17. The ePCR application 120 may further infer medical condition field values based on the types of medications and/or fluids and/or type of medical equipment. The bar code/QR code reading functionality can integrate with the trauma kit that may have bar codes or QR codes on each item in the storage case.

In an implementation, the caregiver 103 may activate the camera 1710 to capture an image of at least a portion of the body of a patient 101. The processor 1832 and/or the processor 132 may interpret the image to identify a medical condition. For example, based an image 1740 of the patient 101 with a severed limb, the ePCR application 120 may identify the injury as "trauma/severed limb" and populate a data field value for the "injury" data field of the stored ePCR. Alternatively or additionally, the caregiver 103 may supplement image information with spoken patient encounter information captured by the microphone 274 and provided to the ePCR application 120. The ePCR application 120 may populate data field values based on a combination of image and speech information from the AR glasses 255. Specific images may be captured that can be tied to text, class or numeric data fields. For instance, when entering data entry fields for injury observations such as "2 inch knife wound to right scapula", the caregiver can speak the instruction, "Capture image" while the camera is aimed at the patient's right scapula, thereby attaching the image to the data entry field describing the injury for more detail.

In an implementation, the caregiver 103 may activate the camera 1710 to capture one or more images of a burn injury or of a bleeding wound with an adjacent pool of blood. The processor 1832 and/or the processor 132 may interpret the image of a burn injury to estimate a percentage of the victim's surface area that is burned. The processor 1832 and/or the processor 132 may implement the ePCR application 120 to automatically enter this estimated percent body burn into the ePCR. In an implementation, the ePCR application 120 may provide the estimated percent body burn to the caregiver 103 via the visual display on the AR glasses 255 and/or via an audible announcement using the speakers 272. The ePCR application 120 may provide the estimated percent body burn as a team alert 1390. In the case of a bleeding injury, the processor 1832 and/or the processor 132 may interpret the image of a bleeding wound with an adjacent pool of blood to estimate a blood loss volume. For example, the ePCR application 120 may estimate an area of the pool of blood and calculate a blood loss volume using an estimated depth of the pool. The ePCR application 120 may automatically enter this value into the ePCR and/or provide this information visibly or audibly to the caregiver and/or the caregiver team in a similar manner to the above described percent burn area. Similarly, the caregiver 103 may activate the camera 1710 to capture an image of a laceration, an abrasion, and/or a contusion. The ePCR application 120 may estimate the length and width of a laceration, an abrasion area, and/or a contusion area and record these values in the stored ePCR.

In an implementation, the caregiver 103 may activate the camera 1710 to capture an image of the victim's entire body. Based on this image, the ePCR application 120 may estimate a height and weight for the victim 101 and calculate medication dosages and/or identify emergency equipment sizes based on the height and/or weight. For example, selection of defibrillation pads, bag valve masks, and endotracheal tubes may depend on the height and/or weight of the victim. The ePCR application 120 may provide a visual and/or audible recommendation for the caregiver 103 for dosages and/or equipment sizes.

In an implementation, the ePCR application 120 may analyze the image 1740 of the patient 101 to identify a side of a patient's body (e.g., right side or left side) that corresponds to an injury and/or medical treatment or procedure. The ePCR application 120 may populate the stored ePCR 125 with the body side information. In an implementation, the ePCR application 120 may generate a caregiver prompt 1760 to confirm an identified side of the body. The caregiver 103 may receive the prompt 1760 via the speaker 272 and/or the lens 1405 of the AR glasses 255. In response to the prompt 1760, the caregiver 103 may provide a confirmation 1765 via the microphone 274 and/or a hand gesture to a virtual touchpad (e.g., the hand gesture 1499 and virtual touchpad 1415 as exemplified in FIG. 14). Based on the identified body side, the ePCR application 120 may infer 1786 one or more data fields based on this identification. For example, if the caregiver 103 provides information to the ePCR application 120 (e.g., via the microphone and/or a hand gesture to the virtual touchpad) that an arm dressing was applied to the patient 101, the ePCR application 120 may automatically infer 1786 that the dressing was applied to the left arm based on other information in the stored ePCR 125 including the body side identification. In various implementations, the ePCR application 120 may use body side identification via image(s) from the camera 1710 for data fields corresponding to a limb, a torso location, a head location, and/or a bilateral organ.

Figure 18:
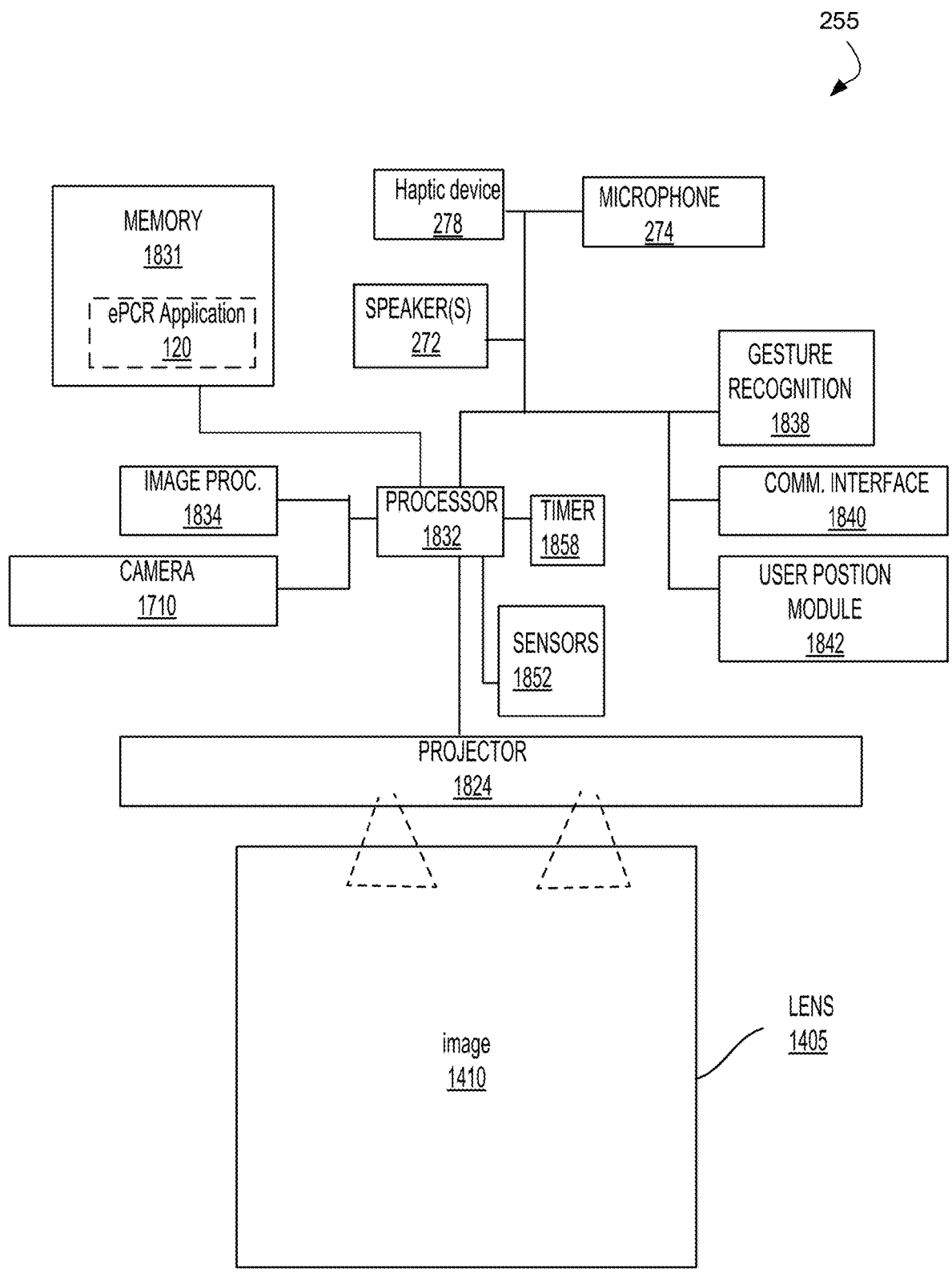
FIG. 18 shows examples of components of AR glasses.

Referring to FIG. 18, examples of components of AR glasses are shown. The AR glasses 255 may include a processor 1832 and a memory 1831. In an implementation, the memory 1831 may include the ePCR application 120 executable by the processor 1832. In some examples, the processor 1832 may be configured to generate code markers, during performance of resuscitation activities, that provide a time-stamped record of a rescue event (e.g., drug infusion/administered, ventilations given, amongst others) for post-rescue event review based on the received and processed images. Additionally or alternatively, the processor 1832 may upload code markers from an external device (e.g., defibrillator, monitor, tablet, external computer, etc.).

In order to provide AR display image(s) 1410 at the visual display 270 on the lens 1405 of virtual objects within the caregiver's field of view, the AR glasses 255 may include an optical projector 1824. For example, the AR display image 1410 may include the virtual touchpad 1415 configured to respond to the real-space (i.e., non-virtual) gesture 1499 by the caregiver. As another example, the AR display image 1410 may include the notifications 1430 and/or overlaid instructions 1610, 1620, 1615, and 1617.

In some examples, the optical projector 1824 is configured to emit light beams in a coordinated manner to an inwardly directed surface of the lens 1405. The emitted light beams are reflected from the lens 1405 to the caregiver's eyes, causing the caregiver 103 to perceive the images of the virtual object(s) as if the virtual object(s) are present within the field of view of the caregiver 103. In an implementation, the optical projector 1824 may be positioned to project the images on or through the lens 1405 to be viewed by the caregiver 103, such that the caregiver 103 perceives the images as virtual three-dimensional objects in interactive combination with physical objects in a mixed reality environment. In some examples, the optical lens 1405 is positioned over the caregiver's eyes such that when the optical projector 1824 is not emitting virtual images, the caregiver 103 perceives a substantially unobstructed view of surrounding objects.

In addition to the processor(s) 1832 and memory 1831, the AR glasses 255 may include one or more of an information and/or image processing module 1834 for two-dimensional and/or three-dimensional information and/or image processing, the camera 1710, a gesture recognition module 1838, and a user position module 1842 in communication with the optical projector 1824.

The image processing module 1834 may receive and process three dimensional information about the rescue scene, for example, to help identify one or more resuscitation activities being performed by the caregiver 103. For instance, a three-dimensional sensor may provide information about the positioning and size of objects relative to one another, though, images recorded by a digital camera may provide more definitive information for identifying particular objects, such as a medical device and/or other treatment equipment and devices, a rescuer, patient, etc.

The image processing module 1834 may also receive and process two-dimensional images of the rescue scene obtained by the camera 1710 and/or another optical sensor to extract and/or interpret image information and/or refine an accuracy or specificity of physical objects identified based on the three dimensional information.

The camera 1710 may include one or more of a digital camera, RGB camera, digital video camera, red-green-blue sensor, and/or depth sensor for capturing visual information and static or video images of the rescue scene. The camera 1710 may be positioned to substantially correspond to the caregiver's field of view. In an implementation, the AR glasses 255 may include multiple cameras, such as a camera positioned adjacent to each of the caregiver's eyes to generate a stereo-image, which substantially corresponds to the caregiver's field of view. The processor 1832 and/or the image processing module 1834 may process the stereo-image to determine depth information for objects in the rescue scene. In an implementation, one or more cameras may face to the side (e.g., to the right or left of the caregiver's field of view) to, for example, capture a 180 degree or larger view of the rescue scene. Another camera may obtain images of the caregiver's eyes to detect, for example, when the caregiver's gaze changes direction and/or moves from one object to a different object. In some instances, the ePCR application 120 may identify resuscitation activities being performed by the caregiver 103 based on captured images from the camera 1710. For example, if the three-dimensional information and/or captured images show the caregiver's hands placed against the patient's chest, it may be determined that the caregiver 103 is providing chest compressions.

Although designs differ from different vendors, as is known in the art, a camera usually comprises a charge-coupled device (CCD) or complementary metal-oxide-semiconductor (CMOS) imaging sensor, a lens, a multifunctional video control chip, and a set of discrete components (e.g., capacitor, resistors, and connectors). The imaging sensor may record an image and the video control chip may process the image. The video control chip may provide the processed image to the image processing module 1834 for further processing and for identifying physical objects contained in the captured images. The processing module 1834 may also prepare certain images for transmission from the AR glasses 255 to other electronic/computing devices. In some examples, the camera 1710 may include one or more three-dimensional optical sensors for obtaining three-dimensional information about the rescue scene and/or cameras for capturing still or moving two-dimensional images of the rescue scene. Three-dimensional information may include distance or depth information about how far away physical objects are from the sensor, as well as their size/dimensions. The processor 1832 may process three-dimensional information and/or images from the optical sensors to produce a three-dimensional representation of the rescue scene. The three-dimensional representation may be useful for the identification of the physical objects present at the rescue scene including, for example, caregivers 103, patients, bystanders, therapeutic medical devices, monitoring devices, medical supplies, as well as environmental objects, such as a street or driveway, trees, buildings, power lines, automobiles, trucks, trains, and other objects, which may impact how and where treatment is provided to a patient. The processor 1832 may also use other information such as captured images/video to identify physical objects present at the rescue scene.

The image processing module 1834 may be configured to perform processing routines on the collected three-dimensional information and images to assist with operation of the AR glasses 255 and, in particular, with positioning and/or movement of images of virtual objects as the caregiver 103 changes position. In some examples, the AR glasses 255 may also be configured to apply spatially sensitive rules for generated virtual objects in the three-dimensional representation based on a position of identified physical objects. The spatially sensitive rules may provide a contextual basis for displaying images of the virtual object to the caregiver 103. For example, the processor 1832 may identify a position of the patient in captured images. Any images of virtual objects displayed on the visual display of the AR device in the caregiver's field of view may be positioned so as not to obscure the view of the patient. Other images of virtual objects may be projected on the visual display of the AR device to appear to rest on the patient. For example, a CPR performance indicator icon for the patient may be displayed as resting on the patient's chest. The processor 1832 and/or the image processor 1834 may be configured to apply a variety of known image processing algorithms for identifying objects in captured images including based on color (e.g., pixel color) of certain portions of captured images. In other examples, shape recognition algorithms may be applied to captured images to identify shapes of different objects. For example, the image processor 1834 may recognize a caregiver's hand based on a combination of recognition of skin tones in the captured image and identification of shapes of the fingers and palm in the captured image.

The user position module 1842 may generate and provide one or more spatially sensitive rules. The AR glasses 255 may be configured to display images of the virtual three-dimensional objects projected or otherwise provided by the optical projector 1824 in accordance with and/or to abide by the one or more spatially sensitive rules. For example, the spatially sensitive rules may comprise instructions linking a position or orientation of physical objects or environmental conditions with types of information to be displayed to the caregiver 103 through virtual images. In a similar manner, the instructions may tailor the information displayed at the lens 1405 to particular activities or actions (e.g., resuscitation activities) performed by the caregiver 103 wearing the AR glasses 255. Spatially sensitive rules may further comprise instructions for positioning images of the three-dimensional virtual objects in relation to the physical objects within the caregiver's field of view. For example, the spatially sensitive rules may require that images of visual objects be projected over (e.g., appear to be on top of) certain physical objects within the caregiver's field of view. As discussed herein, the images of the visual objects may be modified as the caregiver manipulates physical object(s).

The AR glasses 255 may further include AR components that supplement and/or enhance visual feedback projected or displayed within the caregiver's field of view. For example, the AR glasses 255 may include the speaker(s) 272 for providing caregiver prompts 140 and/or other audible indicators to the caregiver 103 and audio input components, such as the microphone 274, for providing patient encounter information 110 to the ePCR application 120.

In some examples, the AR glasses 255 may include the haptic device(s) 278 (e.g., a vibration motor) configured to provide vibration feedback to the caregiver 103. The haptic device 278, and similarly the devices 158 and/or 268, may be a vibration motor and may be configured to provide vibration feedback to the caregiver 103. The haptic device 278, 158 and/or 268 may be configured to emit various patterns and intensities of vibration to convey information to the caregiver 103. For example, the haptic device 278, 158, and/or 268 may be a compact linear actuator that vibrates at varying patterns and intensities as directed by, for example, the processor 132 or 1832. Such an actuator may include a spring and magnet for manipulating a mass coupled thereto. In some instances, providing vibration feedback, rather than audio alerts and/or visual indicators, may be less likely to distract other caregivers 103 from resuscitation activities they are performing. In other examples, the vibration feedback may supplement audio alerts and/or visual indicators or replace the audio alerts in a noisy environment.

In some examples, separate components or devices in communication with the AR glasses 255 may provide vibration feedback. For example, the caregiver 103 may wear a wrist device (e.g., the watch or bracelet 250) comprising a linear actuator motor configured to vibrate at variable patterns and intensities to convey information to the wearer. The AR glasses 255 may be configured to cause the separate vibration feedback device to vibrate in a coordinated manner with images of a virtual object projected by the AR glasses 255. For example, the separate vibration device may vibrate to indicate to the caregiver 103 when to begin and release a chest compression, ventilation bag compression, or similar action.

The AR glasses 255 may further include a communications interface 1840, such as a wireless transceiver, configured to communicatively couple the AR glasses 255 with one or more of the mobile computing device 130, the remote computing device 190 and/or 179, the CAD computing device 174, the medical records computing device 178 and/or the medical device 170. The communications interface 1840 may include short range or long range data communications features, such as a wireless data transceiver, for wireless communication between the AR glasses 255 and other electronic devices located at, or remote from, the rescue scene. The communication protocol may include Bluetooth®, Zigbee, Wi-Fi, and/or an 802.18 data transmission protocol. In some examples, the communications interface may transmit images captured by the camera 1710. In some examples, images may be transmitted to the remote electronic device in substantially real-time. In other examples, obtained images may be stored locally on the AR glasses 255, for example in the computer readable memory 1831. The stored images may be transmitted by the communications interface 1840 to the remote electronic device as a batch download at predetermined intervals. The communications interface 1840 may also be configured to receive information, such as instructions to provide feedback to the caregiver 103 from the ePCR application 120. In some examples, the AR glasses 255 may be in communication with other devices (e.g., medical device, defibrillator, patient monitor, sensors, communications device, smartwatch, wearable device, etc.) connected to, or associated with, the caregiver 103 to form a personal area network (PAN). Information and instructions may be shared between the different devices so that feedback may be provided to the caregiver 103. In some examples, the AR glasses 255 may serve as a front end (e.g., a remote display) for a separate medical device, system, or network. For example, the AR glasses 255 may be configured to display information generated by a medical device 170 to inform the caregiver 103 about the status of the device.

In some examples, the communications interface 1840 may be configured to transmit data to an intermediate device having long-range data transmission capabilities. The intermediate device (e.g., a smartphone, tablet, laptop computer, or PDA) may receive and, in some cases, perform additional processing on the received data. The communications interface 1840 may transmit additionally processed data to an external electronic device, computer network, or database using the long-range data transmission capabilities of the intermediate device.

In some further examples, the communications interface 1840 may comprise circuitry for long-range data transmission directly from the device itself. Long-range data transmission may be performed by a long-range data transmitter or transceiver, for example a Wi-Fi transmitter or a cellular transmitter (e.g., 3G, 4G, or 5G enabled systems). Data collected by the device 1820 may be sent to external sources by the long-range data transmitter or transceiver. The long-range communications may be via a cellular and/or a computer network.

The gesture recognition module 1838 may be configured to identify the caregiver's hands within images obtained by the AR glasses 255 and, based on the position, orientation, and movement of the hands, may identify gestures performed by the caregiver 103 for the purpose of controlling operation of the AR glasses 255 and/or for manipulating the virtual touchpad 1415 and/or other display features provided to the caregiver 103 by the optical projector 1824 at the lens 1405. For example, the caregiver may use pre-programmed gestures to scroll through ePCR information displayed by the optical projector 1824 at the lens 1405 and/or to toggle through different screens provided by the ePCR application 120. In an implementation, a gesture may be a predetermined coordinated movement performed by the caregiver 103 that identifies a rescue scene activity. For example, the caregiver 103 could turn her palms downward and mimic a pushing motion to represent a chest compression and/or turn her wrists upward in a manner that signifies compressing a ventilation bag.

The AR glasses 255 may further comprise a number of sensors 1852 (e.g., motion sensors, accelerometers, light sensors, capacitive sensors, proximity sensors, etc.) for measuring additional information about the wearer's field of view and the surrounding environment. For example, the sensor 1852 of the AR glasses 255 may determine the caregiver's position relative to other objects and/or determine when the caregiver's position and/or field of view changes (e.g., when the caregiver 103 moves his or her head or to identify detected physical objects in the field of view).

In some examples, the AR glasses 255 further comprise a timer 1858, for tracking passage of time (e.g., during a resuscitation activity) and/or for determining a current time. The timer 1858 may be configured to communicate with an external electronic device, such as the computing device 130, the medical device 170, the watch 250 and/or an external computer network to determine a current time. The AR glasses 255 may display the current time within the caregiver's field of view with the optical projector 1824. In addition, the current time may be automatically associated with data from the camera 1710 and/or data captured via hand gestures or speech by the AR glasses 255 to provide a timestamped record of events at the rescue scene to the ePCR application 120. The ePCR application 120 may use the timestamps to correlate the data from the AR glasses 255 with data recorded from other devices such as, for example, the medical device 170 or other devices (e.g., as described for example, in regard to FIGS. 1D and 9) and/or the wearable user interface devices from other caregivers (e.g., the wearable user interface devices associated with caregiver team as described, for example, in regard to FIGS. 10-13). The ePCR application 120 may correlate the time-stamped data from the AR glasses 255 to accurately record multiple resuscitation activities being performed for the patient. The ePCR application 120 may also use data from the timer 1858 to determine a duration of certain events during the rescue. For example, the timer 1858 may measure an amount of time from occurrence of a physiological event, such as an elapsed time in which treatment was provided to the patient. Additionally or alternatively, the ePCR application 120 may use timing information from the timer 1858 to provide the caregiver prompts 140 for scheduled treatment events. For example, a treatment protocol may include administering a particular medication to the patient at specific time intervals, or different medications at specific time intervals. The ePCR application 120 may automatically track a period of time from administration of the medication, and provide a caregiver prompt indicating that a next dose should be provided based on data from the timer 1858. In a similar manner, the timer 1858 may track and provide to the ePCR application 120 a time that has elapsed for an ongoing resuscitation activity, such as chest compressions or ventilations. Accordingly, based at least in part on the time of events, the ePCR application 120 may provide the caregiver prompts 140 with an indication of which activity should be performed at any given time.

Figure 19:
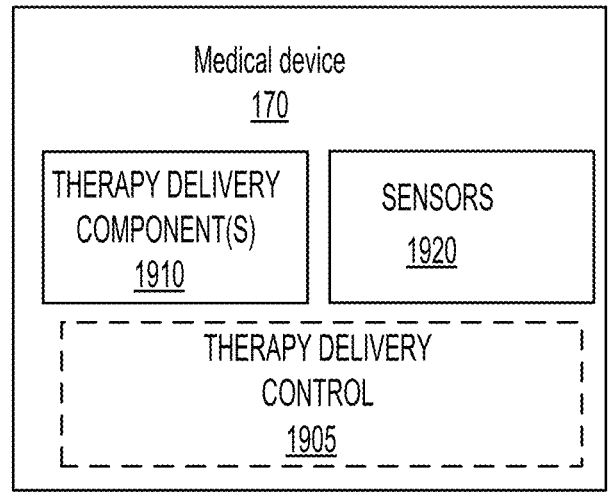
FIG. 19 shows an example of medical device components.

Referring to FIG. 19, with further reference to FIGS. 1B-FIG. 17, an example of medical device components is shown. In various implementations, the medical device 170 may be a defibrillator, patient monitor, defibrillator/monitor, an automated compression device, a therapeutic cooling device, an extracorporeal membrane oxygenation (ECMO) device, a ventilation device, combinations thereof, or another type of medical device configured to couple to one or more therapy delivery components to provide therapy to the patient. In an implementation, the medical device 170 may be an integrated therapy delivery/monitoring device within a single housing. The single housing may surround, at least in part, the therapy delivery components and the monitoring components. In an implementation, the medical device 170 may be a modular therapy delivery/monitoring device, with patient therapy components in one unit communicatively coupled to a patient monitoring unit without therapy delivery components.

The medical device 170 may be, for example, a therapeutic medical device capable of delivering a medical therapy. Thus, the medical device 170 may include the therapy delivery control module 1905. For example, the therapy delivery control module 1905 may be an electrotherapy delivery circuit that includes one or more capacitors configured to store electrical energy for a pacing pulse or a defibrillating pulse. The electrotherapy delivery circuit may further include resistors, additional capacitors, relays and/or switches, electrical bridges such as an H-bridge (e.g., including a plurality of insulated gate bipolar transistors or IGBTs), voltage measuring components, and/or current measuring components. As another example, the therapy delivery control module 1905 may be a compression device electro-mechanical controller configured to control a mechanical compression device. As a further example, the therapy delivery control module 1905 may be an electromechanical controller configured to control drug delivery, temperature management, ventilation, and/or other type of therapy delivery. Alternatively, the medical device 170 may be configured to provide patient monitoring and/or diagnostic care without providing medical therapy.

In various implementations, the medical therapy may be electrical therapy (e.g. defibrillation, cardiac pacing, synchronized cardioversion, diaphragmatic or phrenic nerve stimulation) and the medical device 170 may be a defibrillator, a defibrillator/monitor, a mechanical ventilator such as the ZOLL Z-Vent, and/or another medical device configured to provide electrotherapy. As another example, the medical therapy may be chest compression therapy for treatment of cardiac arrest and the medical device 170 may be a mechanical chest compression device such as a belt-based chest compression device or a piston-based chest compression device. As other examples, the medical therapy may be ventilation therapy, therapeutic cooling or other temperature management, invasive hemodynamic support therapy (e.g. Extracorporeal Membrane Oxygenation (ECMO)), etc. and the medical device 170 may be a device configured to provide a respective therapy. In an implementation, the medical device 170 may be a combination of one or more of these examples. The therapeutic medical device may include patient monitoring capabilities via one or more sensors. These types of medical therapy and devices are examples only and not limiting of the disclosure.

The medical device 170 may include, incorporate, and/or be configured to couple to one or more therapy delivery component(s) and/or one or more sensor device(s). The therapy delivery component(s) 1910 are configured to deliver therapy to the patient and may be configured to couple to the patient. For example, the therapy delivery component(s) 1910 may include one or more of electrotherapy electrodes including defibrillation electrodes and/or pacing electrodes, chest compression devices (e.g., one or more belts or a piston), ventilation devices (e.g., a mask and/or tubes), drug delivery devices, fluid delivery devices, intravenous devices, etc. and combinations thereof. The medical device 170 may include the one or more therapy delivery component(s) 1910 and/or may be configured to couple to the one or more therapy delivery component(s) 1910 in order to provide medical therapy to the patient. The therapy delivery component(s) 1910 may be configured to couple to the patient 101. For example, the caregiver 103 may attach the electrodes to the patient 101 and the medical device 170 (e.g., a defibrillator or defibrillator/patient monitor) may provide electrotherapy to the patient 101 via the defibrillation electrodes. These examples are not limiting of the disclosure as other types of medical devices, therapy delivery components, sensors, and therapy are within the scope of the disclosure. In various implementation, the therapy delivery component(s) 1910 may be configured to provide sensor data and/or be coupled to and/or incorporate sensors. For example, the electrotherapy electrodes may provide sensor data such as transthoracic impedance, ECG, heart rate, etc. Further the electrotherapy electrodes may include and or be coupled to a chest compression sensor. As another example, the ventilation devices may be coupled to and/or incorporate flow sensors, gas species sensors (e.g., oxygen sensor, carbon dioxide sensor, etc.), etc. As a further example, the intravenous devices may be coupled to and/or incorporate temperature sensors, flow sensors, blood pressure sensors, etc. As another example, the compression devices may be coupled to and/or incorporate chest compression sensors, patient position sensors, etc. The therapy delivery control module 1905 may be configured to couple to and control the therapy delivery component(s) 1910.

The medical device 170 may include, incorporate, and/or be configured to couple to the one or more sensor(s) 1920 which may be configured to couple to the patient 101. The sensor(s) 1920 are configured to provide signals indicative of sensor data to the device 170. The sensor(s) 1920 may be configured to couple to the patient. For example, the sensor(s) 1920 may include cardiac sensing electrodes, a chest compression sensor, and/or ventilation sensors. In various implementations, the sensor(s) 1920 may include one or more sensor devices configured to provide sensor data that includes, for example, but not limited to electrocardiogram (ECG), blood pressure, heart rate, pulse oxygen level, respiration rate, heart sounds, lung sounds, respiration sounds, tidal $CO_2$, saturation of muscle oxygen ($SMO_2$), arterial oxygen saturation ($SpO_2$), cerebral blood flow, electroencephalogram (EEG) signals, brain oxygen level, tissue pH, tissue fluid levels, images and/or videos via ultrasound, laryngoscopy, and/or other medical imaging techniques, near-infrared reflectance spectroscopy, pneumography, cardiography, and/or patient movement. Images and/or videos may be two-dimensional or three-dimensional.

The sensor(s) 1920 may include sensing electrodes, ventilation sensors, temperature sensors, chest compression sensors, etc. For example, the sensing electrodes may include cardiac sensing electrodes. The cardiac sensing electrodes may be conductive and/or capacitive electrodes configured to measure changes in a patient's electrophysiology, for example to measure the patient's ECG information. In an implementation, the sensing electrodes may be configured to measure the transthoracic impedance and/or a heart rate of the patient 101. The ventilation sensors may include spirometry sensors, flow sensors, pressure sensors, oxygen and/or carbon dioxide sensors such as, for example, one or more of pulse oximetry sensors, oxygenation sensors (e.g., muscle oxygenation/pH), $O_2$ gas sensors and capnography sensors, and combinations thereof. The temperature sensors may include an infrared thermometer, a contact thermometer, a remote thermometer, a liquid crystal thermometer, a thermocouple, a thermistor, etc. and may measure patient temperature internally and/or externally. The chest compression sensor may include one or more motion sensors including, for example, one or more accelerometers, one or more force sensors, one or more magnetic sensors, one or more velocity sensors, one or more displacement sensors, etc. The chest compression sensor may be, for example, but not limited to, a compression puck, a smartphone, a hand-held device, a wearable device, etc. The chest compression sensor may be configured to detect chest motion imparted by a rescuer and/or an automated chest compression device (e.g., a belt system, a piston system, etc.). The chest compression sensor may provide signals indicative of chest compression data including displacement data, velocity data, release velocity data, acceleration data, compression rate data, dwell time data, hold time data, blood flow data, blood pressure data, etc. In an implementation, the sensing electrodes and/or the electrotherapy electrodes may include or be configured to couple to the chest compression sensor.

The one or more sensors 1920 may generate signals indicative of physiological parameters of the patient 101. For example, the physiological parameters may include one or more of at least one vital sign, an ECG, blood pressure, heart rate, pulse oxygen level, respiration rate, heart sounds, lung sounds, respiration sounds, tidal $CO_2$, saturation of muscle oxygen ($SMO_2$), arterial oxygen saturation ($SpO_2$), cerebral blood flow, electroencephalogram (EEG) signals, brain oxygen level, tissue pH, tissue fluid levels, physical parameters as determined via images and/or videos such as via ultrasound and/or laryngoscopy, parameters determined via near-infrared reflectance spectroscopy, pneumography, and/or cardiography, etc. The ultrasound images may include ultrasound images of a patient's heart, carotid artery, and/or other components of the cardiovascular system. Additionally or alternatively the one or more sensors 1920 may generate signals indicative of chest compression parameters, ventilation parameters, drug delivery parameters, fluid delivery parameters, etc.

In addition to delivering therapy to the patient, the therapy delivery component(s) 1910 may include, be coupled to, and/or function as sensors and provide signals indicative of sensor data to the medical device 170. For example, the defibrillation electrodes may be configured as cardiac sensing electrodes as well as electrotherapy delivery devices and may provide signals indicative of transthoracic impedance, electrocardiogram (ECG), heart rate and/or other physiological parameters. As another example, a therapeutic cooling device may be an intravenous cooling device. Such a cooling device may include an intravenous (IV) device as a therapy delivery component configured to deliver cooling therapy and sense the patient's temperature. For example, the IV device may be a catheter that includes saline balloons configured to adjust the patient's temperature via circulation of temperature controlled saline solution. In addition, the catheter may include a temperature probe configured to sense the patient's temperature. As a further example, an IV device may provide therapy via drug delivery and/or fluid management. The IV device may also monitor and/or enable monitoring of a patient via blood sampling and/or venous pressure monitoring (e.g., central venous pressure (CVP) monitoring).

The medical device 170 may be configured to receive the sensor signals (e.g., from the therapy delivery component(s) 1910 and/or the sensor(s) 1920) and to process the sensor signals to determine and collect the patient data. The patient data may include patient data which may characterize a status and/or condition of the patient (e.g., physiological data such as ECG, heart rate, respiration rate, temperature, pulse oximetry, non-invasive hemoglobin parameters, capnography, oxygen saturation ($SpO_2$), end tidal carbon dioxide ($EtCO_2$), invasive blood pressure (IBP), non-invasive blood pressures (NIBP), tissue pH, tissue oxygenation, Near Infrared Spectroscopy (NIRS) measurements, etc.). Additionally or alternatively, the patient data may characterize the delivery of therapy (e.g., chest compression data such as compression depth, compression rate, etc.) and/or the patient data may characterize a status and/or condition of the medical equipment used to treat the patient (e.g., device data such as shock time, shock duration, attachment of electrodes, power-on, etc.).

The processors as described herein (e.g., 132, 192, 1832) are physical processors (i.e., an integrated circuit configured to execute operations on a respective device as specified by software and/or firmware stored in a computer storage medium) operably coupled, respectively, to at least one memory device (e.g., 134, 194, 1831). The processors may be intelligent hardware devices (for example, but not limited to, a central processing unit (CPU), a graphics processing unit (GPU), one or more microprocessors, a controller or microcontroller, an application specific integrated circuit (ASIC), a digital signal processor (DSP), etc.) designed to perform the functions described herein and operable to carry out instructions on a respective device. Each of the processors may be one or more processors and may be implemented as a combination of hardware devices (e.g., a combination of DSP and a microprocessor, a plurality of microprocessors, one or more microprocessors in conjunction with a DSP core, or another such configuration). Each of the processors may include multiple separate physical entities that may be distributed in an associated computing device. Each of the processors is configured to execute processor-readable, processor-executable software code containing one or more instructions or code for controlling the processors to perform the functions as described herein. The processors may utilize various architectures including but not limited to a complex instruction set computer (CISC) processor, a reduced instruction set computer (RISC) processor, or a minimal instruction set computer (MISC). In various implementations, each processor may be a single-threaded or a multi-threaded processor. The processors may be, for example, but not limited to, an Intel® Itanium® or Itanium 2® processor(s), AMD® Opteron®, Athlon MP® processor(s), a Motorola® line of processor, or an ARM, Intel Pentium Mobile, Intel Core i5 Mobile, AMD A6 Series, AMD Phenom II Quad Core Mobile, or like devices.

The memories (e.g., 134, 194, 1831) refer generally to a computer storage medium, including but not limited to RAM, ROM, FLASH, disc drives, fuse devices, and portable storage media, such as Universal Serial Bus (USB) flash drives, etc. Each of the memories may include, for example, random access memory (RAM), or another dynamic storage device(s) and may include read only memory (ROM) or another static storage device(s) such as programmable read only memory (PROM) chips for storing static information such as instructions for a coupled processor. Each memory may include USB flash drives that may store operating systems and other applications. The USB flash drives may include input/output components, such as a wireless transmitter and/or USB connector that can be inserted into a USB port of another computing device. Each memory may be long term and/or short term, and are not to be limited to a particular type of memory or number of memories, or type of media upon which memory is stored. Each memory includes a non-transitory processor-readable storage medium (or media) that stores the processor-readable, processor-executable software code. Each memory may store information and instructions. For example, each memory may include flash memory and/or another storage media may be used, including removable or dedicated memory in a mobile or portable device. As another example, hard disks such as the Adaptec® family of SCSI drives, an optical disc, an array of disks such as RAID (e.g. the Adaptec family of RAID drives), or another mass storage devices may be used. Each memory may include removable storage media such as, for example, external hard-drives, floppy drives, flash drives, zip drives, compact disc-read only memory (CD-ROM), compact disc-re-writable (CD-RW), or digital video disk-read only memory (DVD-ROM).

Communicatively coupled devices as described herein may transmit and/or receive information via a wired and/or wireless communicative coupling. The information may include information stored in at least one memory. The information may include, for example, but not limited to, resuscitative treatment information, physiological information, patient information, rescuer and/or caregiver information, location information, rescue and/or medical treatment center information, etc. The communicative couplings may enable short-range and/or long-range wireless communication capabilities which may include communication via near field communication, ZigBee®, Wi-Fi, Bluetooth®, satellite (s), radio waves, a computer network (e.g., the Internet), a cellular network, a Local Area Network (LAN), Wide Area Network (WAN), a mesh network, an ad hoc network, or another network. The communicative couplings may include, for example, an RS-232 port for use with a modem based dialup connection, a copper or fiber 10/100/1000 Ethernet port, or a Bluetooth® or Wi-Fi interface.

Displays as described herein may provide a graphical user interface (GUI). A particular display may be, for example, but not limited to, a touchscreen display, an AR display, a liquid crystal display (LCD), and/or a light emitting diode (LED) display. The touchscreen may be, for example, a pressure sensitive touchscreen or a capacitive touchscreen. The touchscreen may capture user input provided via touchscreen gestures and/or provided via exertions of pressure on a particular area of the screen. The displays may provide visual representations of data captured by and/or received at the medical device 170. The visual representations may include still images and/or video images (e.g., animated images).

The mobile computing device 130 may include one or more user input devices such as, for example, a keyboard, a mouse, joystick, trackball, or other pointing device, a microphone, a camera, etc. In an implementation, the user input devices may be configured to capture information, such as, for example, patient medical history (e.g., medical record information including age, gender, weight, body mass index, family history of heart disease, cardiac diagnosis, co-morbidity, medications, previous medical treatments, and/or other physiological information), physical examination results, patient identification, caregiver identification, healthcare facility information, etc.

The processor, memory, communication interfaces, input and/or output devices and other components described above are meant to exemplify some types of possibilities. In no way should the aforementioned examples limit the scope of the disclosure, as they are only exemplary embodiments of these components.

Various modifications and additions can be made to the exemplary embodiments discussed without departing from the scope of the present disclosure. For example, while the embodiments described above refer to particular features, the scope of the disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

The invention claimed is:

1. A patient data charting system for automated data capture by an electronic patient care record (ePCR) generated during a patient encounter with emergency medical services (EMS), the system comprising:
 a local computing device comprising
  at least one processor, and
  a memory storing at least a portion of a medical protocol and the ePCR comprising a plurality of ePCR data fields; and
 at least one user interface device communicatively coupled to the local computing device and comprising a microphone and a speaker,
 wherein the microphone is configured to capture spoken patient encounter information,
 wherein the at least one processor is configured to
  receive the spoken patient encounter information as text information from a speech-to-text conversion application,
  determine at least one ePCR data field value based on the text information,
  populate at least one ePCR data field of the plurality of ePCR data fields with the at least one ePCR data field value,
  generate one or more caregiver prompts based on the at least one ePCR data field value, the one or more caregiver prompts comprising a reminder for a caregiver to perform a patient care activity, wherein the at least a portion of the medical protocol associates the at least one ePCR data field value with the patient care activity, and
  provide the one or more caregiver prompts to the speaker, and
 wherein the speaker is configured to provide the one or more caregiver prompts as audible prompts for the caregiver.

2. The patient data charting system of claim 1, wherein the speech-to-text conversion application resides on the local computing device and the at least one processor is configured to:
 wirelessly receive the captured spoken patient encounter information from the at least one user interface device, and
 provide the captured spoken patient encounter information to the speech-to-text conversion application.

3. The patient data charting system of claim 1,
 wherein the local computing device comprises a location device configured to determine location information associated with the patient encounter, and
 wherein the at least one processor is configured to determine the at least one ePCR data field value based on the location information.

4. The patient data charting system of claim 3, wherein the at least one ePCR data field value comprises a time determined from the location information, the time comprising one or more of an en-route-to-patient-scene time, an at-patient-arrival-time, an at-patient-side duration time, an in-transport time, an estimated time of arrival at a hospital, or a hospital arrival time.

5. The patient data charting system of claim 4, wherein the at least one processor is configured to generate a geofence and the time determined from the location information is based on the geofence.

6. The patient data charting system of claim 1, wherein the text information comprises one or more predetermined keywords and the at least one processor is configured to identify the at least one ePCR data field based on the one or more predetermined keywords.

7. The patient data charting system of claim 6, wherein the one or more predetermined keywords correspond to one or more of (a) an ePCR data field identifier corresponding to the at least one ePCR data field, or (b) the at least one ePCR data field value.

8. The patient data charting system of claim 7, wherein the at least one processor is configured to populate at least one additional ePCR data field with an inferred data field value based on the at least one of the ePCR data field value.

9. The patient data charting system of claim 1, wherein the spoken patient encounter information comprises caregiver speech and patient speech, and wherein the at least one processor is configured to:
 recognize that the spoken patient encounter information includes the patient speech; and
 differentiate between the patient speech and the caregiver speech.

10. The patient data charting system of claim 9, wherein the microphone is a first microphone configured to capture the spoken patient encounter information from the caregiver and comprising a second microphone configured to capture the patient speech, and wherein the at least one processor is configured to differentiate between the patient speech and the caregiver speech based on whether the spoken patient encounter information is from the first microphone or the second microphone.

11. The patient data charting system of claim 10, wherein the at least one processor is configured to differentiate between the patient speech and the caregiver speech based on voice recognition of the caregiver speech.

12. The patient data charting system of claim 10, wherein the at least one processor is configured to identify a portion of the plurality of ePCR data fields based on the caregiver speech and to determine data field values for the portion of the plurality of ePCR data fields based on the patient speech.

13. The patient data charting system of claim 10, wherein based on recognizing that the spoken patient encounter information includes the patient speech, the at least one processor is configured to determine a null value for at least one ePCR data field that is incompatible with a verbally responsive patient.

14. The patient data charting system of claim 13, wherein the at least one ePCR data field that is incompatible with the verbally responsive patient is in one or more of a cardiac arrest data section of the ePCR or an airway data section of the ePCR.

15. The patient data charting system of claim 14, wherein the ePCR is National Emergency Medical Services Information Standard (NEMSIS) compliant and the at least one ePCR data field that is incompatible with the verbally responsive patient comprises one or more of an eArrest data field in the cardiac arrest data section or an eAirway data field in the airway data section.

16. The patient data charting system of claim 1, wherein the at least one processor is configured to:
identify at least one unpopulated ePCR data field associated with at least one populated ePCR data field, and
generate a particular caregiver prompt comprising at least one request for at least one data field value for the at least one unpopulated ePCR data field,
wherein the particular caregiver prompt comprises one or more of a visible prompt, an audible prompt, and a haptic prompt.

17. The patient data charting system of claim 16, wherein the at least one processor is configured to identify the at least one unpopulated ePCR data field based on the medical protocol stored in the memory.

18. The patient data charting system of claim 16, wherein the at least one processor is configured to cause the speaker to repeat the particular caregiver prompt comprising the at least one request for the at least one data field value for the at least one unpopulated ePCR data field, wherein the particular caregiver prompt is repeated until (a) the at least one processor receives a caregiver response via the microphone and/or (b) the particular caregiver prompt is repeated a pre-determined number of times.

19. The patient data charting system of claim 1, wherein the patient care activity is an intubation procedure.

20. The patient data charting system of claim 1, wherein the one or more caregiver prompts comprise alarms based on the at least one ePCR data field value.

21. The patient data charting system of claim 20, wherein the alarms comprise one or more of patient care warnings based on the at least one ePCR data field value or timed alarms for the patient care activity.

22. The patient data charting system of claim 21, wherein the patient care warnings comprise one or more of a drug contraindication and a medical therapy contraindication.

23. The patient data charting system of claim 21, wherein the at least one ePCR data field value comprises at least one physiological parameter and wherein the at least one processor is configured to:
compare the at least one physiological parameter to a target value or a target range,
determine that the at least one physiological parameter is unequal to the target value or outside of the target range, and
generate a patient care warning that indicates that the at least one physiological parameter is unequal to the target value or outside of the target range.

24. The patient data charting system of claim 1, wherein the local computing device is configured to communicatively couple to an EMS dispatch system and the at least one processor is configured to:
receive EMS dispatch information, and
determine one or more additional ePCR data field values based on the EMS dispatch information.

25. The patient data charting system of claim 1, wherein the local computing device is configured to communicatively couple to one or more medical devices and the at least one processor is configured to:
receive patient data from the one or more medical devices, and
determine one or more additional ePCR data field values based on the patient data from the one or more medical devices.

* * * * *

UNITED STATES PATENT AND TRADEMARK OFFICE
CERTIFICATE OF CORRECTION

| | | |
|---|---|---|
| PATENT NO. | : 12,080,391 B2 | Page 1 of 1 |
| APPLICATION NO. | : 17/396206 | |
| DATED | : September 3, 2024 | |
| INVENTOR(S) | : Alexander N. Moghadam et al. | |

It is certified that error appears in the above-identified patent and that said Letters Patent is hereby corrected as shown below:

In the Claims

In Claim 8, Column 54, Line 59, delete "of the".

Signed and Sealed this
Twenty-second Day of October, 2024

Katherine Kelly Vidal
*Director of the United States Patent and Trademark Office*